United States Patent
Spahn et al.

(10) Patent No.: US 11,670,399 B2
(45) Date of Patent: Jun. 6, 2023

(54) SYSTEMS AND METHODS FOR PREDICTING GLYCOSYLATION ON PROTEINS

(71) Applicant: The Regents of the University of California, Oakland, CA (US)

(72) Inventors: Philipp N. Spahn, San Diego, CA (US); Nathan E. Lewis, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1278 days.

(21) Appl. No.: 15/573,239

(22) PCT Filed: May 18, 2016

(86) PCT No.: PCT/US2016/033136
§ 371 (c)(1),
(2) Date: Nov. 10, 2017

(87) PCT Pub. No.: WO2016/187341
PCT Pub. Date: Nov. 24, 2016

(65) Prior Publication Data
US 2018/0101643 A1 Apr. 12, 2018

Related U.S. Application Data

(60) Provisional application No. 62/162,901, filed on May 18, 2015.

(51) Int. Cl.
| | |
|---|---|
| *G01N 33/48* | (2006.01) |
| *G16B 40/00* | (2019.01) |
| *G01N 33/68* | (2006.01) |
| *G01N 33/50* | (2006.01) |
| *C12P 21/00* | (2006.01) |
| *G16C 20/60* | (2019.01) |
| *G16B 5/20* | (2019.01) |
| *G16B 35/10* | (2019.01) |
| *G16H 50/50* | (2018.01) |
| *G06N 7/08* | (2006.01) |

(52) U.S. Cl.
CPC ............ *G16B 40/00* (2019.02); *C12P 21/005* (2013.01); *G01N 33/50* (2013.01); *G01N 33/68* (2013.01); *G06N 7/08* (2013.01); *G16B 5/20* (2019.02); *G16B 35/10* (2019.02); *G16C 20/60* (2019.02); *G16H 50/50* (2018.01); *Y02A 90/10* (2018.01)

(58) Field of Classification Search
None
See application file for complete search history.

(56) References Cited

U.S. PATENT DOCUMENTS

| | | | |
|---|---|---|---|
| 2003/0233197 A1 | 12/2003 | Padilla et al. | |
| 2004/0133355 A1 | 7/2004 | Schneider | |
| 2007/0016390 A1 | 1/2007 | Bernardo et al. | |
| 2009/0259451 A1 | 10/2009 | Senger et al. | |
| 2010/0196940 A1* | 8/2010 | Collins ............... | G01N 33/5308 435/23 |
| 2011/0117601 A1* | 5/2011 | Haberger ........... | C07K 16/2866 435/69.6 |
| 2016/0160270 A1* | 6/2016 | Herrgard ................ | G16B 30/00 506/8 |

FOREIGN PATENT DOCUMENTS

WO     2015/010088 A1     1/2015

OTHER PUBLICATIONS

Sánchez-Rodriguez, Aminael, et al. "A network-based approach to identify substrate classes of bacterial glycosyltransferases." BMC genomics 15.1 (2014): 1-21.*
Spahn, Philipp N., et al. "A novel low-parameter computational model to aid in-silico glycoengineering." BMC Proceedings. vol. 9. No. 9. BioMed Central, 2015.*
Spahn, Philipp N., et al. "A Markov chain model for N-linked protein glycosylation—towards a low-parameter tool for model-driven glycoengineering." Metabolic engineering 33 (2016): 52-66.*
Wiback, Sharon J., et al. "Monte Carlo sampling can be used to determine the size and shape of the steady-state flux space." Journal of theoretical biology 228.4 (2004): 437-447.*
Ueda, Nobuhisa, et al. "A probabilistic model for mining labeled ordered trees: capturing patterns in carbohydrate sugar chains." IEEE Transactions on Knowledge and Data Engineering 17.8 (2005): 1051-1064.*
Liu, Gang, Apurv Puri, and Sriram Neelamegham. "Glycosylation Network Analysis Toolbox: a MATLAB-based environment for systems glycobiology." Bioinformatics 29.3 (2013): 404-406.*
Kaveh, Ohadi, et al. "Novel dynamic model to predict the glycosylation pattern of monoclonal antibodies from extracellular cell culture conditions." IFAC Proceedings vols. 46.31 (2013): 30-35.*
PCT International Search Report and Written Opinion for PCT Application No. PCT/US2016/033136 dated Sep. 7, 2016 (8 pages).
Jedrzejewski et al., "Towards Controlling the Glycoform: A Model Framework Linking Extracellular Metabolites to Antibody Glycosylation," Int. J. Mol. Sci., 2014, 15:4492-4522.
Spahn et al., "A Novel Low-Parameter Computational Model to Aid in-silico Glycoengineering," BMC Proceedings, 2015, 9(Suppl. 9):p. 26:1-3.
European Search Report for EP Application No. 16797239.7 dated May 3, 2019 (20 pages).

(Continued)

*Primary Examiner* — Anna Skibinsky
(74) *Attorney, Agent, or Firm* — Workman Nydegger

(57) ABSTRACT

The disclosed technology provides a computational prediction modeling comprising a novel algorithm for prediction of glycosylation or to optimize biopharmaceutical production of proteins of therapeutic relevance. The model of the disclosed technology can be used to predict glycosylation changes based solely on the stating glycoprofiles in any host cells and known or suggested rules on enzyme specificity. Applications of the invention model are also provided.

21 Claims, 43 Drawing Sheets

(56) References Cited

OTHER PUBLICATIONS

Megchelenbrink et al., "optGpSampler: An Improved Tool for Uniformly Sampling the Solution-Space of Genome-Scale Metabolic Networks," PLOS One, 2014, 9(2):e86587 (8 pages).
Orth et al., "What is Flux Balance Analysis?," Nat. Biotechnol., 2010,28(3):245-248.
Spahn et al., "A Markov Chain Model for N-Linked Protein Glycosylation—Towards a Low-Parameter Tool for Model-Driven Glycoengineering," Metab. Eng., 2015, 33:52-66.
Wang et al., "Metabolic Control Analysis under Uncertainty: Framework Development and Case Studies," Biophysical Journal, 2004, 87:3750-3763.

* cited by examiner

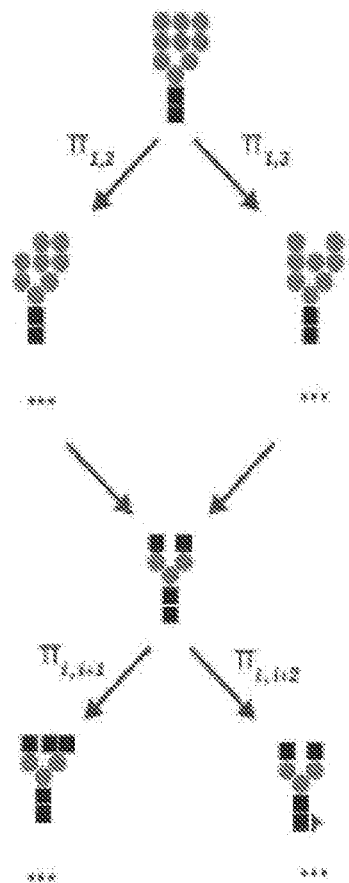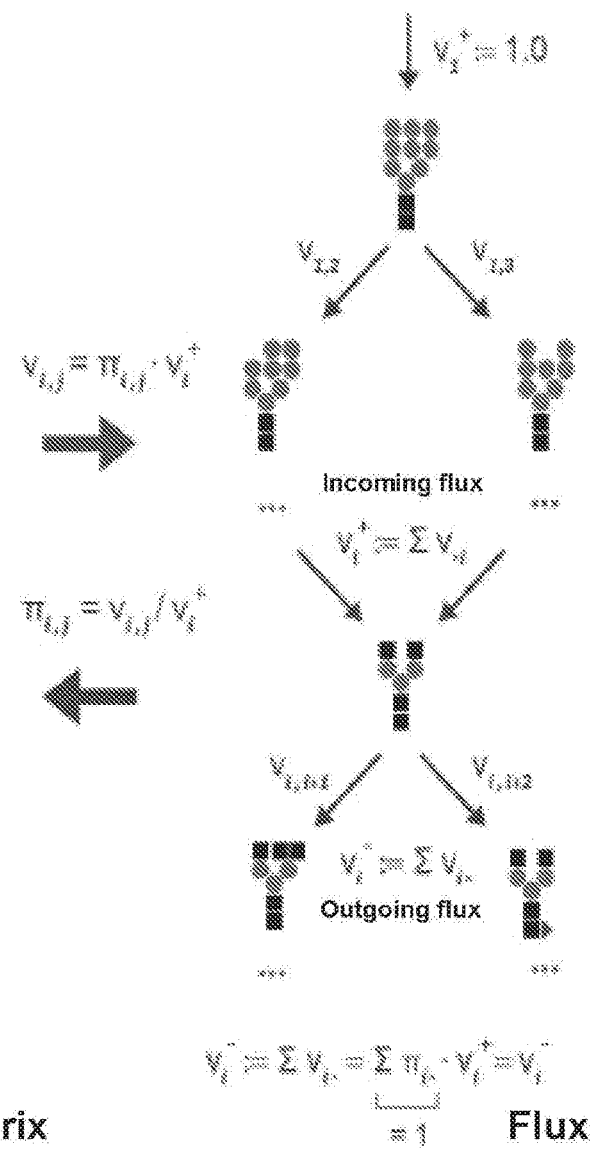
FIG. 8

1. Identify reactions affected by enzyme knock-down
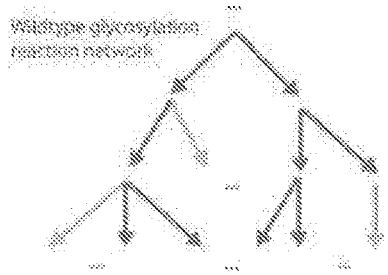
Example:
Fucosylation
2. Scale down affected transition probabilities
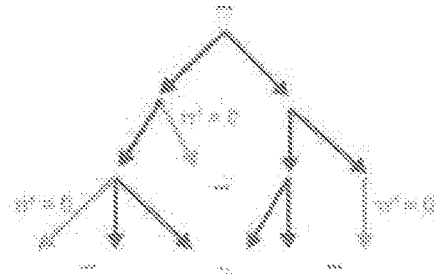
Example:
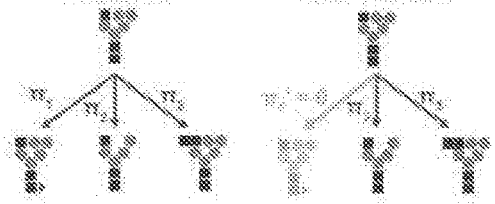
Wildtype      Knock-down
3. Adjust alternative transition probabilities
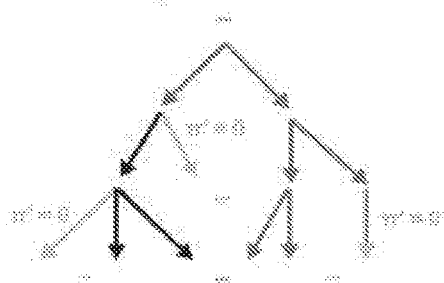
Example:
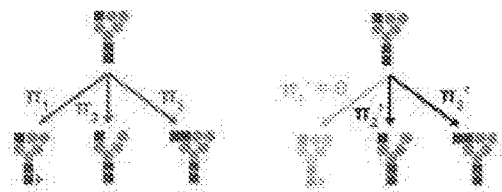
Wildtype      Knock-down
4. Add transport/secretion reaction in case of absence of alternative reactions
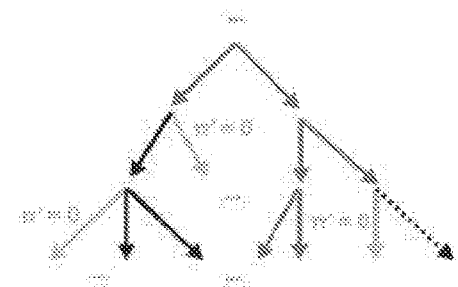
Example:
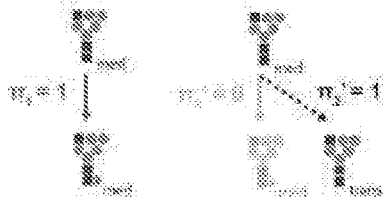
Wildtype      Knock-down
FIG. 9 sugar nucleotide metabolism
COBRA model
glycosylation
Markov model
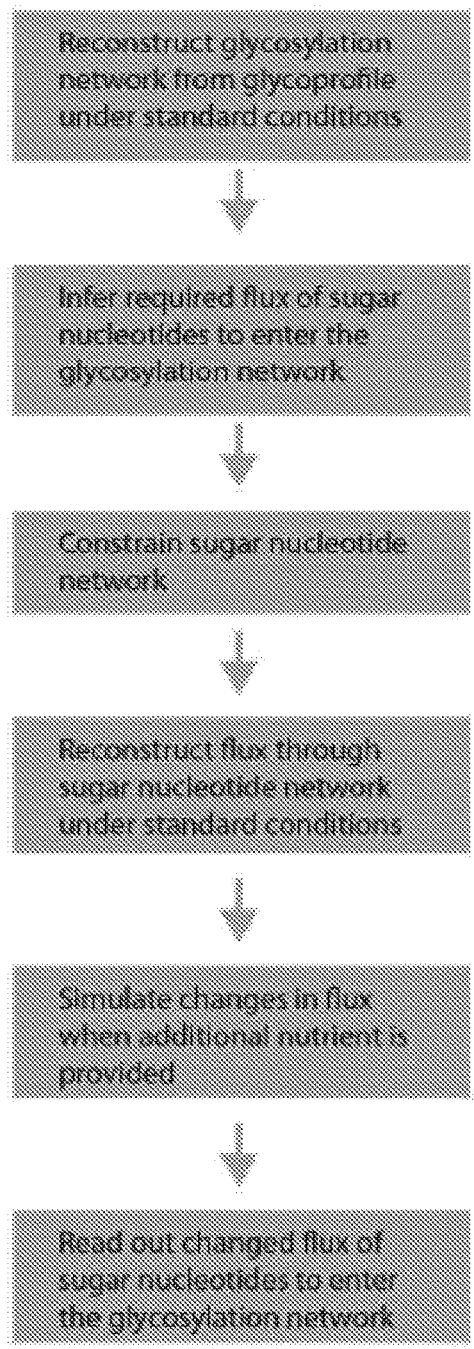
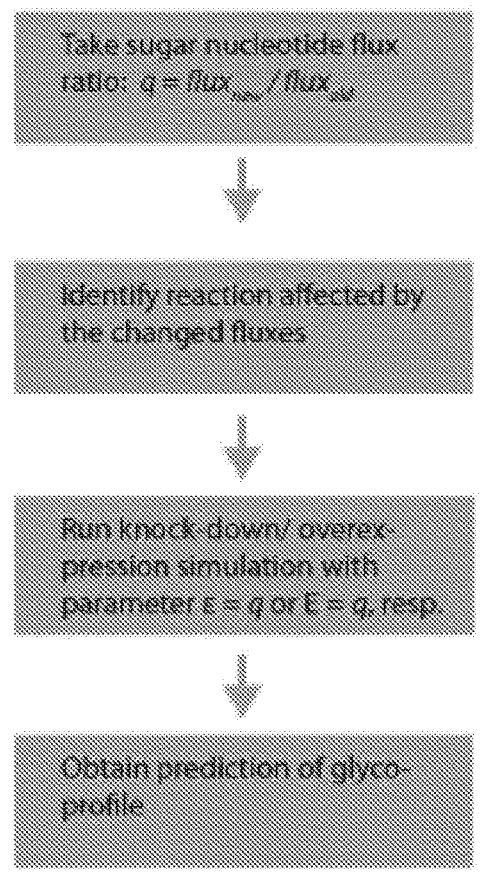
FIG. 14

Start distribution
(Initial glycan)
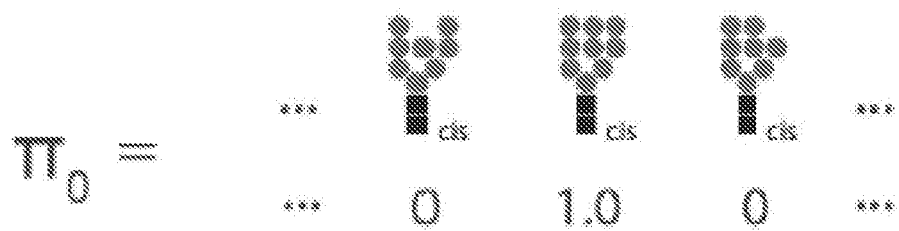
Absorbing states
(Glycan secretion)
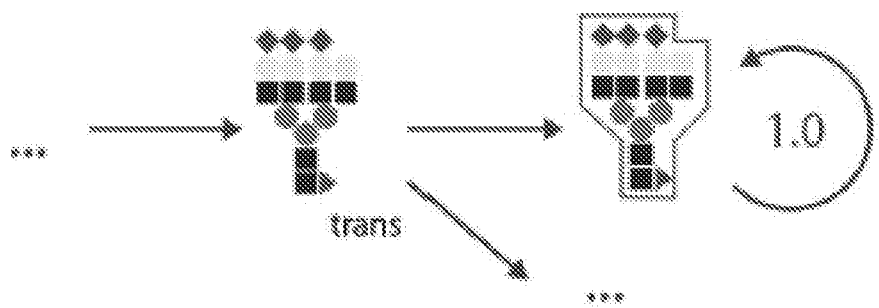
FIG. 16

SYSTEMS AND METHODS FOR PREDICTING GLYCOSYLATION ON PROTEINS

CROSS REFERENCE TO RELATED APPLICATIONS

This application claims the priority benefit of PCT/US2016/033136 filed on May 18, 2016 which claims priority to a U.S. Provisional Patent Application No. 62/162,901, filed May 18, 2015. The entire contents of which are hereby incorporated by reference.

FIELD OF THE INVENTION

Aspects of the invention are generally related to rational engineering of bio-industrial cell culture conditions. More specifically, to the utilization of computational tools to optimize biopharmaceutical production of proteins of therapeutic relevance.

BACKGROUND OF THE INVENTION

Therapeutic proteins are increasingly important to the pharmaceutical industry. Global spending on therapeutic proteins, such as antibodies, hormones and blood factors, reached $138 billion dollars in 2010. Most of these proteins are glycoproteins, i.e. they become modified in the cell through additions of sugar chains (glycans). Several classes of these glycan modifications exist which differ by the nature of their chemical linkage. In particular, modifications with so-called N-glycans confer chemical properties that are critical for the protein's biological function and, thus, for their therapeutic efficacy and biosafety. Consequently, it is of paramount importance for industrial production of these proteins to control their N-glycan modification.

Unfortunately, unlike protein synthesis which follows a DNA template and is, thus, readily amenable to rational engineering, N-glycosylation (i.e. the process in which N-glycans are added to the protein in the cell) occurs in a non-template-based, stochastic fashion. This is also true for all other forms of glycan, such as O-glycans, glycolipids, glucosaminoglycans, milk oligosaccharides, etc. A series of enzymes will add sugar moieties to the growing glycan chain, dependent on a complex interplay of various influencing factors. These factors include, among others, the expression level of these enzymes, the availability of the reaction components involved, as well as the steric constraints in the interactions of these enzymes with the particular glycoprotein. As a result of this complexity, the N-glycan modifications on a glycoprotein or the structure of any glycan typically follow a statistical distribution—a so-called glycoprofile. This glycoprofile is specific for a certain glycoprotein, glycolipid, or any other biological sample in the sense that it displays a reproducible range of certain glycans, but the quantitative fraction of each glycan may vary between different cell lines or process conditions, protein, lipid, or biological sample. Controlling this glycoprofile during production is a critical quality requirement since certain glycans are crucial for certain physiological parameters of a glycoprotein, such as binding affinity or turn-over, and thus proper glycans represent a critical product quality. Glycoprofile control also plays a major role in the manufacturing of biosimilars (biomolecules that are copies of an existing product but are marketed by a different company) as the glycoprofile of the original product is part of the approved drug and, thus, needs to be precisely reproduced along with the protein itself.

Given this importance, glycosylation control represents a major challenge in biopharmaceutical protein production or the development of other therapeutics involving glycans and numerous strategies have been proposed to adjust process conditions towards certain desired glycoprofiles. Most of these strategies involve (i) genetic modification of the host cell line or (ii) chemical changes to the nutrient supplementation in the growth medium. Largely, however, these adjustments have relied on sophisticated guesses and trial-and-error experimentation. In an attempt to allow a more rational approach towards the development of these adjustment strategies, a number of computational approaches have been proposed in recent years that aim at the in-silicon prediction of glycosylation through the utilization of mathematical models. While these models have shown a great potential in aiding the understanding of the complex mechanisms driving glycosylation, most of them rely on numerous model parameters that are usually not available or hard to obtain.

SUMMARY OF THE INVENTION

The invention comprises an algorithm that allows the prediction of how changes in mammalian cell culture conditions (genetic changes in the cell line or chemical changes in the growth medium) affect the profile of glycans, including but not limited to N-glycans on proteins produced from that cell line. The method requires measurements of the N-N-glycan profile, e.g., N-glycans, O-glycans, milk oligosaccharides, glucosaminoglycans, etc., taken from a wild-type cell line as a calibration standard. Subsequently, it reconstructs the biochemical reaction network that leads to the observed profile and transforms it into a stochastic framework (a Markov chain). It then utilizes probability-based computation to predict how the reaction network would react to genetic changes of the host or nutritional changes in media conditions. It produces a predicted glycan profile, backed up with statistical assessments of error margins in individual glycan frequencies.

As an example, the biochemistry of the N-glycosylation reaction network has been thoroughly studied. In particular, the participating enzymes are well characterized with regard to their reaction specificities, i.e. the glycan substrates they operate on as well as their reaction constraints, e.g. glycan epitopes that prevent their reaction despite the substrate being present (Table 1). For most enzymes, their intracellular localization is also well known. Thus their place of action within the reaction hierarchy is well defined. The process of N-glycosylation always starts with the same initial structure (the $Man_9GlcNAc_2$ glycan), and with the rule set of all enzymes known, the algorithm successively generates all glycans that can be synthesized in theory by the combined action of the glycosylation enzymes (FIG. 1). This yields a generic reaction network, capable of creating tens of thousands of glycan structures (FIGS. 2,3).

TABLE 1

Enzymes and reaction rules implemented in the model

| Enzyme | Substrate | Product | Constraint | Localization |
|---|---|---|---|---|
| Man I | (Ma2Ma | (Ma | — | cis |
| GnT I | (Ma3(Ma3(Ma6)Ma6)Mb4 | (GNb4Ma3(Ma3(Ma6)Ma6)Mb4 | — | cis |

TABLE 1-continued

Enzymes and reaction rules implemented in the model

| Enzyme | Substrate | Product | Constraint | Localization |
|---|---|---|---|---|
| Man II | (Ma3(Ma6)Ma6 | (Ma6Ma6 | (GNb2\|Ma3 | medial |
| Man II | (Ma6Ma6 | (Ma6 | (GNb2\|Ma3 | medial |
| GnT II | (Gnb2\|Ma3(Ma6)Mb4 | (GNb2\|Ma3(GNb2Ma6)Mb4 | — | medial |
| a6FucT | GNb4GN | GNb4(Fa6)GN | GNb2\|Ma3 | medial |
| GnT IV | (GNb2Ma3 | (GNb2(GNb4)Ma3 | — | medial |
| GnT V | (GNb2Ma6 | (GNb2(GNb6)Ma6 | — | trans |
| b4GalT | (GN | (Ab4GN | — | trans |
| iGnT | (Ab4GN | (GNb3Ab4GN | ~*...Ma3 | trans |
| a6SiaT | (Ab4GN | (NNa3GNb3Ab4GN | — | trans |

KEY:
... = Continuation, i.e. any string (possibly empty) with all parentheses matched
| = Possible branch point, i.e. empty string or (...)

Since this network generates all theoretically possible glycans, it represents a mere repository rather than a model for the reaction network in a specific protein-producing cell line. In order to infer the specific reaction network that underlies the glycosylation of a particular protein produced, the information from the measured glycoprofile on this protein (submitted by the user) (FIG. 4) is leveraged to tailor the generic network to the specific profile by identifying all reactions that are not required to obtain the glycans occurring in this profile. These are then removed from the network, leaving the minimal reaction network required to produce the measured profile. This method of "model reduction" is part of the constraints-based modeling and reconstruction (COBRA) toolbox that provides tools of linear optimization for analysis of biochemical reaction networks. After tailoring the network, there usually remains a large ambiguity of how paths through this network lead from the start point of the network (e.g., for N-glycosylatoin, the initial $Man_9GlcNAc_2$ glycan) to the end-point (the observed glycoprofile) (FIG. 5). This variance in reaction flux can be assessed through Monte-Carlo sampling as implemented in the optGpSampler tool (FIG. 6) or other algorithms that produce one or more flux vectors.

The reaction fluxes between glycans in the network, along with their variances, are re-formulated as probabilities to move from one glycan to another (FIG. 7)—a transformation that is possible because the total flux through the glycosylation network is normalized to 1, and the incoming flux into each glycan equals the outgoing flux in the reaction network as it relies on a steady-state hypothesis (FIG. 8). This re-formulation allows transformation of the reaction network into a Markov chain, a well-studied class of stochastic processes, granting access to simulation of glycosylation in a probabilistic framework.

To simulate how perturbation in the reaction network affects the produced glycoprofile, the reconstructed Markov chain is modified in order to account for the manipulation to be simulated.

In order to simulate a decrease in enzyme activity (a "knock-down" or "knock-out"), the algorithm first identifies all reactions in the network that depend on the respective enzyme (FIG. 9, step 1). The probabilities for reactions that depend on the enzyme are then scaled down by a factor c (specified by the user) (FIG. 9, step 2). Since probabilities to transition to other glycans must add up to 1, these modifications require that the remaining probabilities from the respective glycan be adjusted as a consequence of the perturbation (FIG. 9, step 3). These adjustments are obtained in a way as to maintain the reaction probability ratios among competing reactions under the constraint of the applied perturbation. Apart from these modifications, all other reaction probabilities remain unchanged. With these modifications, the Markov chain is re-run to predict how flux through the reaction network now leads to an altered glycoprofile.

In case of an upregulation of enzyme activity ("overexpression"), the procedure is analogous to a), except that affected reaction probabilities are scaled up by a factor E (>1), instead (FIG. 10).

Knock-downs of a set of one or more enzymes and simultaneous overexpression of a different set of one or more enzymes, the procedures FIGS. 9,10) re carried out one at a time under the assumption of independence.

The workflow in FIG. 9 can be reversed by utilizing a glycoprofile obtained under perturbed conditions rather than predicting it. The sequential action of glycosylation enzymes on the growing glycan chain occurs through differential localization of these enzymes to different compartments of the Golgi. Knowledge on enzyme localization is of relevance since co-localized enzymes compete for the same substrates. Thus, different assumptions on enzyme localization considerably impact reaction network topology. Although the biochemistry of many glycosylation enzymes are well characterized (especially for N-linked glycosylation), their subcellular localization has not been studied with the same scrutiny. To test the validity of certain hypotheses regarding the physical localization of certain glycosylation enzymes, the algorithm compares simulated glycoprofiles with observed glycoprofiles to assess which hypothesis yields predictions that are in congruence with the experimental data. Alternative localization hypotheses imply different reaction topologies and thus different reaction rule sets. Using either of these alternative reaction topologies, alternative reaction networks are reconstructed when tailoring the generic network to a glycoprofile from a standard cell line. Simulation of a perturbation is carried out for each alternative reconstruction separately and, given experimental data of a perturbation is available, the consistency of the underlying localization hypothesis can be assessed by the congruence of the experimental data with each of the obtained predictions.

Similarly, the workflow from FIG. 9 can be reversed in order to analyze changes in the glycosylation reaction network based on observed glycopatterns from a perturbed condition. Congenital disorders of glycosylation are caused by genetic defects leading to aberrant glycosylation, with potentially severe physiological and developmental consequences. Apart from the observable aberrant glycoprofiles of the patient, the genetic basis of many conditions are unknown, and it is thus unknown what kind of perturbation in the reaction network actually lead to the aberrant glycopatterns. Starting from a hypothetical perturbation (such as a knock-down of one or more enzymes), the algorithm computes a predicted glycoprofile and quantifies the fit of the predicted aberrant profile with the observed profile from the patient. It then utilizes a genetic algorithm to randomly change the assumed perturbation to move the predicted profile as close to the observed profile as possible. The endpoint of this optimization process reveals which perturbation of the glycosylation reaction network shows the highest congruence to the observable data (FIG. 11).

Perturbations of the glycosylation reaction network can also occur by changing the concentrations (and thus the availability) of required reaction precursors rather than by changing the expression levels of the enzymes involved. In order to simulate such chemical changes, the Markov chain model is linked to a reaction network describing the metabolic pathways of the cells and the transport of metabolites in and out of the cells. This could include all metabolic reactions in the cell or more direct enumeration of the reactions underlaying sugar nucleotide metabolism in the cell since sugar nucleotides represent the chemical species that function as precursors for all glycosylation reactions (FIG. 12). Starting from an observed glycoprofile, the quantitative requirements (fluxes) of each of these sugar nucleotide precursors can be uniquely reconstructed during the tailoring procedure. These reconstructed fluxes are then used to reconstruct the flux through the sugar nucleotide metabolic network starting from the nutrients (e.g. glucose, glutamine) provided in the growth medium. Supplementation with additional nutrients leads to perturbations in these metabolic fluxes which can be simulated using methods from the COBRA toolbox or other software for constraint-based modeling, linear optimization or techniques in convex analysis. The resulting changes in the sugar nucleotide fluxes are then related to the standard condition, and their ratio (perturbed/standard) is taken as a factor to alter the probabilities of glycosylation reactions depending on these precursors (FIG. 13). From here on, the method illustrated in FIG. 14 are carried out, depending on whether the ratio indicates a decrease or increase in reaction probability or a mixture or both. As in FIG. 9, re-running the Markov chain with these adjusted probabilities yields a prediction of how the glycoprofile changes in response to the changes in supplementation.

These and other aspects of the present invention will be apparent to those of ordinary skill in the art in the following description, claims and drawings.

BRIEF DESCRIPTION OF THE DRAWINGS

This patent application file contains no drawings executed in color.

FIG. 8. Transformation into a stochastic framework (II). The assumption of a steady-state of metabolite concentrations (one of the key axioms in the COBRA modeling framework) allows the transformation into a stochastic framework as it implies that probabilities sum up to 1 for each glycan. The transformation works vice-versa making the stochastic and the flux formulation equivalent.

FIG. 9. Modeling enzyme knock-downs. Step 1: All reactions in the wildtype glycosylation reaction catalyzed by the enzyme(s) to be knocked down (e.g. the fucosyltransferase) are identified. Step 2: The transition probabilities of these reactions are then scaled down. To model a complete knock-out, they are set to 0 as illustrated here. Step 3: The transition probabilities of alternative reactions, i.e. those taking the same glycan substrate as the one being knocked down (black arrows), need to be adjusted to maintain a probability sum of 1 for each glycan in the network. Step 4: If no alternative reactions exist, it is assumed that the glycan will leave the corresponding Golgi compartment unmodified and transition into the next compartment or becomes secreted (if already in the trans Golgi). For clarity, localization labels on glycans have been omitted in the remaining cartoons. All other transition probabilities remain identical to the wildtype network.

FIG. 14. Flowchart illustrating a method according to the present disclosure.

FIG. 16. The start distribution $\pi_0$ of the chain mirrors the initialization of N-glycosylation and is, thus, concentrated on the $Man_9GlcNAc_2$ glycan. Glycans that are to be secreted can transition into an artificial absorbing state (framed glycan) which transitions to itself with probability 1 in every step, leading to absorption of the chain.

(FIG. 20B)

DETAILED DESCRIPTION OF THE INVENTION

Figure 1:
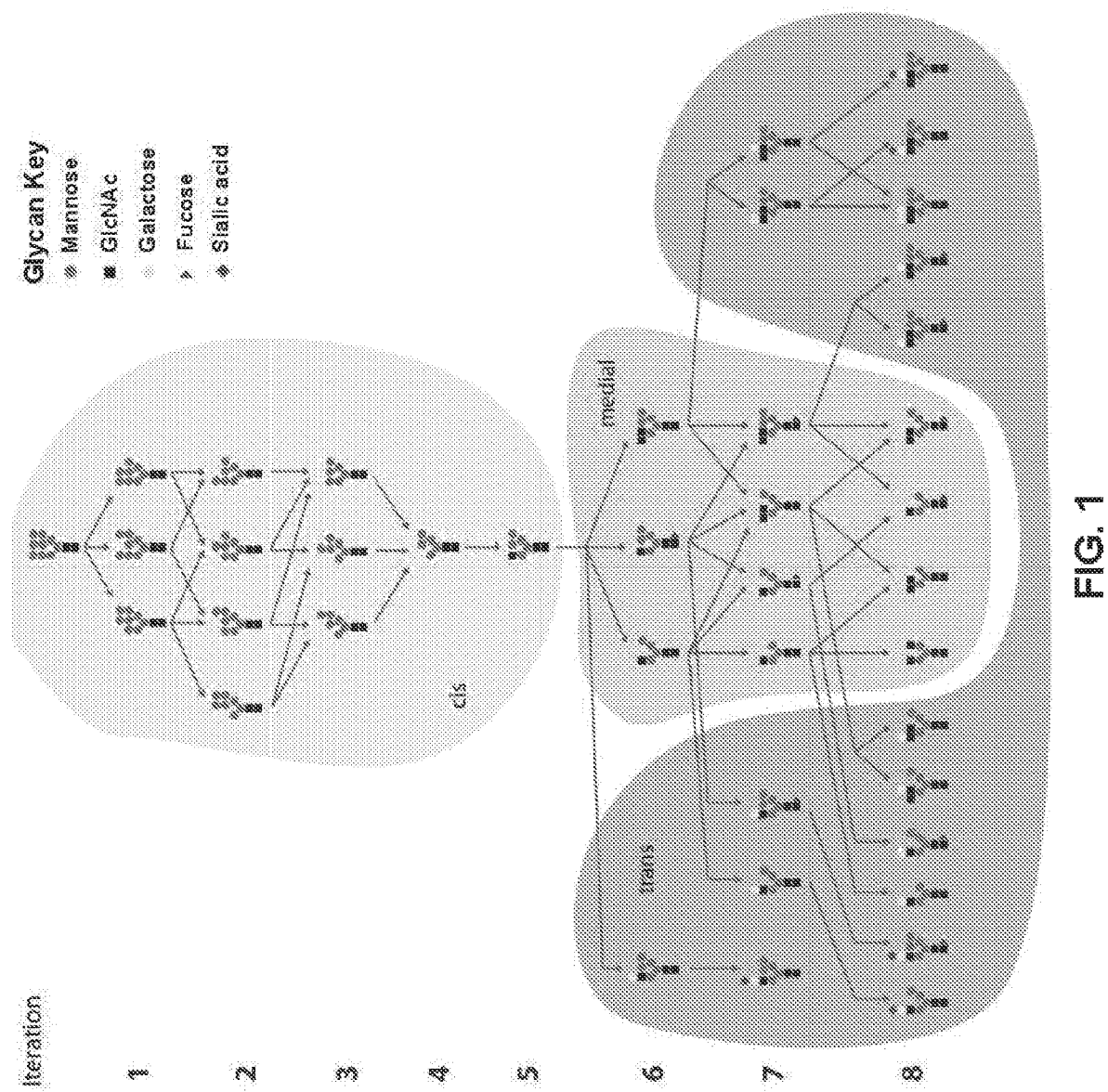
FIG. 1. Generation of a generic glycosylation reaction network (I): Diagram outlining the first 8 iterations of the generating algorithm following the rule set for N-glycosylation in Table 1. The Golgi apparatus is modeled with three compartments (cis, medial and trans). Secretion reactions are omitted in the figure for clarity, but are included in the computational model.
Figure 2:
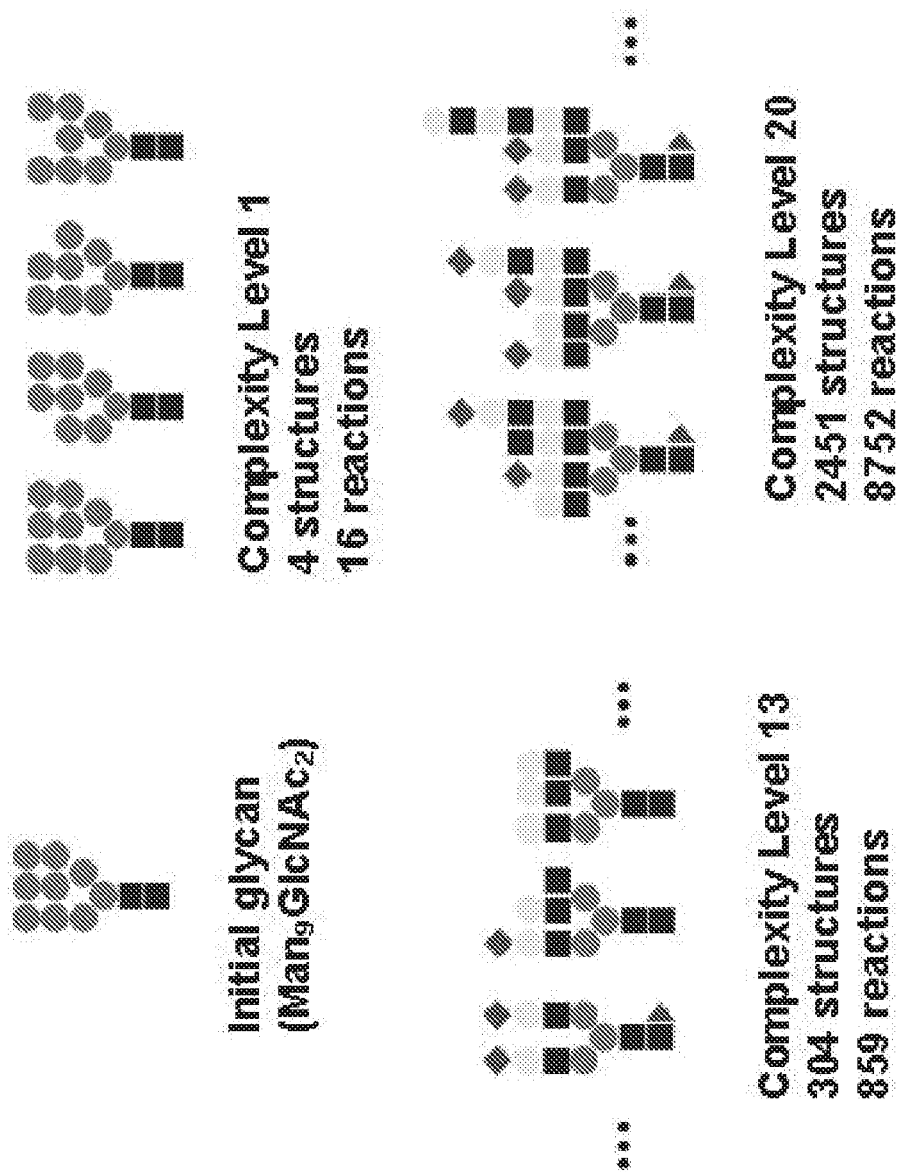
FIG. 2. Generation of a generic glycosylation reaction network for N-linked glycosylation (II): Starting in the initial $Man_9GlcNAc_2$ glycan, an iterative application of the reaction rules in Table 1 generates the generic N-glycosylation reaction network. "Complexity level" refers to the number of iterations of the generating algorithm.
Figure 3:
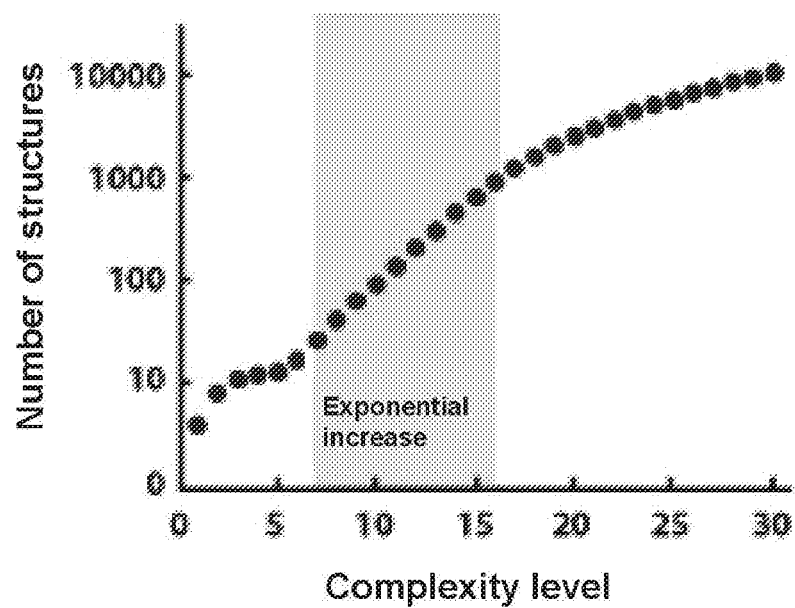
FIG. 3. The number of possible glycans shows an exponential increase before leveling off.
Figure 4:
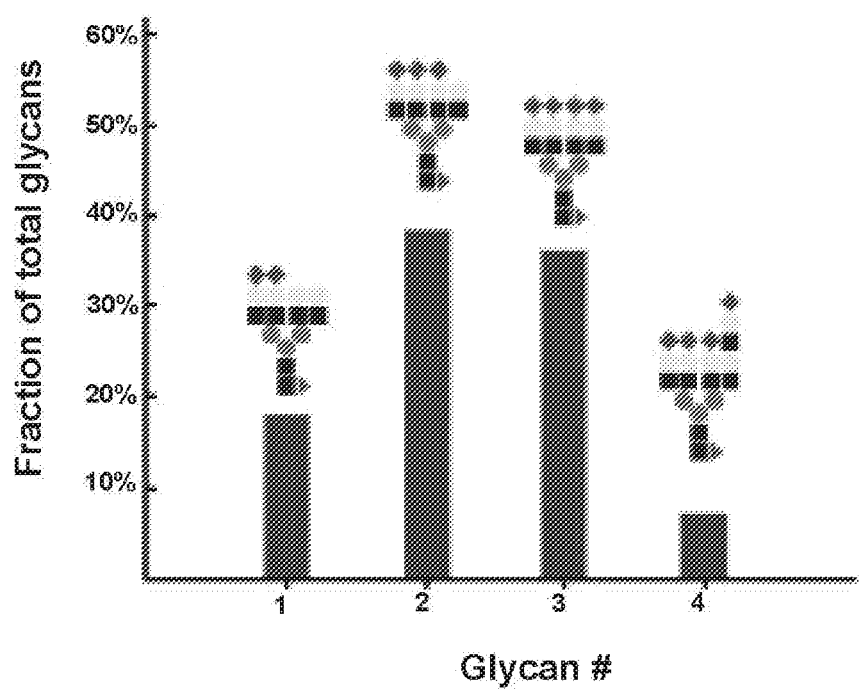
FIG. 4. N-glycoprofile: N-glycans retrieved from erythropoietin produced in a CHO cell line (Data from (Yang et al., 2015)).
Figure 5:
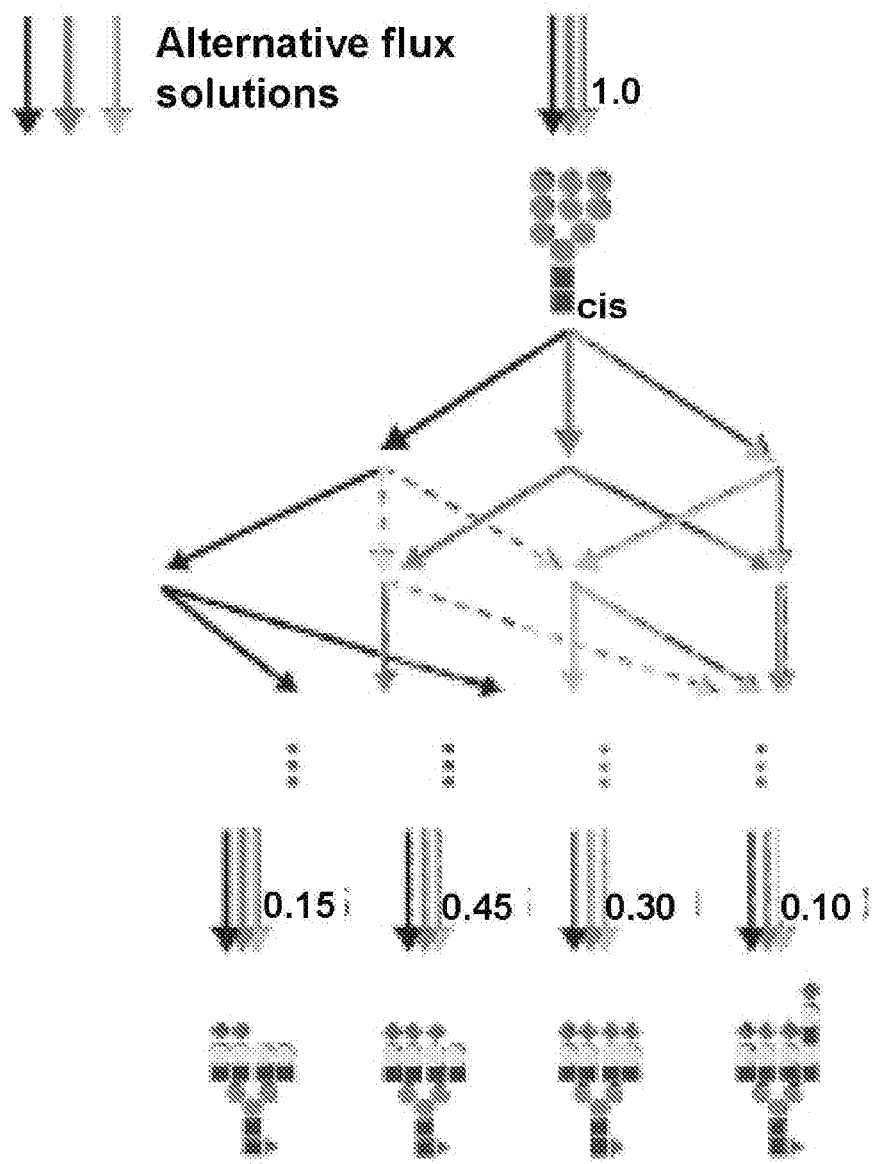
FIG. 5. Variance in flux. Usually the flux that links the initial glycan to the final glycan profile is not unique (i.e., there are multiple pathways that can be taken to make a glycan). Mathematically, the entirety of these fluxes represent a subset of a high-dimensional plane that can be explored through uniform sampling.
Figure 6:
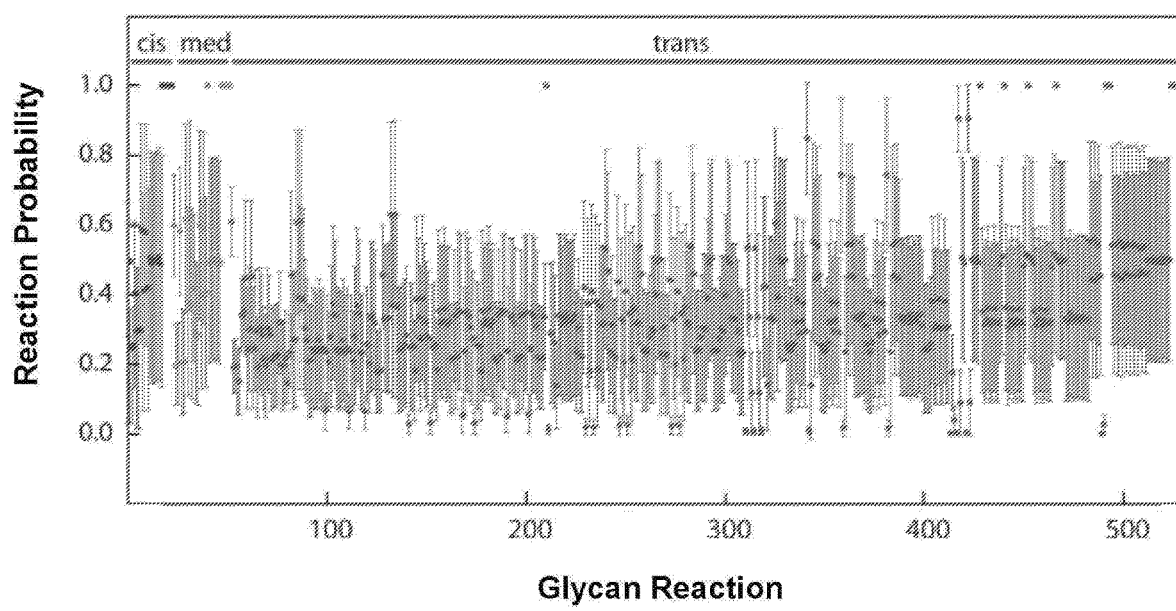
FIG. 6. Sampling results. After Monte-Carlo sampling, the mean flux and standard deviation is plotted for each reaction in the tailored network. Fluxes are represented after transformation into probabilities (FIG. 8).

Unless defined otherwise, all technical and scientific terms used herein have the same meaning as commonly understood by one of ordinary skill in the art to which the invention pertains. Other specifically defined terms are to be construed in a manner consistent with the definition provided herein. Although any methods and materials similar or equivalent to those described herein can be used in the practice for testing of the present invention, the preferred materials and methods are described herein. In describing and claiming the present invention, the following terminology will be used.

As used in this specification and the appended claims, the singular forms "a", "an" and "the" include plural referents unless the content clearly dictates otherwise. Thus, for example, reference to "a construct" includes a combination of two or more nucleic acid constructs, and the like.

The disclosed technology describes certain algorithm and process that allows the prediction of how changes in mammalian cell culture conditions (genetic changes in the cell line or chemical changes in the growth medium) affect the profile of glycans produced from that cell line. This applies to N-glycans on proteins, O-glycans, glucosaminoglycans, glycolipids, milk oligosaccharides, or other glycans. In some embodiments the method uses measurements of the N-glycan profile taken from a wildtype cell line as a calibration standard. (e.g., the N-glycans on a cell or protein or glycans in a biological fluid or sample). Subsequently, the disclosed technology can reconstruct the biochemical reaction network that leads to the observed profile and transforms it into a stochastic framework (a Markov chain). Further the disclosed technology can use probability-based computation to predict how the reaction network would react to genetic changes of the host or nutritional changes in media conditions. Further the disclosed technology can use a predicted glycan profile (e.g., N-glycan profile), backed up with statistical assessments of error margins in individual glycan frequencies.

The strength of the disclosed technology is its focus on industrial applicability and the omission of heavy parameterization. Instead, after the model has been calibrated with a glycoprofile from a standard cell line, protein product, or biological fluid or sample, no further parameter input is needed from the user to simulate how the profile would change if certain enzymatic reactions in glycosylation are perturbed, for instance through genetically up- or downregulating a set of enzymes or by altering the level of required reaction precursors. In addition, the disclosed technology provides further applications of this modeling framework, such as a method to test localization hypotheses of glycosylation enzymes in the cell as well as the identification of unknown gene mutations implied in congenital disorders of glycosylation or to identify enzymes catalyzing steps in glycan synthesis, or to find enzymatic steps regulating glycosylation.

Generation of the Generic Glycosylation Reaction Network

Generic glycosylation networks can be made for any type of glycosylation. In some embodiments, a generic N-linked glycosylation reaction network is created as a flux-balance reaction network (Palsson, 2015) and is using methods from the COBRA toolbox as implemented in MATLAB. First a set of 40 reactions is manually added to provide the initial $Man_9GlcNAc_2$glycan as well as all minor reaction components required for the glycosylation enzymes, such as water, phosphate and sugar nucleotides. Glycans are encoded as text strings in the LinearCode and are saved in a list (containing only the initial $Man_9GlcNAc_2$glycan at first), although any other glycan naming standard can be used (e.g., Iupac, glyde, etc.). Glycosylation enzymes add sugar moieties to existing glycans. The program, thus, iterates through a loop (where the maximal iteration limit is specified by the user) in which for each glycan in the current list, each of the 12 glycosylation enzymes uses a regular expression to find a substring on the glycan indicating a matching substrate. If found, the reaction is added to the reaction network and the new glycan is added to the list of glycans. In addition, every glycan in the list carries a localization tag as a terminal substring that indicates in which of the three Golgi sub-compartments (cis-, medial or trans-Golgi) it is localized. Therefore, when a matching substrate substring is found, the localization of the glycan must also match the localization of the enzyme in order for the reaction to take place. In addition to these enzymatic reactions, every newly generated glycan will imply the addition of a transport reaction of that glycan into another sub-compartment. Hereby, in this implementation, transports occur from cis to medial and from medial to trans-Golgi. However, compartments can be adjusted to the needs of the model or type of glycosylation. A glycan localized in the trans-Golgi triggers generation of an exit reaction mimicking its secretion. After finishing the iteration loop, the generic glycosylation reaction network is completed and saved as a COBRA file, although the network could be saved in any other format containing the network information. An alternative approach to the generation of a generic network involves the enumeration of all reactions that could be used to synthesize all measured glycans of a particular class, step by step.

Tailoring the Model to a Submitted Glycoprofile

The glycosylation reaction network created in the previous step contains all possible reactions and thus only represents a generic reaction repository. In order to model the glycosylation of a particular glycoprotein, this generic network needs to be tailored to make it specific. For this, the user provides a measured wildtype glycoprofile, i.e. a list of glycan strings together with their relative frequencies (These can be experimentally obtained, e.g. through mass spectrometry-coupled liquid chromatography (LC-MS)).

Since only the glycans provided in the profile are to be secreted, the program shuts down all secretion reactions in the generic network by constraining their flux to 0, except for the ones appearing in the profile. The fluxes for these are set to the specified frequencies (the flux into the initial $Man_9GlcNAc_2$ glycan is normalized to 1). The network is then tailored using model reduction through flux-variability analysis as part of the COBRA toolbox (Burgard et al., 2001; Gudmundsson and Thiele, 2010). This reduced network now represents the reaction topology that describes how flux from the initial $Man_9GlcNAc_2$ leads to the generation of the user-submitted glycoprofile although the path of this flux is not unique. The set of this usually very large space of possible fluxes can be sampled using Monte-Carlo methods, such as those described in (Megchelenbrink et al., 2014) or other related methods to sample a convex space, to obtain a representation of the entirety of possible fluxes. Sampling depth can be specified by the user, and in this example, a heuristic sampling statistic (Gelman and Rubin, 1992) is used to assess how comprehensively the set has been sampled, although other metrics can be used such as, but not limited to those described in Schellenberger, Lewis, Palsson, Biophysical Journal, 2011 and Schellenberger and Palsson, Journal of Biological Chemistry, 2009.

Transformation into a Markov Chain

Figure 15:
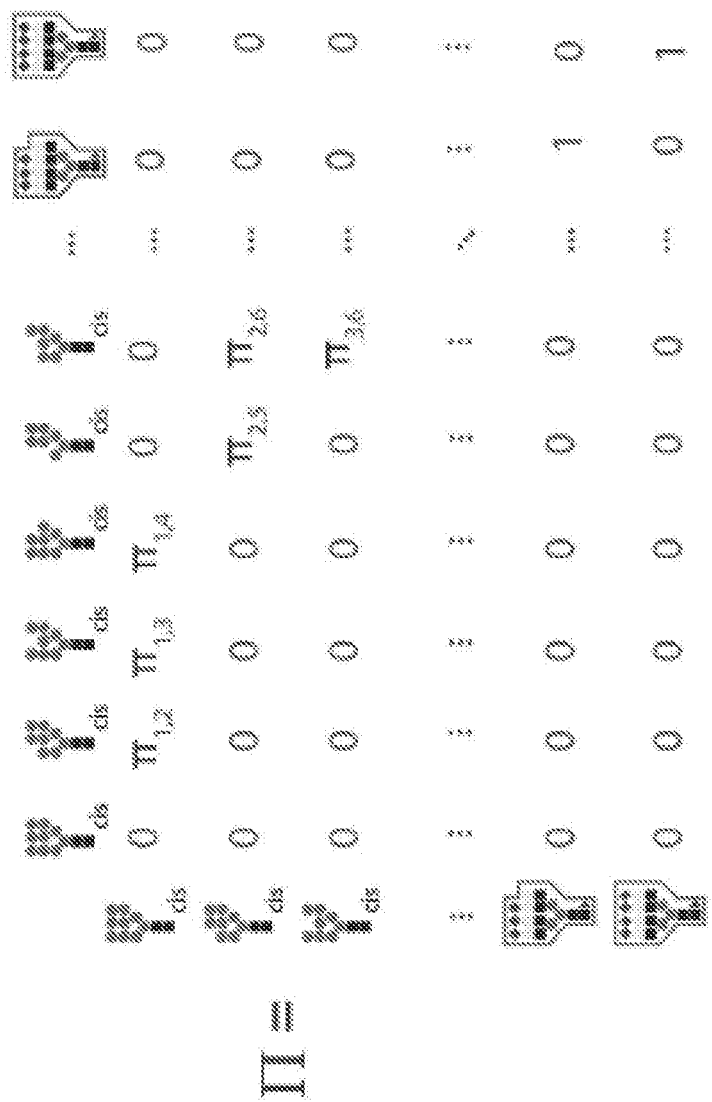
FIG. 15. Markov chain model of glycosylation. The transition matrix H comprises the probabilities of transitioning from each glycan (rows) to any other glycan (columns) in one reaction step. Glycan ordering and numbering is arbitrary.
Figure 17:
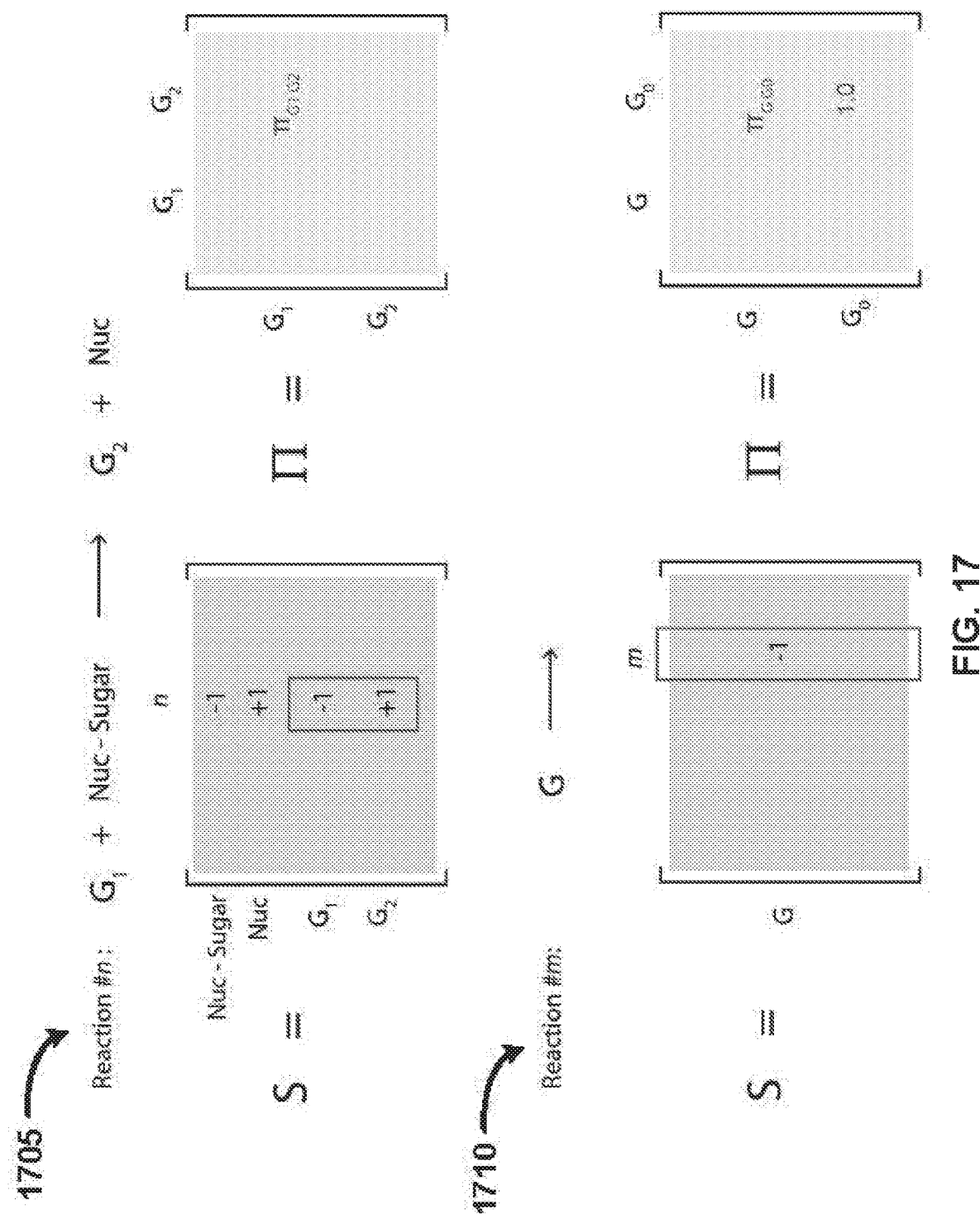
FIG. 17. Transformation of a COBRA model into a Markov transition matrix. As shown in 1705, COBRA reaction network is described by a stoichiometric matrix S with each column representing one reaction, each row representing one metabolite and the entries being the stoichiometric coefficients (Palsson, 2015). To transform S into a Markov transition matrix H, the algorithm identifies the possible transitions for every glycan in the network by finding the reactions in which this particular glycan ($G_1$) reacts to another one (e.g. $G_2$). A parameter for the (unknown) transition probability from $G_1$ to, e.g., $G_2$ is then introduced at the corresponding position in H. As shown in 1710, secretions are represented by secretion reactions in constraints-based modeling letting a glycan (G) be consumed without the production of another. In this case, the algorithm creates a new artificial absorbing state ($G_0$) in the Markov matrix to which G can transition. $G_0$ transitions to itself with probability 1. All entries in H not corresponding to a glycan reaction or secretion are 0.

In the next step, the reaction network is transformed into a Markov chain, i.e. every glycan in the network is regarded as a state in a stochastic network that can transition to others with a certain transition probability (FIG. 15). Glycan secretion is modeled as absorbing states, meaning states that transition to themselves with probability 1 (FIG. 16). The Markov transition matrix H describing this Markov chain is constructed by reading information from the reaction network. If a reaction is found that turns glycan $G_1$ into glycan $G_2$, a corresponding probability parameter is added in the transition matrix for the transition from $G_1$ to $G_2$ (FIG. 17). If a reaction is found that secrets a glycan, an absorbing state for that glycan is introduced, a probability parameter to the transition into that state is added, and the state is made absorbing by adding a probability of 1 for its transition to itself (FIG. 16). After setting up the Markov chain, its absorption probability describes the probability with which the chain reaches an absorbing state (starting in the initial $Man_9GlcNAc_2$) and is given by:

$$\pi_{abs} = \pi_{0|T'} \cdot (I - \Pi_T)^{-1} \cdot \Pi_{TA}$$

It can be shown that this formulation is equivalent to a flux-balance problem in the way that the absorption probabilities of the Markov chain equal the secretion fluxes in the flux-balance problem.

Figure 7:
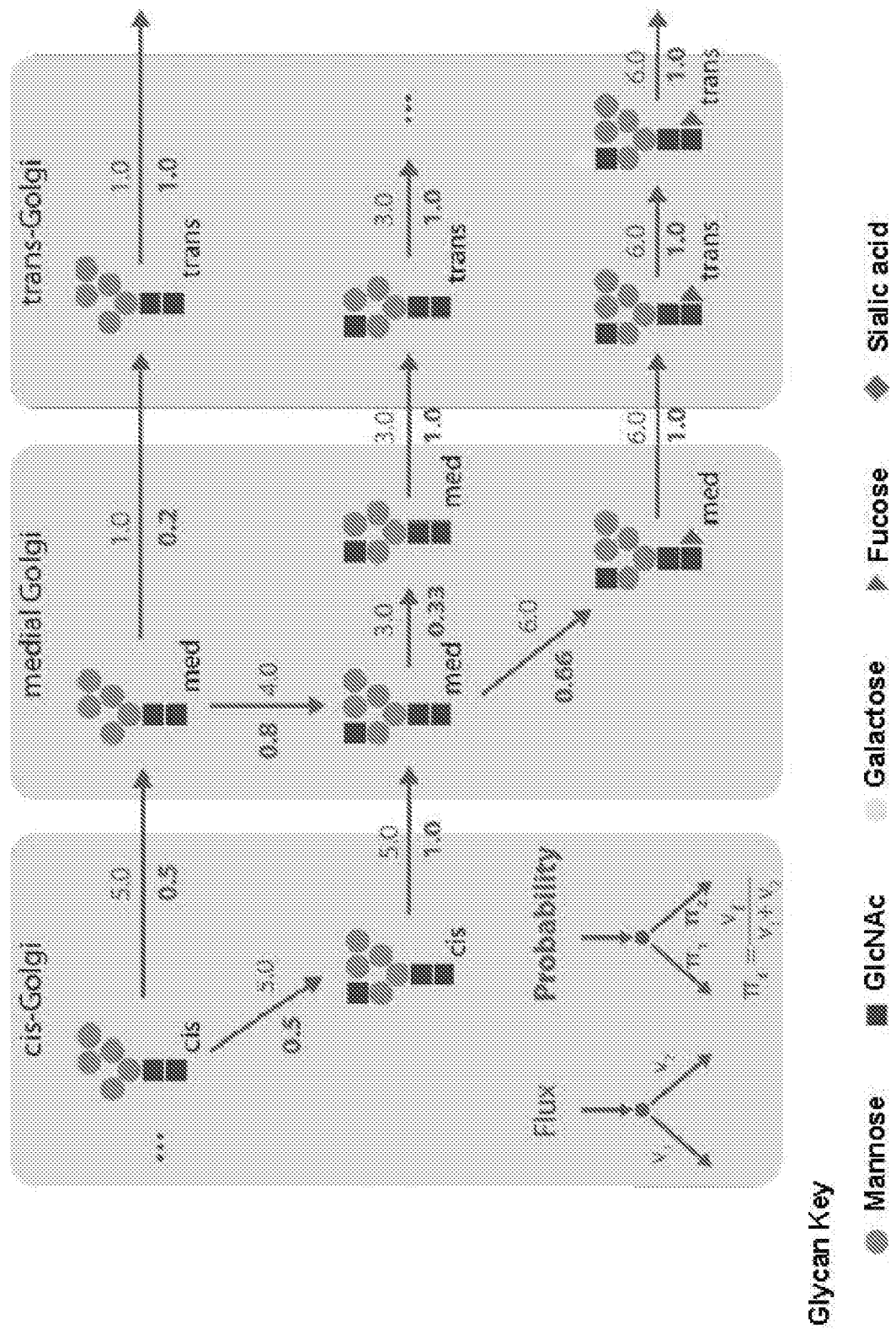
FIG. 7. Transformation into a stochastic framework (I). Fluxes through the reaction network are transformed into probabilities by taking flux ratios: Each flux is divided by the sum of all fluxes leaving a particular glycan.

The sampled fluxes generated in the previous step are transformed into transition probabilities by taking flux ratios. Thus, the transition probability from glycan $G_1$ to glycan $G_2$ is calculated by relating the flux from $G_1$ to $G_2$ to the total flux sum emanating from glycan $G_1$. That way, one flux through the reaction network from the initial $Man_9GlcNAc_2$ to the observed glycoprofile is transformed into a Markov transition matrix of reaction probabilities (FIG. 7; FIG. 8). Executing this transformation for every flux samples in the previous step yields an array of transition matrices, each of which describes how the glycoprofile is generated in a probabilistic way.

(a) Simulation of Perturbation in the Reaction Network: Enzyme Knock-Down

In order to simulate the knock-down of a glycosylation enzyme, the program first identifies all glycans in the network which react to another glycan in a reaction that requires the specified enzyme. For each of these glycans, the reaction probabilities have to be adjusted to simulate the knock-down situation. First, the probability of the affected reaction(s) is scaled down by a factor E ($0 \leq \epsilon < 1$) specified by the user, resulting in a new probability $\pi' = \epsilon \cdot \pi$ (FIG. 9, step 2). Subsequently, the remaining transition probabilities have to be adjusted to maintain a proper probability structure (reaction probabilities for every glycan need to sum up to 1 after the knock-down). For this, the program first counts the number of alternative reactions, i.e. reactions not dependent on the enzyme being knocked down. If there are no alternative reactions, it is assumed that, as a consequence of the knock-down, the glycan is transported into the next compartment with a probability of $1-\pi'$. In case of a knock-down in the trans Golgi the glycan would be secreted instead (FIG. 9, step 4).

If there are alternative reactions, their adjusted probabilities are calculated by maintaining their pairwise reaction probability ratios under the constraint that the total probability mass available to them has changed from $1-\pi$ to $1-\pi'$ (FIG. 9, step 3). These adjustments are carried out for the entire array of transition matrices.

As explained above, a knock-down may cause a glycan to be passed on into a compartment where it is not located in the wildtype network. Thus, this glycan now represents an "alien" in the new compartment for which there are no reactions present to process it. These "alien entries" are kept track of as they require special processing.

Figure 18A:
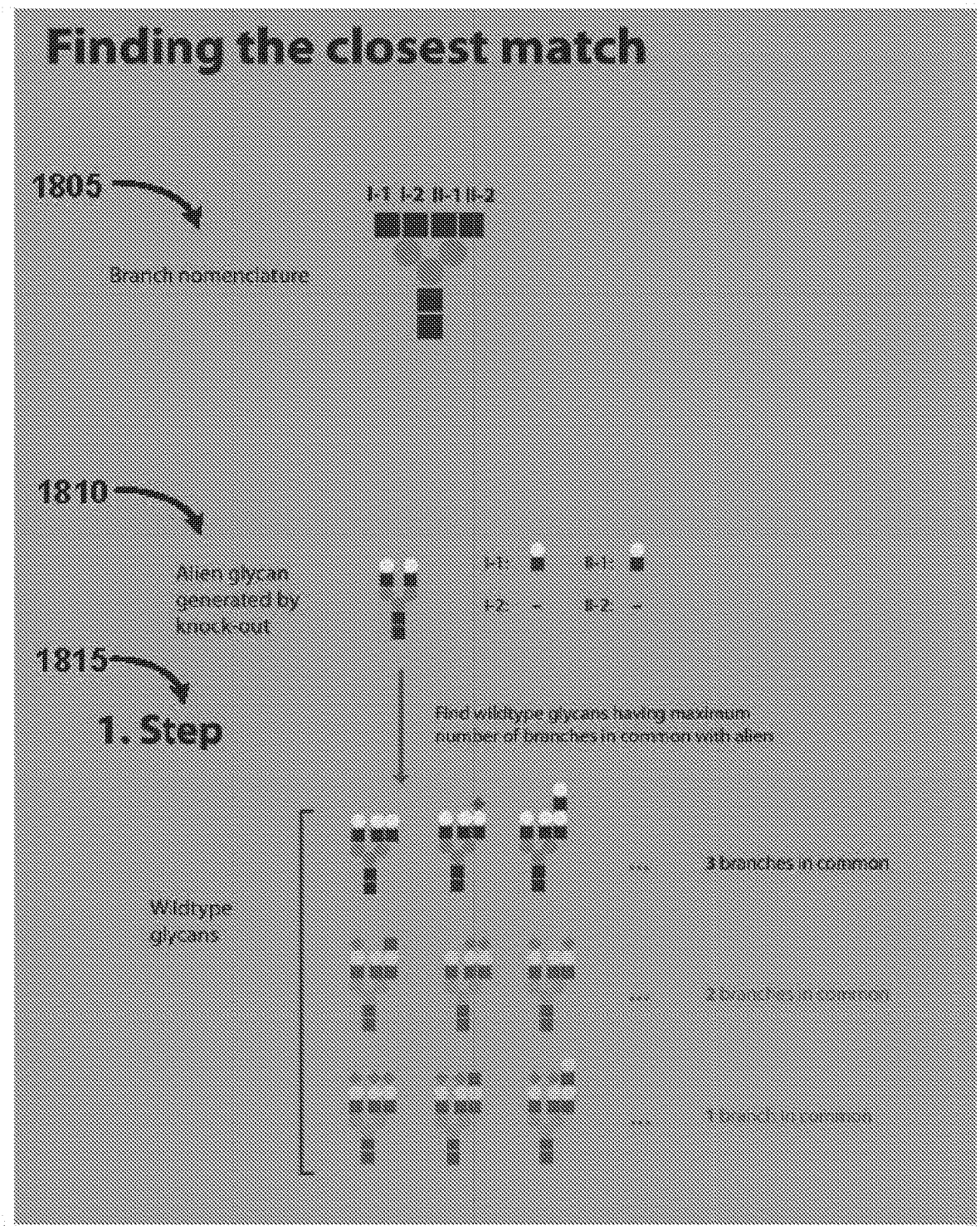
FIGS. 18A-18B. Find a closest match for an alien glycan. N-glycans can have a maximum of four branches at the tip which are named I-1/I-2/II-1/II-2 for this purpose. The branch configuration of the alien glycan is compared to the branch configurations of each glycan present in the Golgi compartment. Those glycans having the highest number of branches in common with the alien are retained as candidates. Missing branches are processed. It is assumed that alien glycans with missing branches will behave most similarly to glycans that have a copy of the neighboring branch where the alien branch is missing.
Figure 18B:
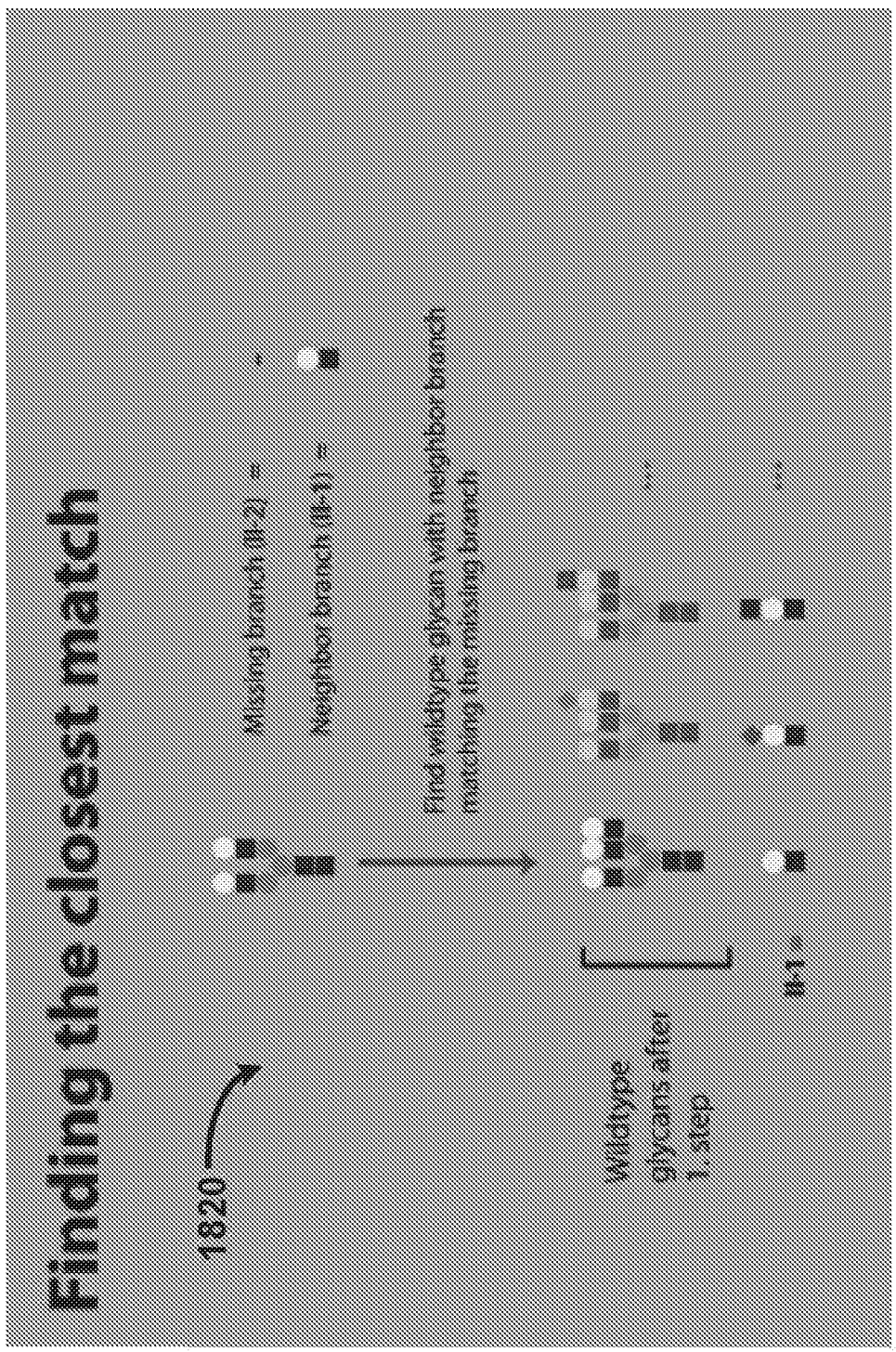

For each alien glycan found in the previous step, the script identifies its "closest match" among the wildtype glycans in that compartment (FIGS. 18A-18B). Based on the assumption that similar glycans are likely subject to similar reactions, the script tries to reconstruct reactions for the alien based on the reactions present for the wildtype glycan being closest to it in regard to morphology and chemical similarity. For this, first all wildtype glycans from the compartment are identified that have the maximum number of branches (encoded as substrings) in common with the alien. Among these, the program compares each branch separately for its congruence with the corresponding branch on the alien and calculates a measure representing the overall distance between the wildtype and the alien glycan based on the comparisons of all branches. Morphology is accounted for by comparing the branch lengths (=number of monosaccharide units) while chemical similarity is accounted for by comparing the monosaccharides at the branch tips since these represent the substrate for additional reactions. In total, the distance function is:

$$\sum_{branches} \alpha \cdot d_L + \beta \cdot d_C$$

with $d_L=|L_1-L_2|$ being the difference in branch length and:

$$d_C = \begin{cases} 0 & \text{if } G_1^* = G_2^* \\ 1 & \text{otherwise} \end{cases}$$

being the chemical discrepancy ($G_i^*$ is the terminating monosaccharide on glycan i). Both parts of the distance function can be weighted with parameters chosen by the user ($\alpha=1$, $\beta=3$ used for default).

If, as a consequence of a knock-down of a branching enzyme, the alien glycan misses a branch that is present on all wildtype glycans, the script gives the lowest distance to the wildtype glycan whose corresponding branch equals the branch neighboring the missing one on the alien. In the theoretical case that the closest match is ambiguous, the program proceeds with the first one, and a warning message is displayed.

Figure 19A:
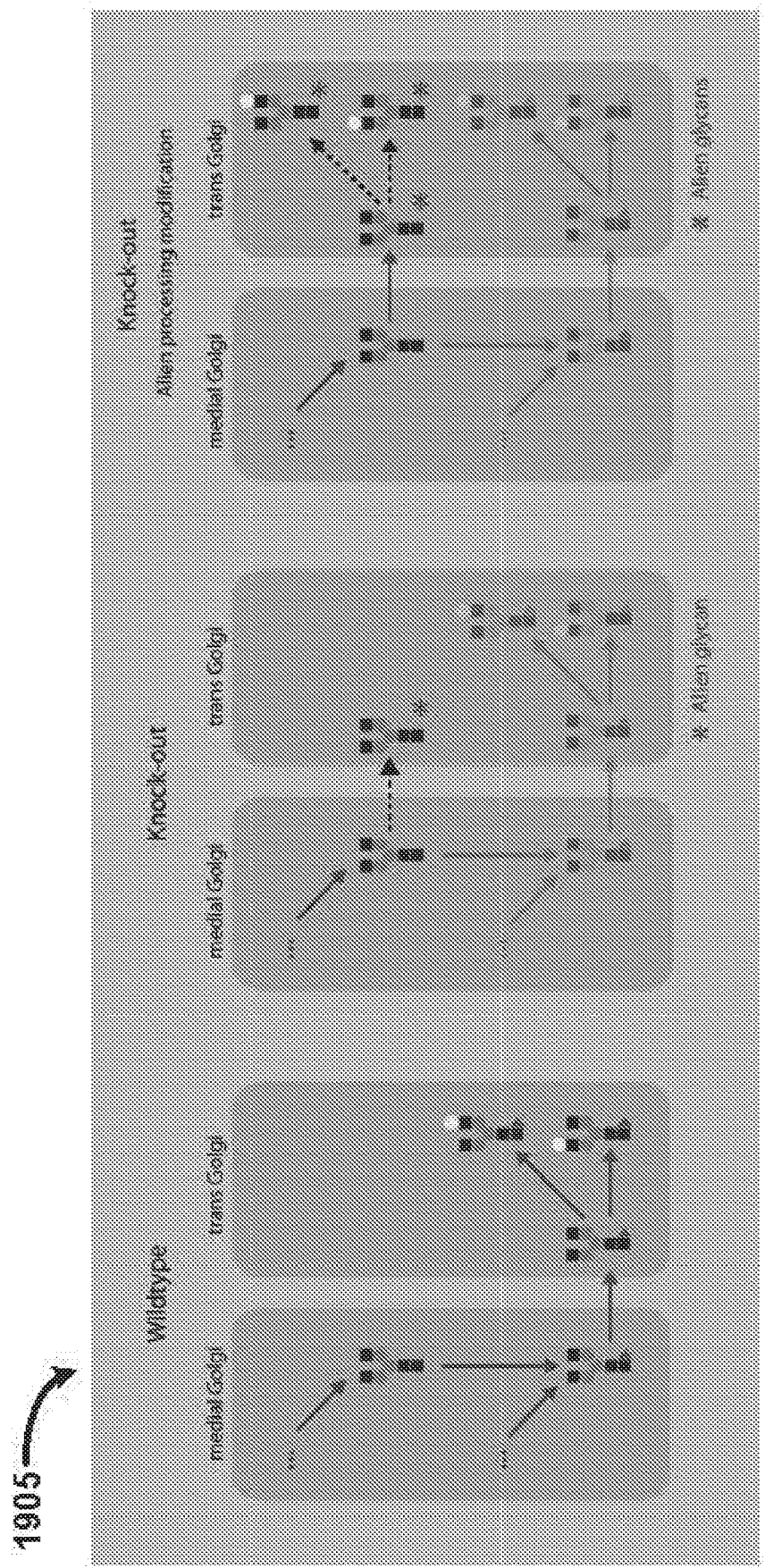
FIGS. 19A-19B. Processing of "alien" glycans after an enzyme knock-out (I). After FUT8 is knocked out, the non-fucosylated glycan is passed on into the trans Golgi where it lacks any further reactions since all trans-Golgi glycans in the wildtype network are fucosylated. As this non-fucosylated "alien" glycan closely resembles its fucosylated variant (the "closest match"), it will likely undergo analogous processing (galactosylation in this case), so the reactions on the closest match are assumed to occur likewise on the alien (dotted arrows). Step 1 To build the reactions for the alien glycans, the closest match to an alien glycan is chosen from the pool of wildtype glycans available in the same compartment on the basis of chemical and structural similarity (FIG. 18A). Step 2 The analogous reactions are linked to the alien glycan (in this case: galactosylation of both branches). Step 3: Corresponding transition probabilities are assumed to be identical to the analogs in the wildtype. Slight adjustments are required in more complicated cases where certain reactions on the closest match cannot be copied as they lack a reaction substrate on the alien. Since, typically, analogous reactions on the alien will themselves create new alien glycans, not present in the wildtype network (in this case galactosylated glycans lacking the core fucose), this procedure is repeated until all aliens have been processed. Glycan localization labels are omitted for clarity.
Figure 19B:
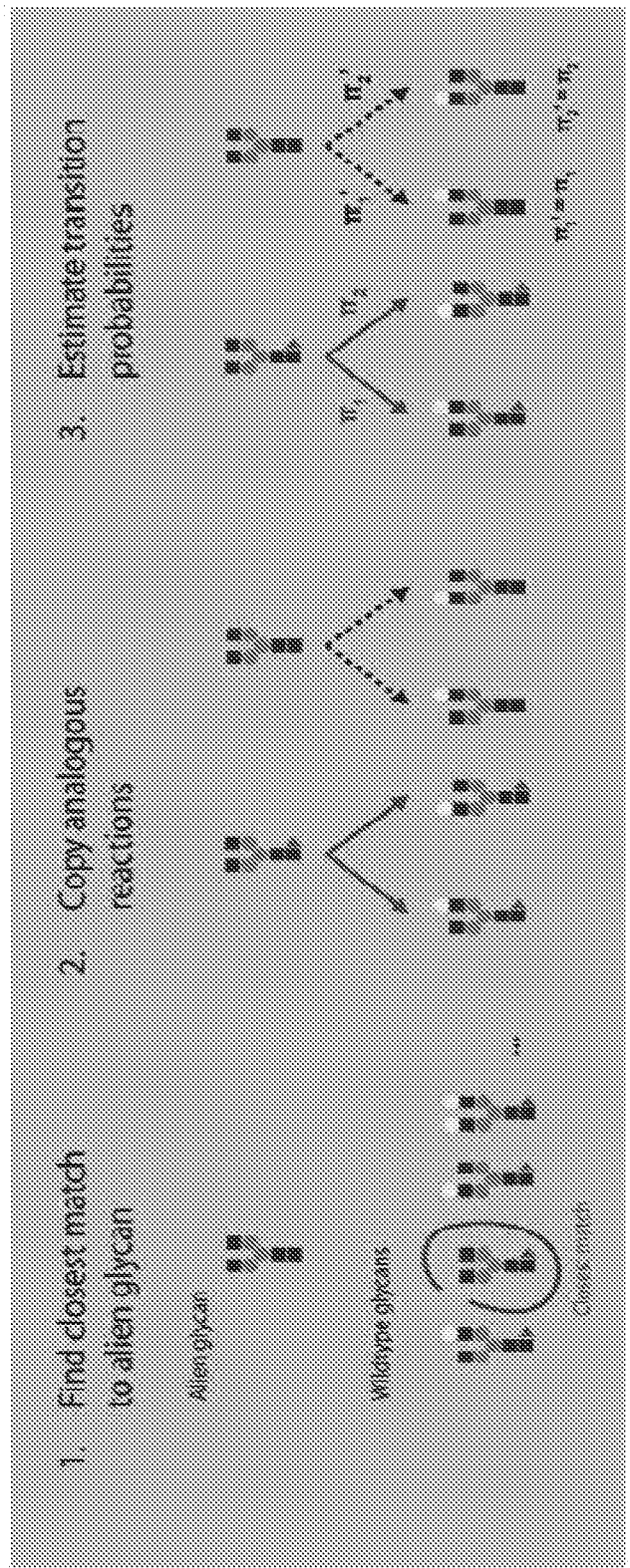
Figure 20A:
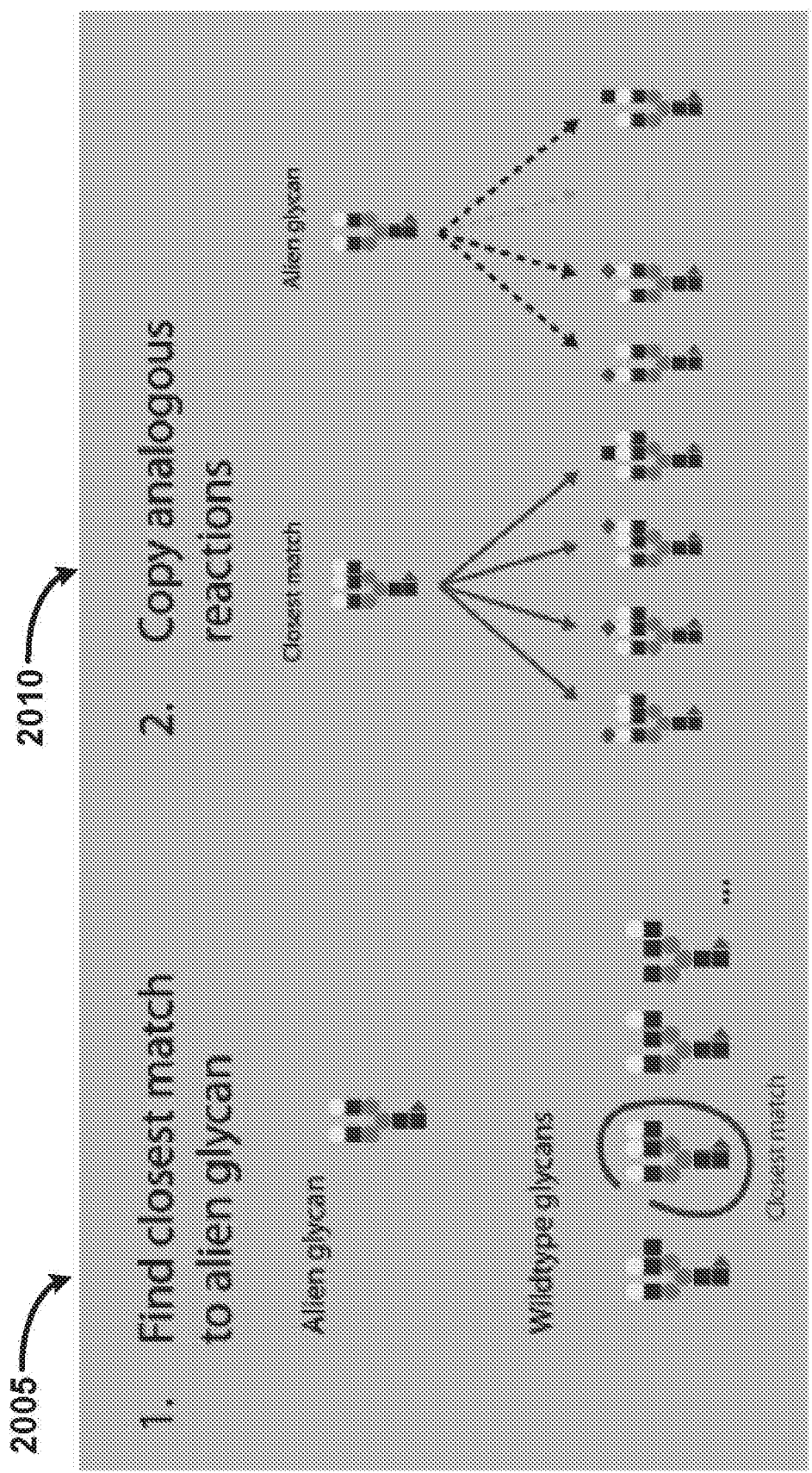
FIGS. 20A-20B. Processing of "alien" glycans after an enzyme knock-out (II). Step 1: In this example, a simulated GnTV knock-out leads to alien glycans in the trans-Golgi that, unlike their wildtype counterparts, lack the β1-6-GlcNAc bisection. Step 2: Consequently, subsequent modifications of this branch do not have analogs in the alien glycan since the required substrate is missing and a corresponding reaction cannot be copied over. Step 3: To estimate transition probabilities, these same adjustments are applied as for the knock-down, under the constraint that one transition is missing, i.e. it has a probability of 0.
Figure 20B:
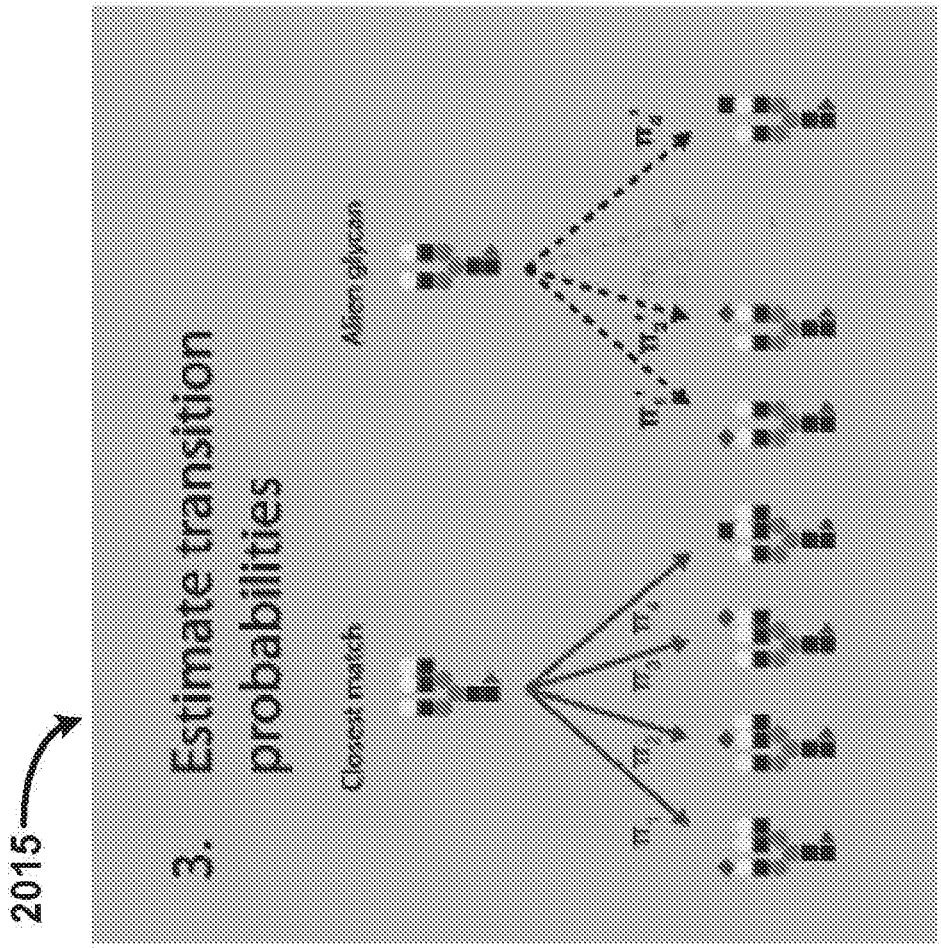

Next, the program considers all reactions taking place on the closest match and adds analogous reactions to the alien glycan if the proper reaction substrate is present and the alien meets the structural reaction constraints for the particular enzyme (Table 1). If no analogous reaction can be added, the alien is passed on to the next compartment or secreted, respectively. The probabilities for the reconstructed analogous reactions are calculated by the same rationale as in the knock-down, with the only difference that the probabilities π t now represent the probabilities for the reactions on the closest match (FIGS. 19A-19B; FIGS. 20A-20B).

Figure 21:
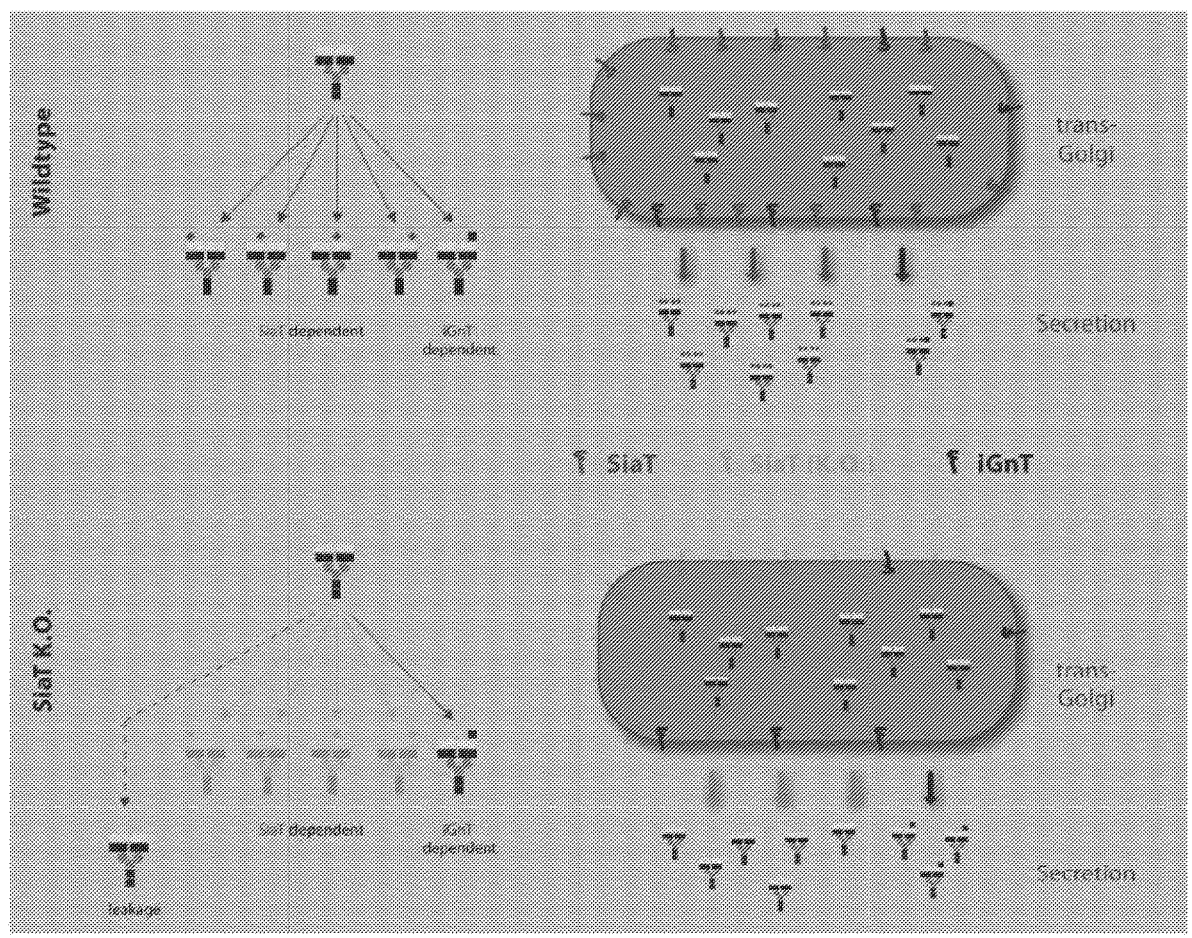
FIG. 21. Glycan leakage (I). After the knock-out of a dominating enzyme (SiaT) in a Golgi compartment, glycan leakage occurs when the co-localized enzyme (iGnT) is not capable of processing the entire bulk of glycan substrates. These will then pass the compartment unmodified, instead.
Figure 22A:
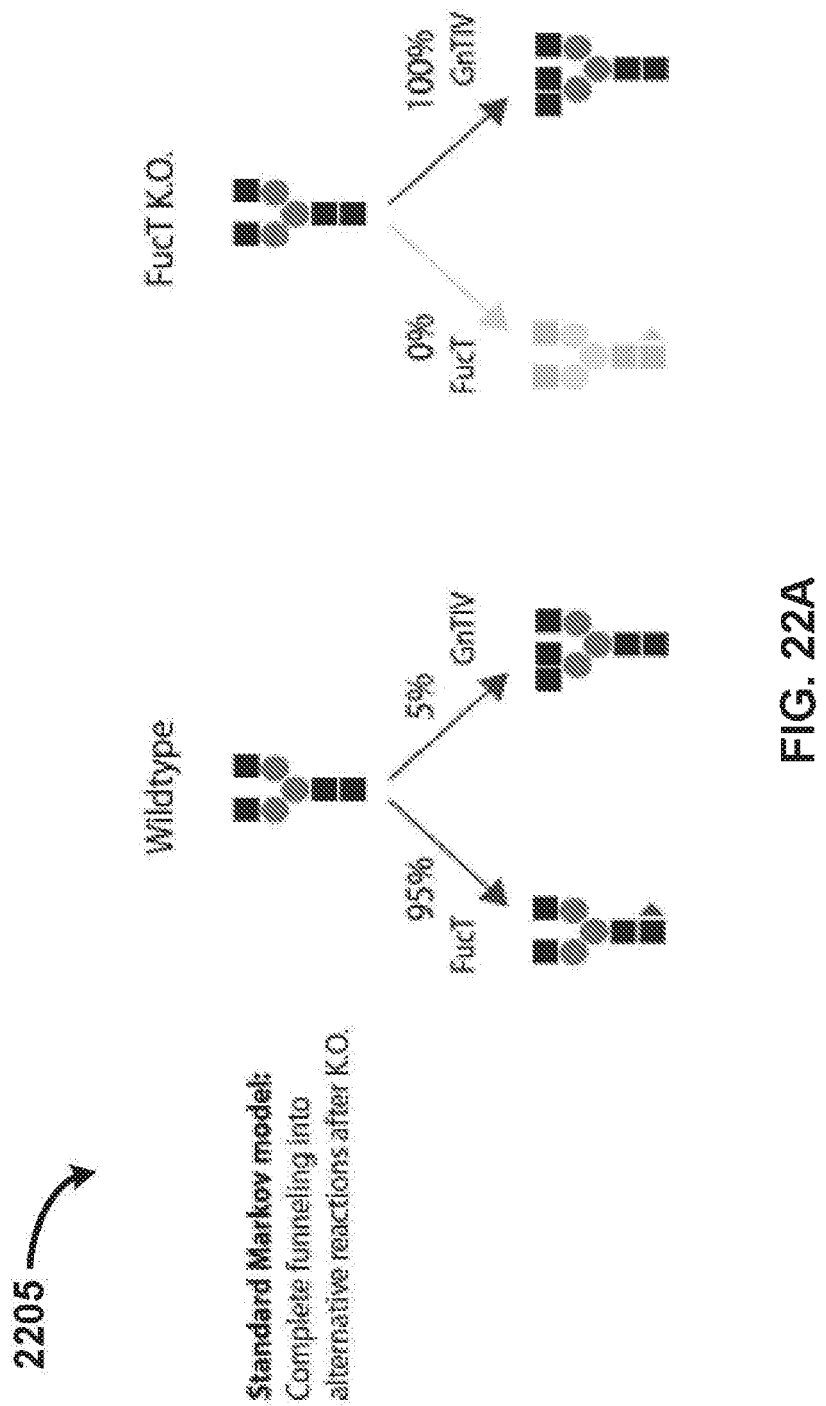
FIGS. 22A-22B. Glycan leakage (II). (2205). In this example, reconstruction of the glycosylation network yielded a dominating role of the fucoyltransferase (FucT) in processing of the particular glycan. The competing reaction (GnTIV-dependent) occurred only with 5% probability. Without the assumption of glycan leakage, the entire probability mass would shift to GnTIV in case of a FucT knock-out. (2010). Leakage only takes place if the probability mass lost to a knock-out exceeds a threshold T, based on the assumption that losses of small probability masses will likely be made up for by the co-localized enzymes. In case of leakage, its probability will increase the more probability mass is lost during the knock-out.
Figure 22B:
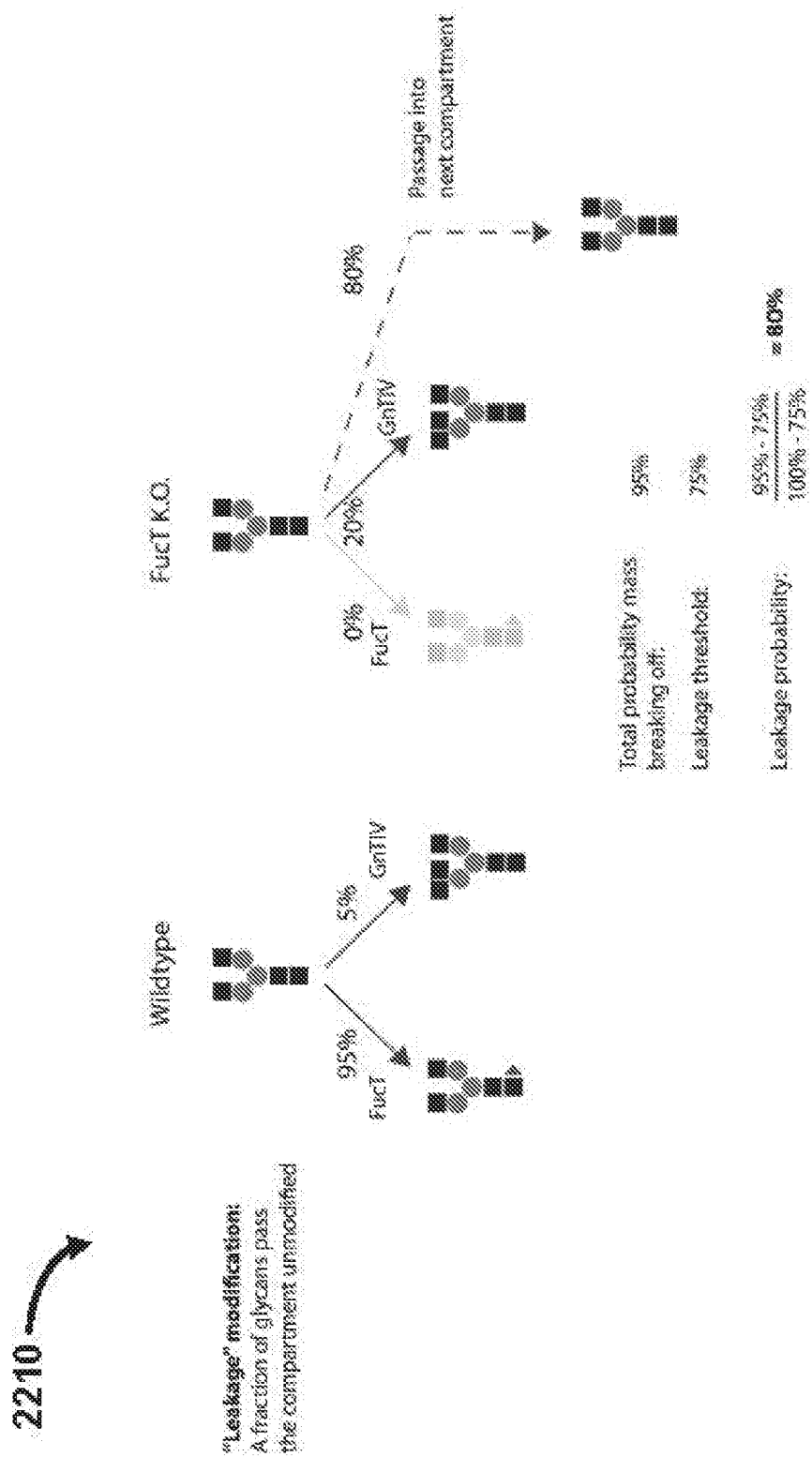

Finally, one optional parameter can be used to control the ability of the remaining enzymes to completely make up for the loss of a competing enzyme due to a knock-out. It is conceivable (and backed up through experiments, see below) that after a dominating enzyme has been knocked out in a Golgi compartment, the remaining enzymes are unable to process the bulk of glycan substrates present in the compartment. In this case, a fraction of glycans will pass the compartment without undergoing further modification—a concept we call "glycan leakage" (FIG. 21; FIGS. 22A-22B). The user can control this leakage by specifying a leakage threshold (one for each compartment). If, after a knock-down, the total probability mass lost through that knock-down exceeds this threshold, glycan leakage will occur. The more probability mass was lost during the knock-down, the higher the probability for leakage (FIGS. 22A-22B).

After this processing has been carried out for all knock-down pre-models, an array of transition matrices is obtained representing a Markov model for the knock-down situation. Running these Markov models, i.e. calculating their absorption probability, yields the predicted mutant glycan profile.

(b) Simulation of Perturbation in the Reaction Network: Enzyme Overexpression

Figure 10:
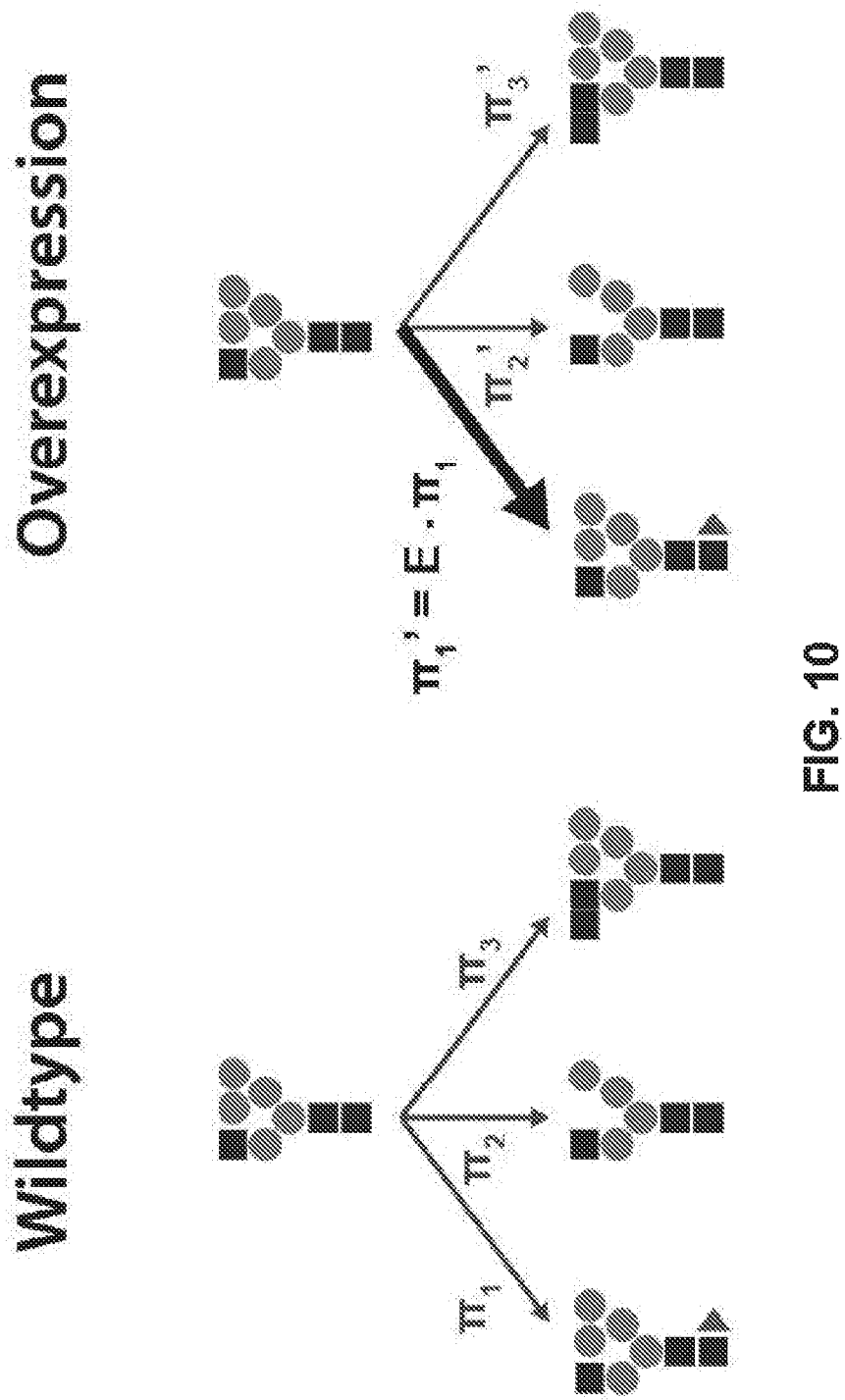
FIG. 10. Modeling enzyme overexpression. In analogy to the knock-out approach, overexpression is modeled by scaling up a certain transition probability by a factor E (>1), specified by the user. Remaining probabilities have to be adjusted by maintaining their ratios as in case of the knockdown.
Figure 11:
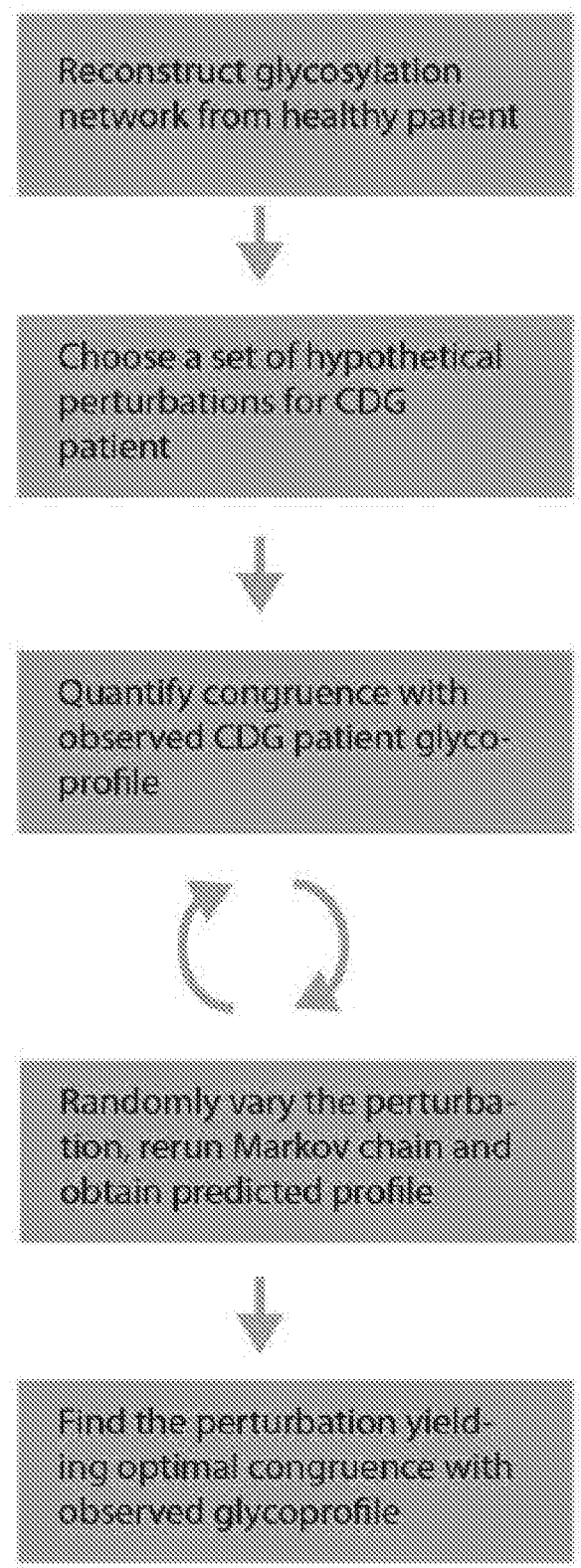
FIG. 11. Model-aided analysis of glycosylation deficiencies. Flowchart showing the workflow for the genetic algorithm using the Markov model to find the perturbance in the glycosylation reaction network that best explains the pathological glycoprofile of a patient.

Enzyme overexpression is simulated analogously to an enzyme knock-down. The user submits a wildtype Markov model together with an enzyme to be overexpressed as well as an overexpression parameters $E>1$. The program first identifies all glycans in the network having reactions that depend on the enzyme to be overexpressed, and, subsequently, cycles through this glycan list to adjust transition probabilities. For this, the probability of the affected reaction is scaled up to:

$$\pi'=\min(E \cdot \pi, 1)$$

and the probabilities for alternative reactions (if present) are calculated as laid out before (FIG. 10). Since transitions into new compartments are not created in this way, alien processing is not necessary, and the Markov chain can be readily re-run to yield the predicted glycoprofile gained through the overexpression.

Each network perturbation is assumed to take place independently. Thus, an arbitrary number of perturbations can be simulated by running the perturbation protocol for either a knock-down or an overexpression one at a time as described above.

(c) Simulation of Perturbation in the Reaction Network: Combined Enzyme Knock-Down and Overexpression Each network perturbation is assumed to take place independently. Thus, an arbitrary number of perturbations can be simulated by running the perturbation protocol for either a knock-down or an overexpression one at a time as described above.

(d) Simulation of Alternative Localization Hypotheses

Knowledge on enzyme localization is of relevance since co-localized enzymes compete for the same substrates. Thus, different assumptions on enzyme localization considerably impact reaction network topology. In order to test two competing localization hypotheses, the network tailoring is carried out separately for each of the two hypotheses. Subsequently, perturbations of the network for which the user has experimental data at hand, are simulated separately yielding predicted glycoprofiles which will likely be different from each other. Visual comparison with the experimental profile by the user now allows to judge which localization hypothesis is more consistent with actual data and thus more likely to be true.

Knowledge of localization can also be used for glycoengineering using this framework. Localization of enzymes can be changed in model to identify enzyme localization that would result in the desired glyan profile or a profile that is near to a desired profile. Since most enzymes have domains that determine localization in the cell, enzyme editing strategies can use this information to change the localization of the enzyme based on the model results. For example, using site-directed mutagenesis or gene synthesis, one can alter or exchange protein domains on glycosyltransferases that specify intra-Golgi localization of the enzyme (for example, to localize the protein to the trans—rather than the medial Golgi). Such a localization change would change the topology of the entire generic reaction network since it would allow reactions to take place that were not possible before while at the same time eliminating reactions. In the generation of the generic glycosylation network, the localization of each glycosyltransferase is a parameter chosen by the user. Thus, experimental changes in glycosyltransferase localization can be readily modeled. After the generation of such an alternative reaction network, the network be tailored by fitting to a glycoprofile (obtained from the cell line with the alternatively localized glycosyltransferase) in order to reconstruct reaction probabilities in this alternative network.

(e) Simulation of Congenital Diseases of Glycosylation (CDG)

The generic glycosylation network is tailored to the observed glycoprofile from a healthy patient. The space of possible perturbations (knock-downs/overexpressions) that lead to the observed glycoprofile from the CDG patient is then explored using a genetic algorithm as implemented in MATLAB. However, any other optimization algorithm can be employed to identify the best combination of perturbations that match the patient glycoprofile. For this, the program minimizes an objective function measuring the Euclidian distance between the predicted and the observed profile. Other distance metrics can also be employed. If using a genetic algorithm, the user specifies an initial hypothesis of perturbations perturbations (such as, but not limited to increases or decreases in enzyme level, changes in enzyme activity through regulation or substrate concentrations, etc.), as well a stopping condition, such as a maximum number of iterations of the genetic algorithm, a critical threshold for the objective function or a run-time limit. The obtained end-point of the optimization process is a set of perturbations that best explains the data retrieved from the patient and can serve as a guide to assess the severity with which individual enzyme-dependent reactions are affected, thus which genetic defects are a likely cause of the disease.

(f) Simulation of Growth Media Adjustments

Figure 12:
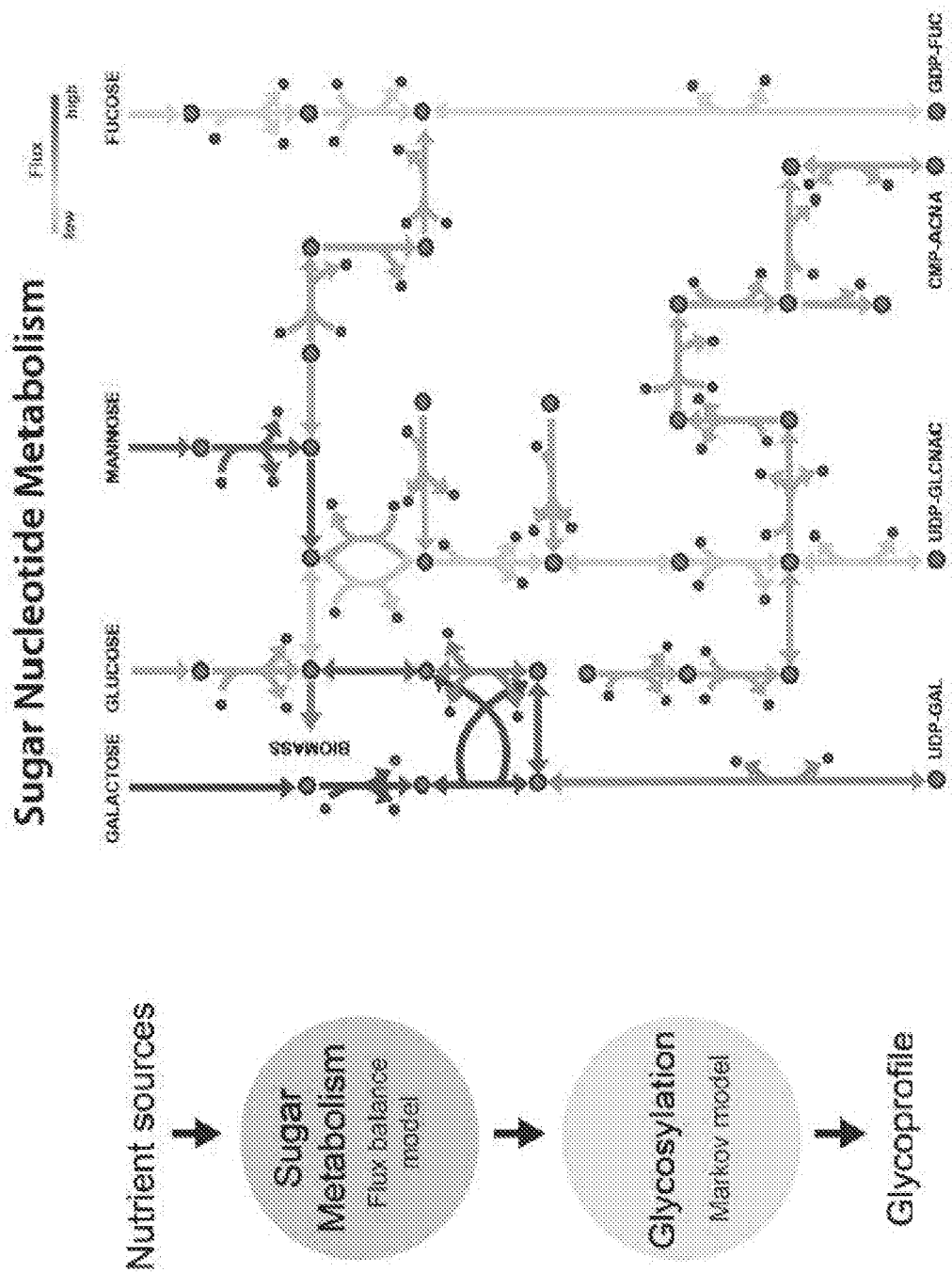
FIG. 12. Coupling the Markov model to sugar nucleotide metabolism. By coupling the Markov model of glycosylation to a COBRA model of sugar nucleotide metabolism, the effects of manipulations in growth conditions, such as alternative feeding strategies, can be linked to simulations of glycosylation under these perturbed conditions.
Figure 13:
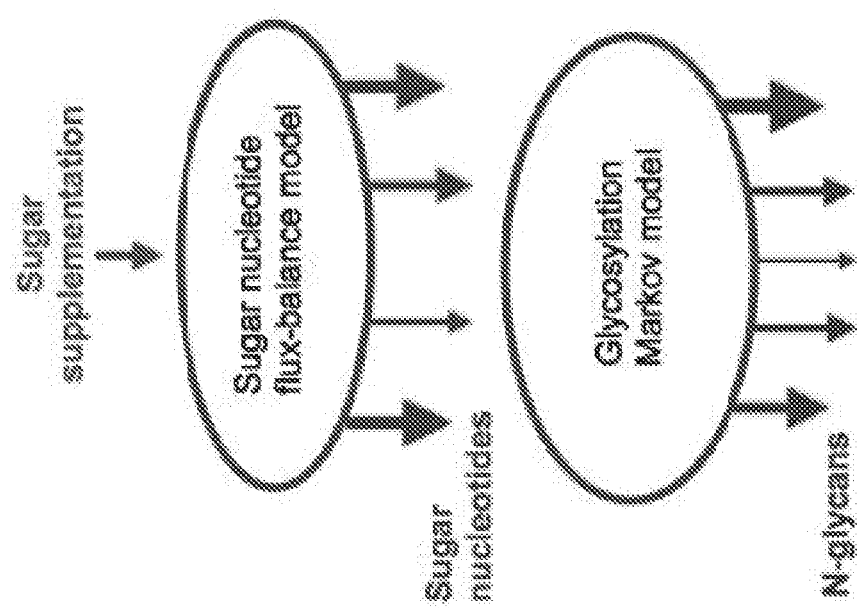
FIG. 13. Changes in feeding leads to changes in sugar nucleotide fluxes which will lead to changes in N-glycans. In the most simple model, a linear relationship between the flux ratio of sugar nucleotides (before and after the perturbation) and the reaction probabilities of glycosylation reactions requiring the particular sugar nucleotide is assumed ($\pi_{alt}$ and $\pi_{wt}$ refer to the reaction probabilities before and after the perturbation, respectively).

A COBRA model is manually or algorithmically created and comprises the biochemical reaction network (as described in the literature) linking various nutrients (glucose, galactose, mannose, fructose, glutamine and others) to the production of sugar nucleotides that serve as the precursors for the glycosylation reactions in the Golgi. Tailoring the generic glycosylation network to a glycoprofile obtained from a cell line under standard conditions reconstructs the fluxes at which sugar nucleotides are taken up into the glycosylation network. These fluxes are fixed (i.e. they do not vary among different flux samples taken) since it is only the internal fluxes within the reaction network that can show variation. Thus, these fluxes can be imposed on the sugar nucleotide reaction network in order to reconstruct the flux through the sugar nucleotide network producing the observed glycoprofile (FIG. 12). By constraining the uptake fluxes of all compounds not included in the growth media of the culture, sampling the fluxes through the sugar nucleotide network reconstructs the space of possible metabolic paths through which the external nutrients (e.g. glucose and glutamine) are linked to the generation of sugar nucleotides feeding into glycosylation. In order to simulate the effect of supplementation with additional nutrients (e.g. galactose), a method from the COBRA toolbox (Minimization Of Metabolic Adjustment, or MOMA) is used to calculate how a reconstructed flux will change once an additional nutrient is fed into the network. However, other algorithms that predict the adjusted fluxes after a perturbation can be used, including, but not limited to those described in Lewis, Nagarajan and Palsson, Nature Reviews Microbiology, 2012. The resulting changes in the export fluxes of the sugar nucleotides are saved and set in relation to the fluxes in the standard condition. These ratios now represent the x-fold increase or decrease of sugar nucleotidesynthesis and thus the x-fold higher/lower availability of that compound for subsequent glycosylation reactions. These ratios (q) now affect the probability by which glycosylation reactions that are dependent on these compounds will take place. In a simple linear model, probabilities can be rescaled according to $\pi'=q\cdot\pi$. Although alternative models, including non-linear models, can be used. Thus reactions take place with an x-fold higher/lower probability if the availability of the required sugar nucleotides is x-fold increased/decreased. After running the probability adjustment protocol as described, the Markov chain is re-run yielding the predicted glycoprofile, as a response to the changed nutrient supplementation (FIG. 14).

(g) Identification of Glycoengineering Steps for Biosimilar Production

Aspects of the present disclosure are applicable to the manufacturing of biosimilars. Biosimilars have to closely resemble the glycoprofile of the original product which, typically, exhibited a mixture of glycans. In other words, instead of starting with perturbing the reaction probabilities (e.g. through a knock-out) and then calculating the glycoprofile, biosimilar manufacturing requires reversing the workflow as to start with a glycoprofile and inferring the perturbations in reaction probability that will lead to the glycoprofile.

Thus, in some embodiments, one would start with a wildtype cell line under standard conditions whose glycoprofile can be measured (the initial glycoprofile). In addition, the desired glycoprofile is known (the target glycoprofile). As before, one would first fit the Markov model to the initial glycoprofile in order to estimate reaction probabilities. Next, an initial guess has to be made which perturbations (i.e. glycosyltransferase(s) to be knocked down) would turn the initial glycoprofile into the target glycoprofile. A genetic algorithm (as e.g. implemented in MATLAB) can then take this initial guess as a starting point and iteratively run simulations of the Markov chain that would eventually converge and identify which glycosyltransferases have to be knocked down (or overexpressed) and by how much in order to get from the initial glycoprofile to the target glycoprofile. Genetic algorithms are not the only approach, so other optimization algorithms known by those skilled in the art are applicable to this application.

Importantly, an embodiment of the model only identifies the required changes in the glycosylation reaction network, but it would be left at the user's discretion to make a choice regarding the experimental means of how to achieve these required changes. For example, the simulation run could finish by stating that a 67.2% reduction in fucosyltransferase-dependent reactions is required to obtain the target glycoprofile. The user could now choose an experimental technique to implement this requirement, e.g. through an shRNA targeting the fucosyltransferase transcript, a chemical inhibitor (whose dose would have to be adjusted to obtain the required reduction in activity) or changes in the growth media that would lead to a reduction of GDP-fucose which is the substrate of fucosyltransferase-dependent reactions. Regardless of the experimental method, aspects of the disclosed technology can provide clear guidelines of how to modify process conditions in biosimilar manufacturing in order to match the glycoprofile of the original product. This approach is applicable, as described above, to biosimilar development, but can also be applied to any other efforts to obtain a specific glycoprofile for biopharmaceutical or biobetter design.

This workflow of reverse-engineering the glycoprofile is analog to the identification of glycosylation gene malfunctions in the context of congenital disorders of glycosylation described herein.

(h) Extension to Alternative Glycosylation Reaction Networks

As will be appreciated by one of skill in the art, the present disclosure is not limited to N-linked glycosylation. Given a table of glycosyltransferase rule sets in analogy to Table 1, a generic reaction network can be constructed for, e.g., O-linked glycosylation or human milk oligosaccharides using the methods laid out previously. Given a glycoprofile, reaction probabilities can be inferred in these networks as laid out above.

(i) Identification of Glycosyltranferase Genes

Several types of glycans are less well studied, such as milk oligosaccharides, plant glycans, and microbial glycans. The disclosed system and method can be applied to discover and use glycosyltransferases. We now describe an example with human milk oligosaccharides. While the necessity of certain enzymatic reactions in the human milk oligosaccharide reaction network is clearly apparent based on the resulting oligosaccharide structures observed in glycoprofiles, the corresponding genes coding for the required glycosyltransferases are in many cases unknown, i.e. a set of putative candidates may be known based on sequence analysis, but it is unknown which of them actually shows expression and activity on milk oligosaccharides. Through combination with deep transcriptional profiling (such as RNA-seq), proteomics, or other assays that quantify the expression or activity of genes or proteins, the disclosed system and method can aid in the identification of these genes. For this, one would generate a generic network of all possible reaction that could contribute to the synthesis of all milk oligosaccharides based on the glycan structures. Then an oligosaccharide profile would be used to tailor the generic network to the specific measured glycans. Quantities of the oligosaccharides are then used to infer reaction probabilities for a oligosaccharide profile from a subject. This would be done for multiple subjects. Then the changes in Markov probabilities between subjects will be compared to differential gene expression or protein measurements to identify candidate genes that co-vary with the probabilities. Comparison of the inferred reaction probability with the expression strength of the putative gene candidates gives hints as to which of the genes is the most likely candidate. By collecting these data from not one but a cohort of patients, these inferences can be corroborated through correlation analysis. Throughout the specification various citations are referenced, and the entire content of each is hereby incorporated by reference. The following example is provided to describe the invention in more detail. It is intended to illustrate, not to limit the invention.

EXAMPLES

Example 1

Prediction of Glycoprofiles after Enzyme Knock-Down

Figure 23:
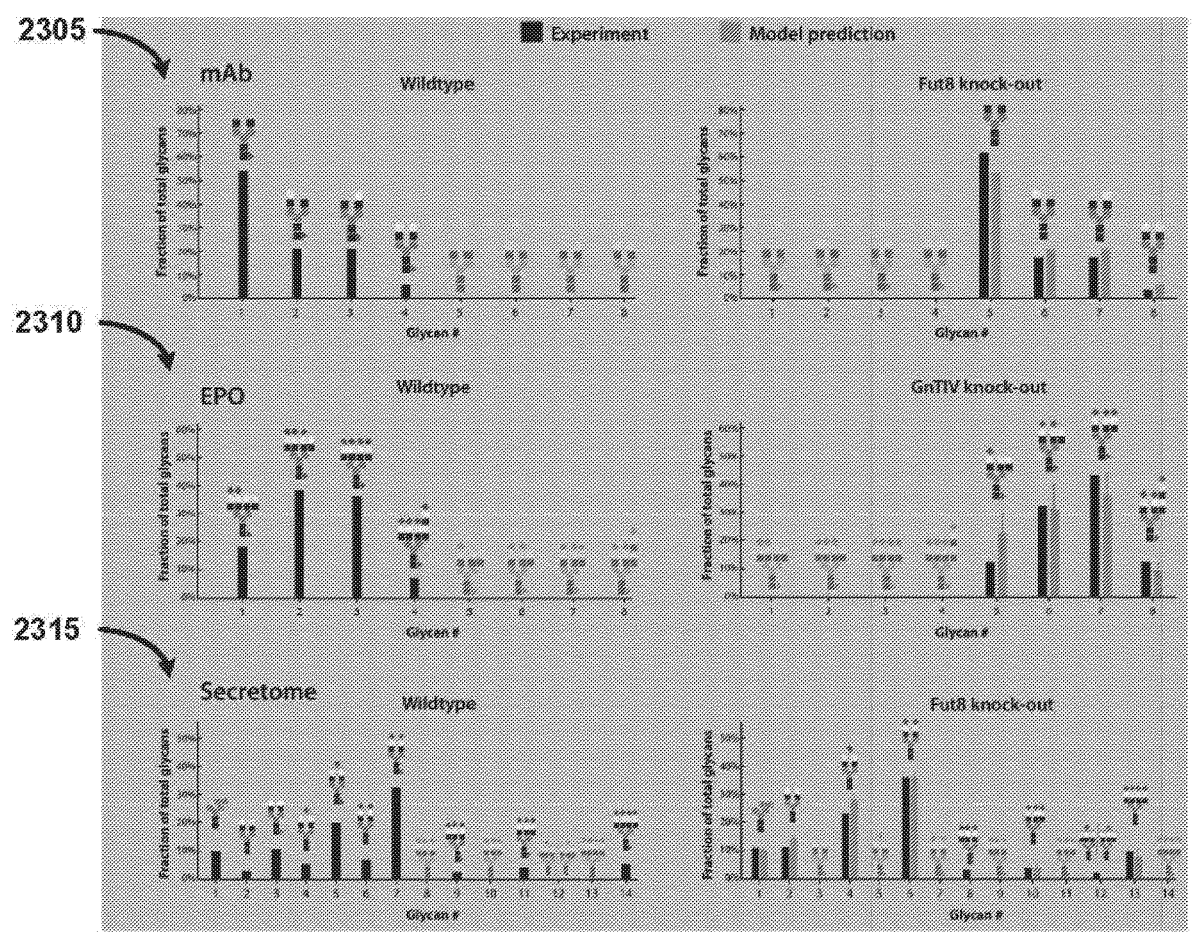
FIG. 23. Prediction of mutant glycoprofiles. Knock-out simulations ($\epsilon=0$) using the Markov model (grey bars). As shown in 2305 bars represent mean+/−s.d. Glycans with 0% frequency are shown transparent. Experimental data is shown in black bars. IgG1 glycoprofile from a wildtype and a FUT8 knock-out CHO/DG44 cell line with corresponding model predictions (Experimental data from (Imai-Nishiya et al., 2007)). As shown in 2310, EPO glycoprofile from a wildtype and GnTIV knock-out CHO-GS line with corresponding predictions (Experimental data from (Yang et al., 2015)). As shown in 2315, whole secretome glycoprofiles from a wildtype and FUT8 knock-out CHO-S suspension culture with corresponding predictions.

Examples of simulation of perturbation in the reaction network: Enzyme know-know, are shown in four cases. The first glycoprofile analyzed, as reported in (Imai-Nishiya et al., 2007) for an antibody producing CHO cell line, consisted of fucosylated, bi-antennary glycans. Experimental knock-down of FUT8 using siRNA had led to successful omission of the core fucosylation and the substitution of the three glycans with their non-fucosylated versions (Imai-Nishiya et al., 2007), a result very well predicted by the Markov model in simulations (FIG. 23).

Aiming for validation on a more complex dataset, recently published glycoprofiles from a CHO-GS cell line expressing erythropoietin (EPO) (Yang et al., 2015) were analyzed. Simulation of a GnTIV knock-out yielded good quantitative agreement with the experimental knock-out profile (FIG. 23), demonstrating that the Markov model can serve as a helpful predictive tool even in high-dimensional networks where intuitive analysis of knock-outs is impossible due to the sheer number of possible pathways.

Third, it was demonstrated how model can predict knock-down glycoprofiles even when applied to a mixture of proteins rather than one isolated protein. Simulation of a FUT8 knock-out in a CHO-S cell line proved to closely resemble the measured knock-out profile taken from the entirety of secreted proteins rather than one purified protein (FIG. 23).

Figure 24:
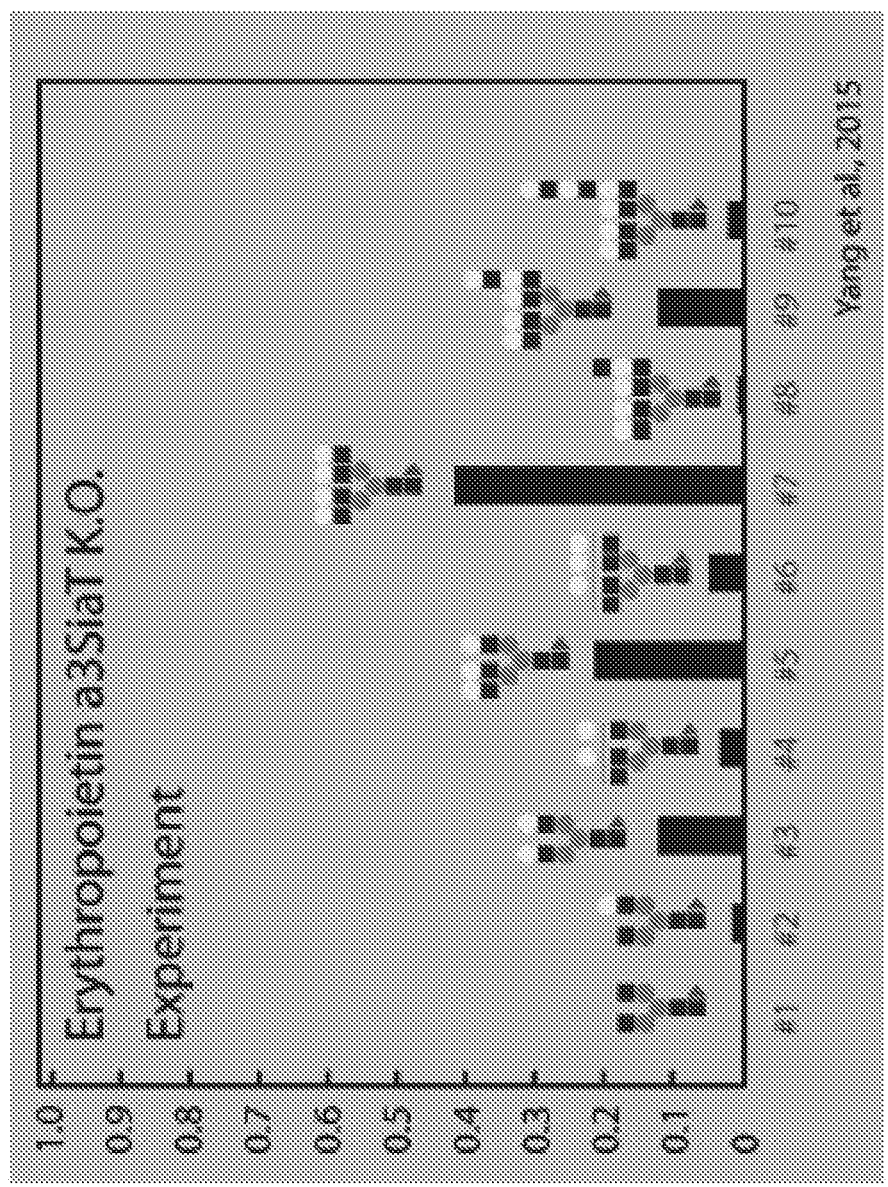
FIG. 24. Glycoprofile on EPO after an a3SiaT knock-out. The glycoprofile of the wildtype cell line is shown in FIG. 23. Data from (Yang et al., 2015).
Figure 25:
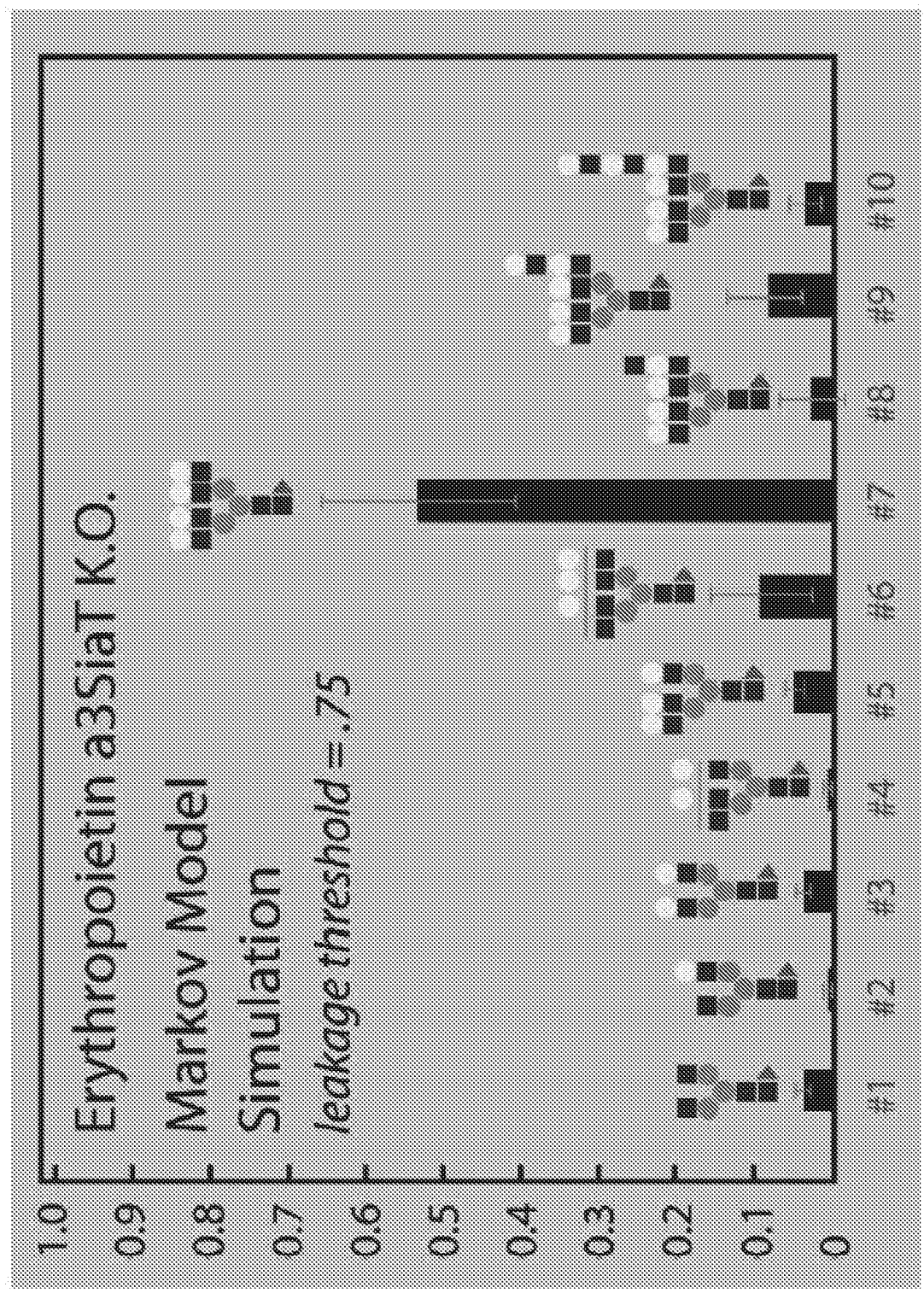
FIG. 25. Markov model simulation with an assumed leakage threshold of 0.75.
Figure 26:
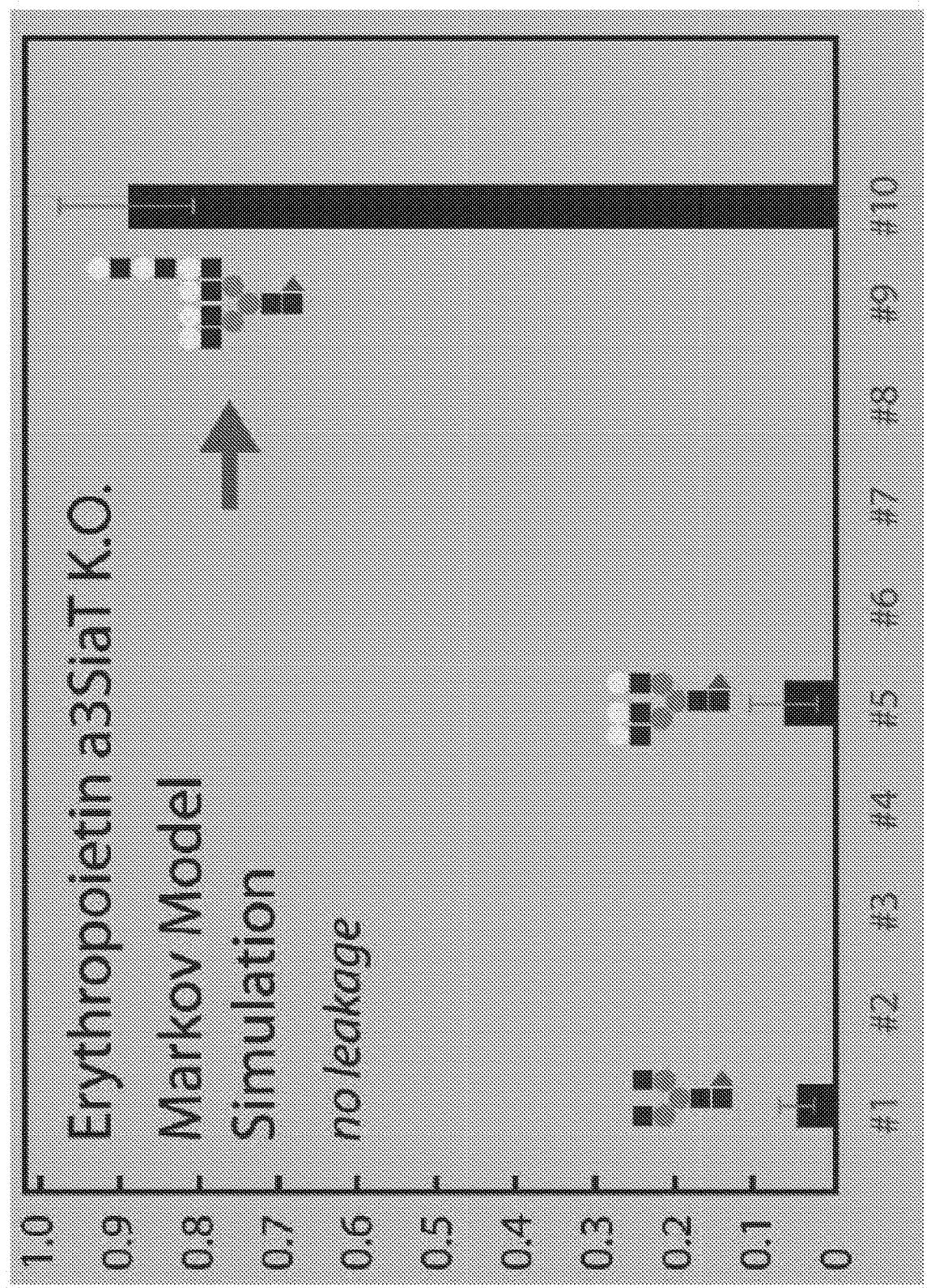
FIG. 26. Markov model simulation, run with leakage threshold set to 1.0 (no leakage in effect).

Finally, the phenomenon of glycan leakage was being made apparent when simulating a knock-out of a3SiaT, as documented experimentally in CHO-GS expressing EPO (Yang et al., 2015). Assuming glycan leakage, the model is able to predict the observed glycoprofile at a high precision (FIG. 24. FIG. 25). With no leakage assumed, the model predicts a dominating fraction of poly-LacNAc bearing glycans in the profile (FIG. 26, arrow) because it assumes that the co-localized enzyme (iGnT) is able to completely make up for the loss of a3SiaT and process the entirety of glycan substrates.

Example 2

Assessment of an Uncompartmentalized Golgi

Figure 27:
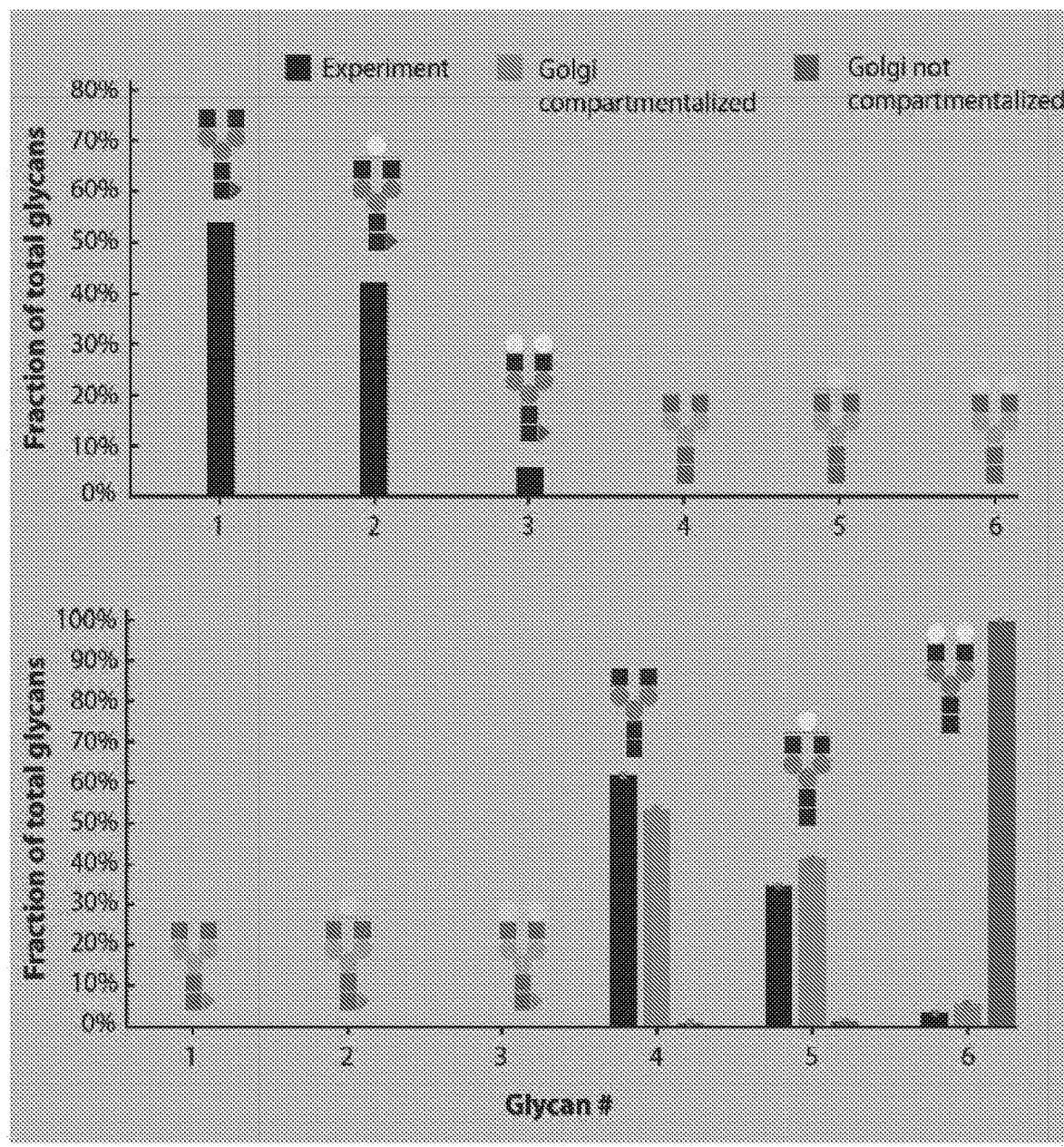
FIG. 27. Experimental FUT8 knock-out profile along with knock-out simulations, run either with the Golgi assumed to be compartmentalized (light grey bars) or not compartmentalized (dark grey bars).
Figure 28:
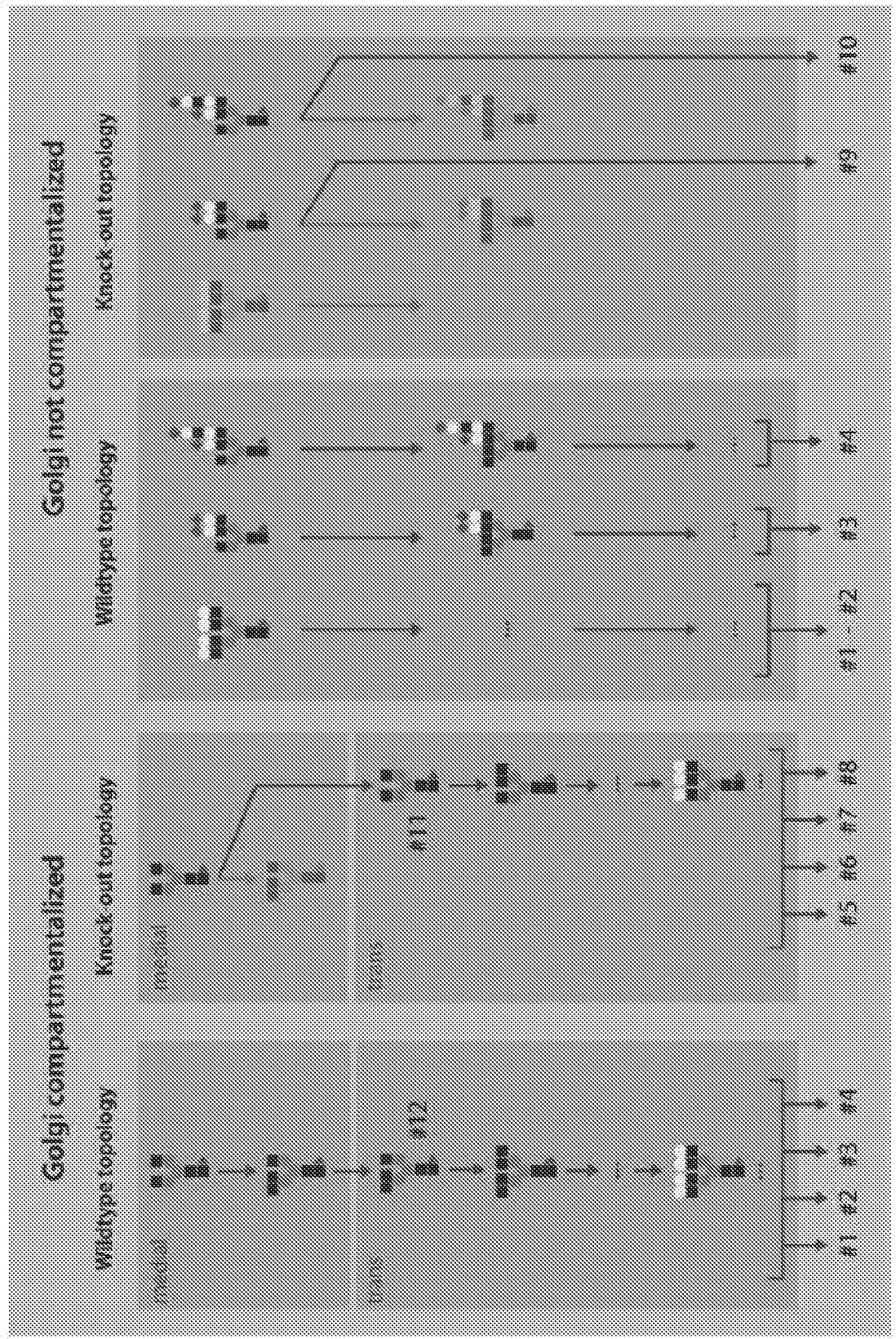
FIG. 28. A section of the network topologies implied by a compartmentalized and non-compartmentalized Golgi model, respectively. In case of compartmentalization, the knock-out of the fucosylation reaction leads to passage of the non-fucosylated glycan (#4) into the trans-Golgi where it is processed according to the reactions present on its closest match (#1). In case of no compartmentalization, the implied parallel action of FUT8 and GalT leads to a topology that would only secrete a single, fully galactosylated glycan (glycan #6) when fucosylation is knocked out.
Figure 29:
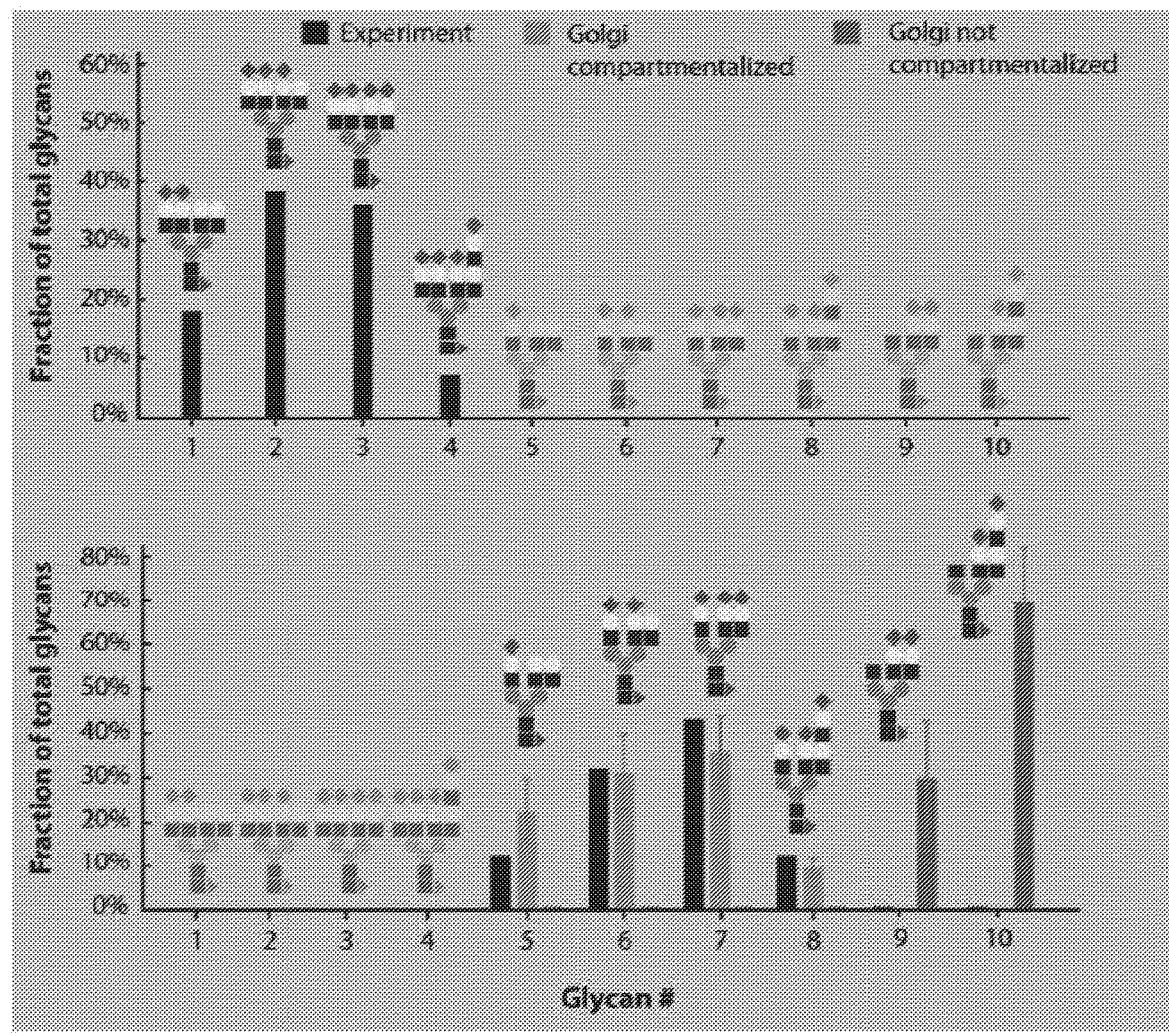
FIG. 29. Experimental GnTIV knock-out profile (black bars) along with knock-out simulations, run either with the Golgi assumed to be compartmentalized (light grey bars) or not compartmentalized (dark grey bars).
Figure 30:
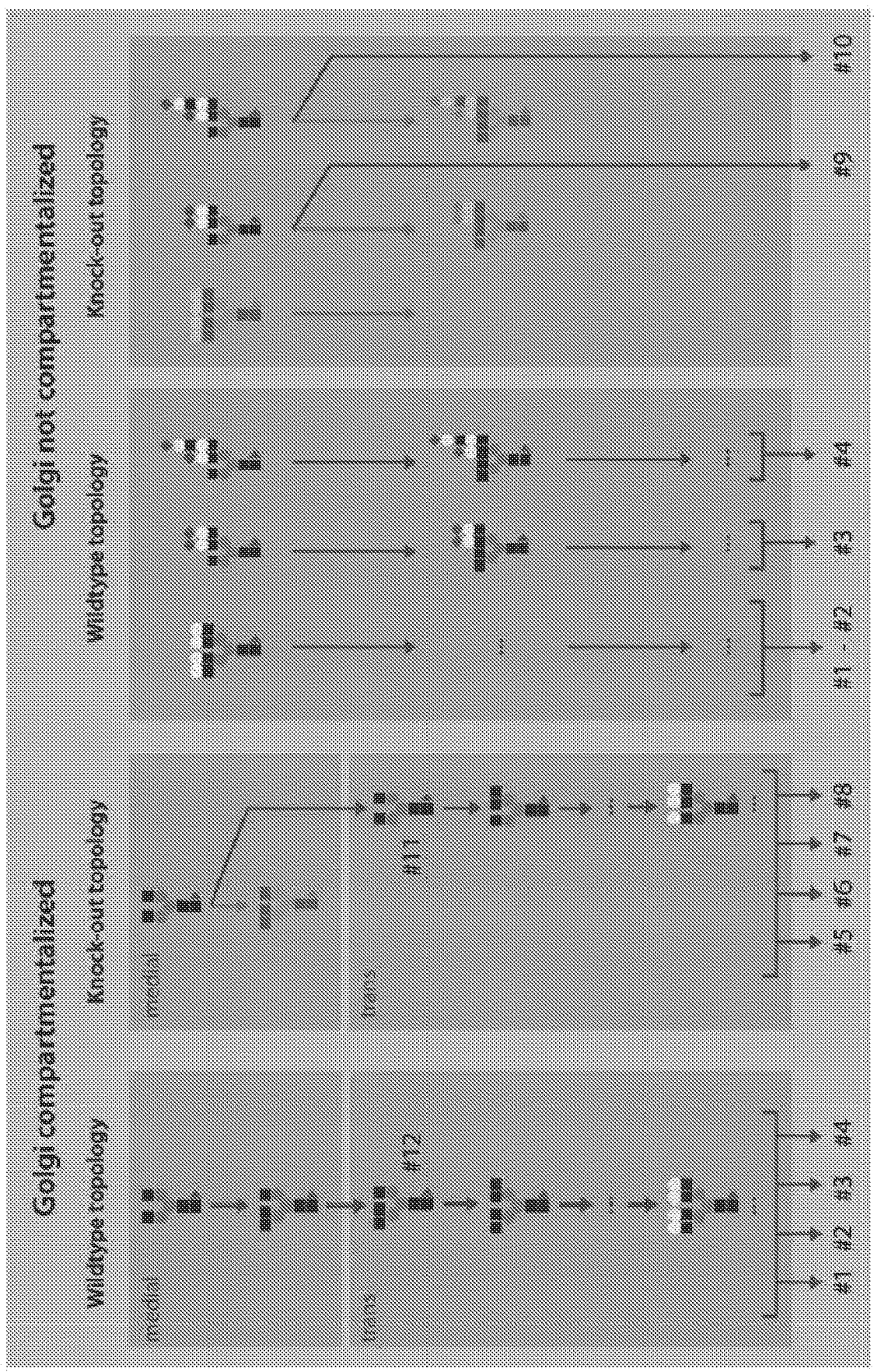
FIG. 30. In case of compartmentalization, the knock-out of the GnTIV-dependent branching in the medial Golgi leads to passage of the non-bifurcated glycan (#11) into the trans-Golgi where it is processed according to the reactions present on its closest match (#12), eventually leading to four tri-antennary structures (#5-#8). In case of no compartmentalization, the enzymes GalT and GnTIV act in parallel. As a consequence of the implied network topology, only two rather than four glycans (#9, #10) would be secreted once GnTIV is knocked out.

While the localizations assumed for this model rely on a widely accepted consensus (Table 1) (Moremen et al., 2012), there remain disagreements with how and to what extent Golgi compartmentalization is implemented in glycosylation models. Given the availability of mutant glycoprofiles, the invention model can test the impact of Golgi compartmentalization by running simulations with different localization scenarios and comparing them to the experimental results. To demonstrate this, knock-out simulations were run with all enzymes localized to the same compartment, thus effectively turning the Golgi into a non-compartmentalized organelle. As seen from the validation datasets, this leads to knock-out predictions not in congruence with the experimental glycoprofiles (FIG. 27). The discrepancies seen in this case stem from changes in network topology caused by the emergence of reactions that were absent in the compartmentalized case due to the confinement of enzymes to different compartments. For instance, in the case of the antibody glycosylation network (FIG. 28), absence of compartmentalization implies competition between GalT and Fut8 which was not present with both enzymes being localized to different compartments. As a consequence, simulation of a Fut8 knockout in this scenario significantly changes the predicted glycoprofile which would now only contain a single fully galactosylated glycan (glycan #6, FIG. 28). Similar changes in network topology lead to the falsely predicted glycans in a GnTIV knock-out if GalT is assumed to directly compete with GnTIV in a non-compartmentalized Golgi (FIG. 29, FIG. 30). Therefore, it is concluded that Golgi compartmentalization is a property being vital for computational glycosylation modeling efforts. Thus, by testing different localization scenarios, the invention model serves as a tool to assess the likelihood of localization hypotheses based on the congruence between predicted and observed knock-out glycoprofiles, and for predictions of how glycosyltransferase localization can be modified to obtain a desired glycoprofile.

Example 3

Analysis of a Congenital Disorder of Glycosylation

Figure 31:
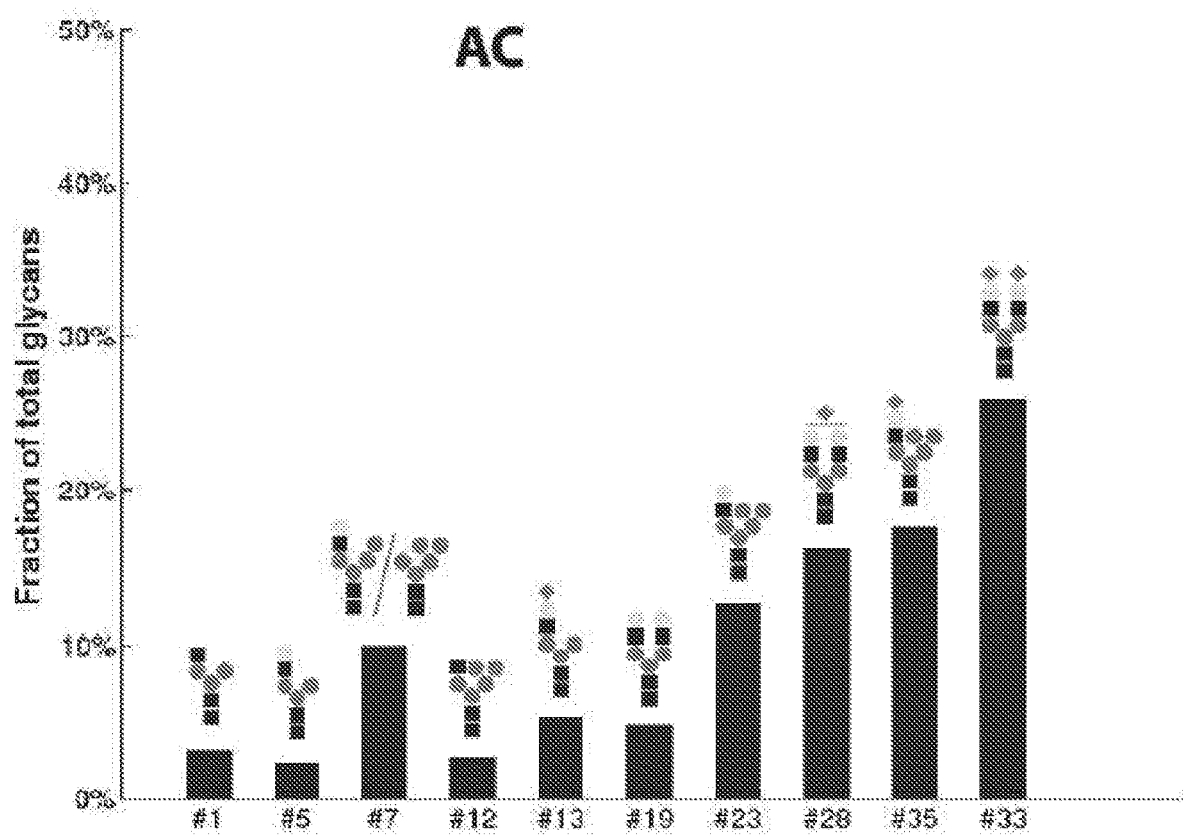
FIG. 31. Aberrant glycoprofile from a CDG patient. The patient ("AC") shows altered N-glycan composition of the transferrin glycoproteins in the blood.
Figure 32:
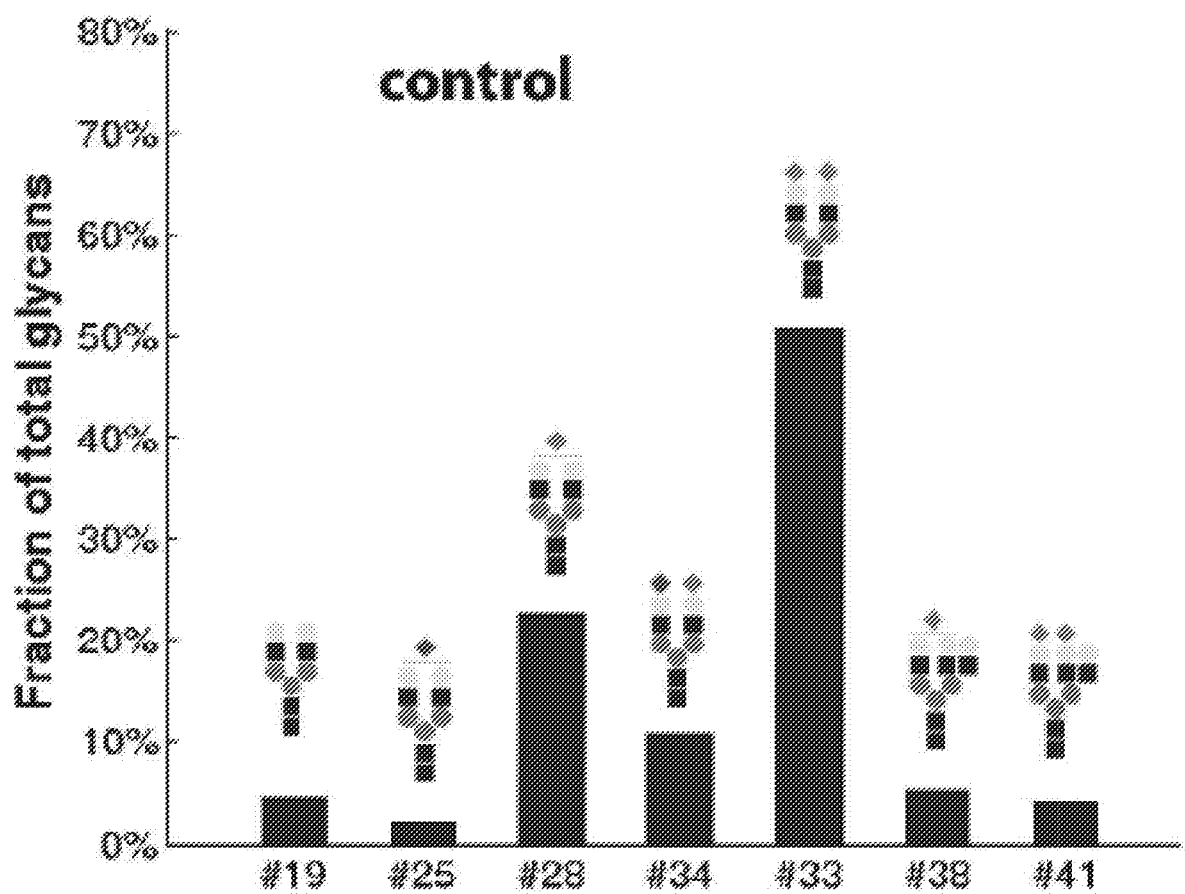
FIG. 32. A glycosylation profile of transferring from a healthy patient. Data from (Butler, 2003).
Figure 33:
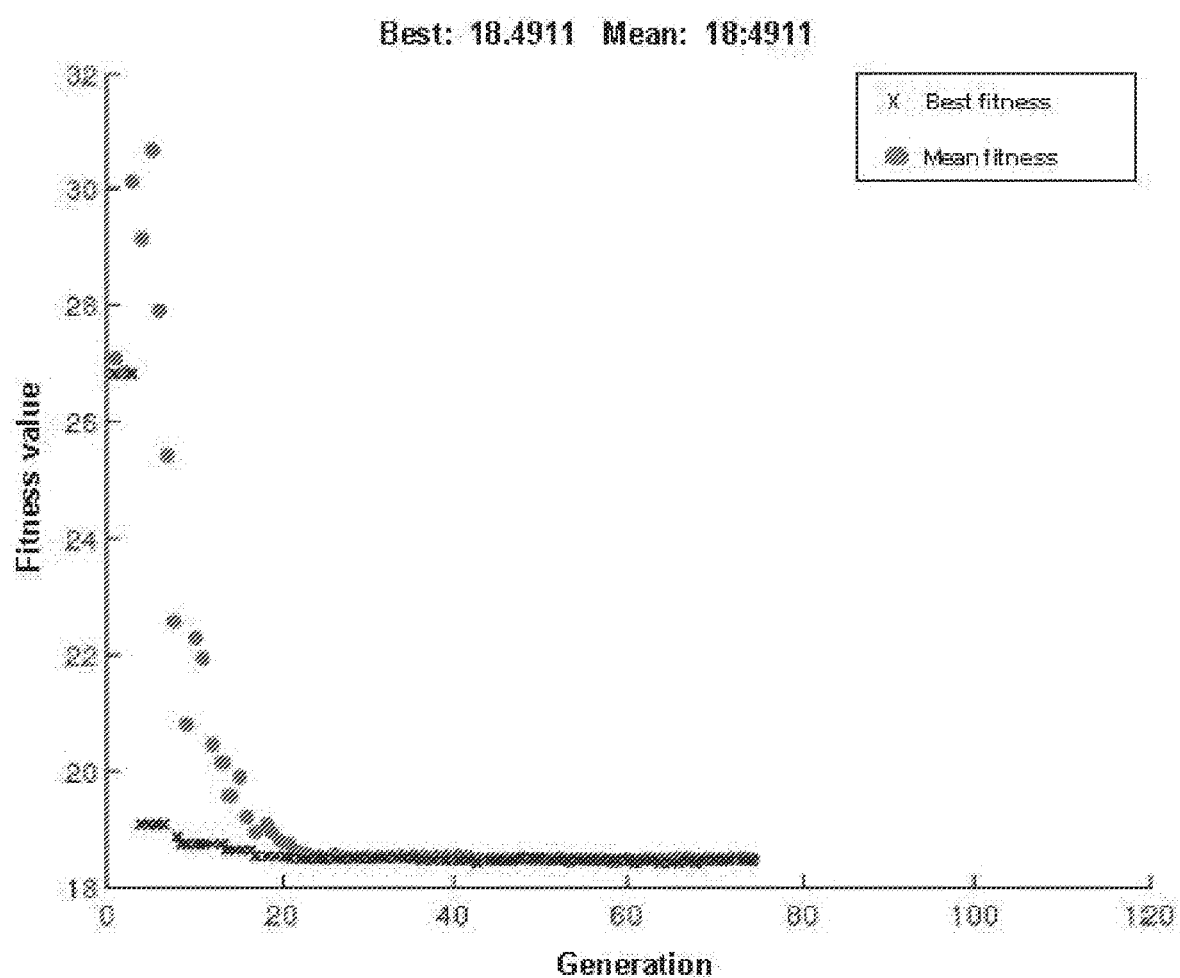
FIG. 33. Application of the Markov model to analyze a glycosylation disorder. Best fit (black) and mean fit (blue) of the predicted patient profile to the observed profile, plotted for 75 generations until convergence.
Figure 34:
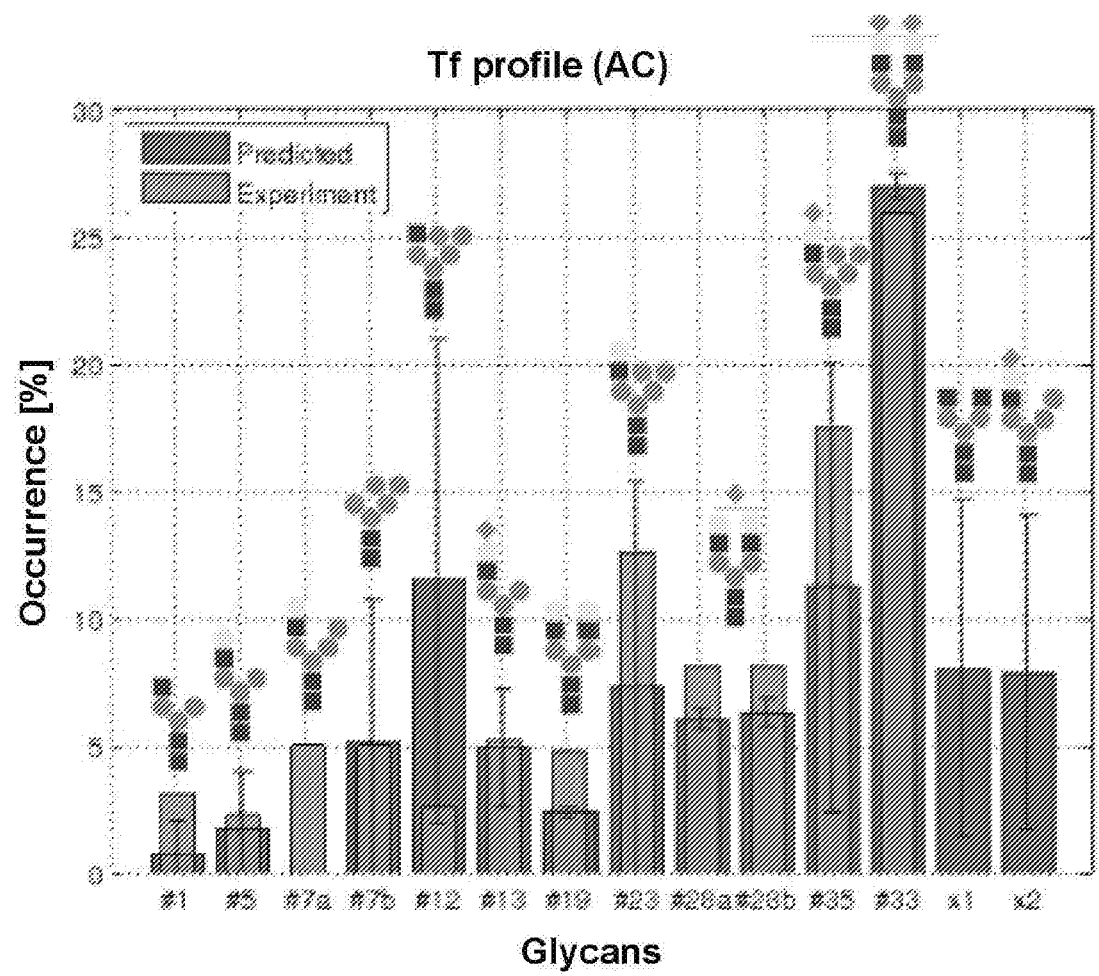
FIG. 34. Predicted (dark) and observed (light) glycan frequencies after completion of the genetic algorithm.

An aberrant glycoprofile from a patient was obtained who suffered from a glycosylation disorder with unclear genetic origin (Butler, 2003) (FIG. 31). After tailoring the generic glycosylation network to the glycoprofile from a healthy patient (FIG. 32), a genetic algorithm (as implemented in MATLAB) was used to find the perturbation in the reaction network that would come closest to the profile seen in the patient. After running the algorithm for 75 generations, the Euclidian distance between the predicted and the observed patient profile showed no further improvement indicating a local optimum (FIG. 33). At the optimum, ManII-dependent reactions were predicted to be knocked down to 71%, GnTI-dependent reactions to 85% and GnTII-dependent reactions to 87% while a3SiaT- and GnTV-dependent reactions were predicted to be at 0% (FIG. 34). These results indicate that the glycosylation network of the patient is more heavily affected than hypothesized in the description of the original data where only the GnTII-dependent pathways were considered to be downregulated (Butler, 2003).

Example 4

Shifting the Glycoprofile Through Media Supplementation

Figure 35:
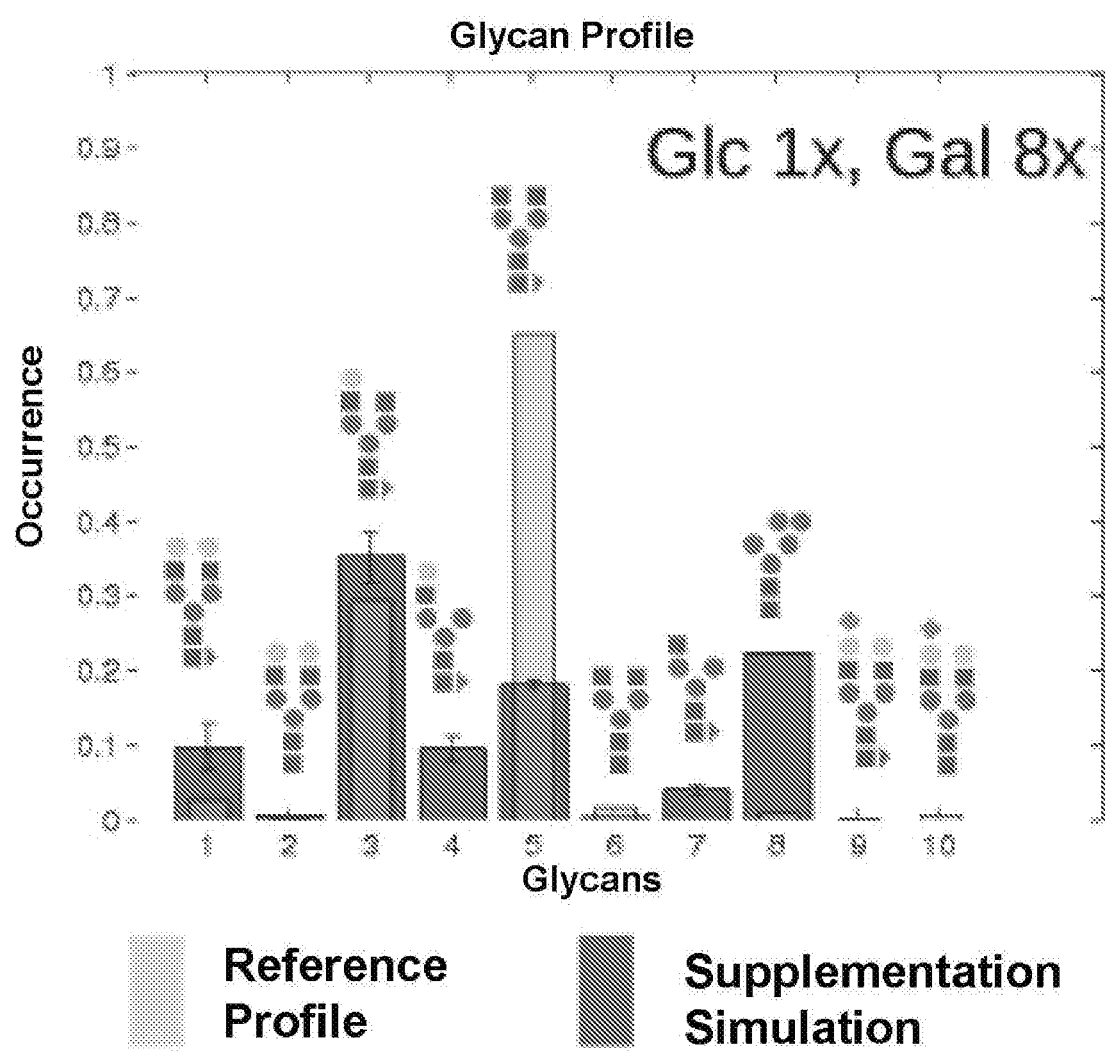
FIG. 35. Simulation of galactose supplementation. Galactose uptake is simulated relative to glucose uptake. Galactose supplementation leads to an increase in galactosylated glycans (#1-#4) with a concomitant decrease in non-galactosylated glycan #5.
Figure 36:
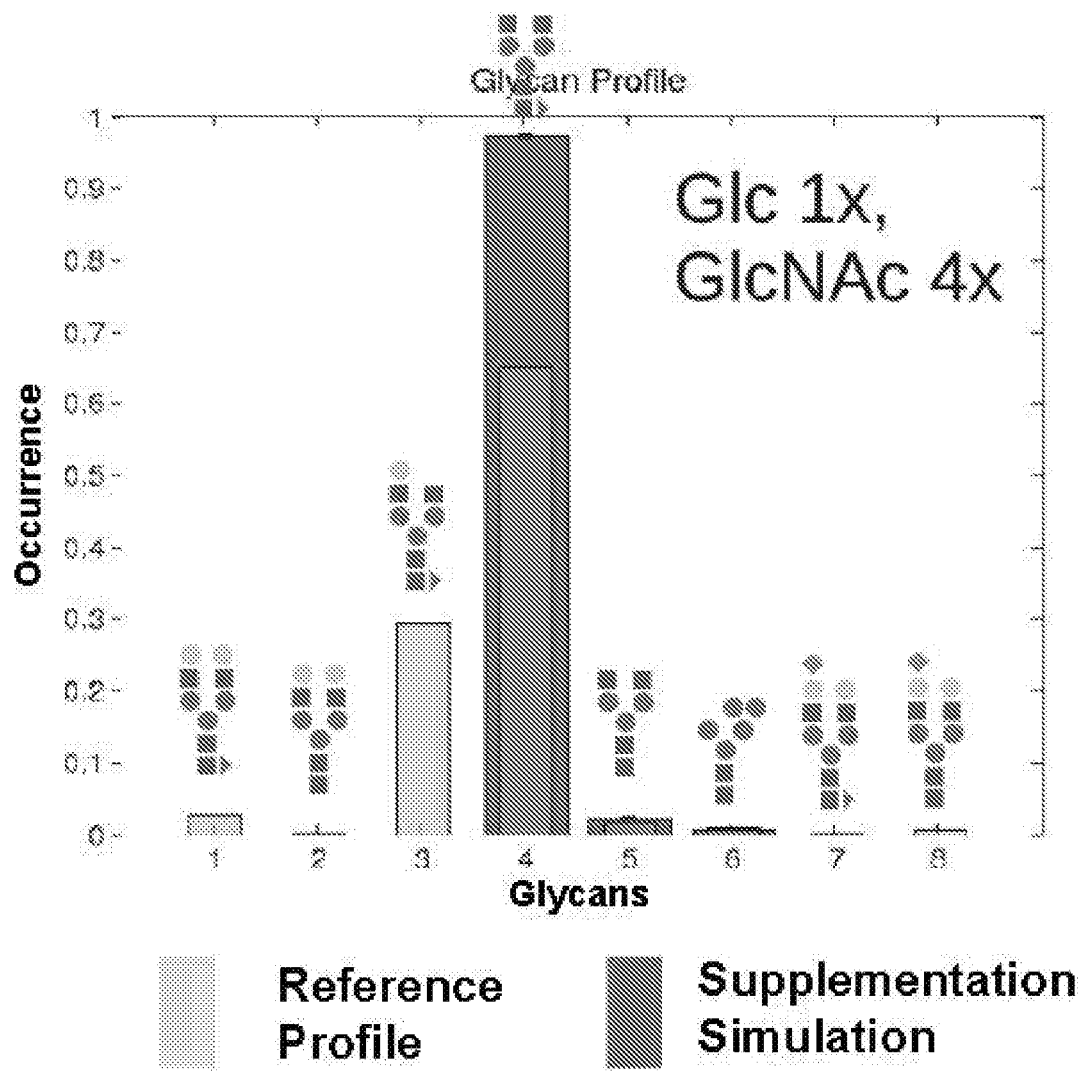
FIG. 36. Simulation of GlcNAc supplementation. GlcNAc supplementation leads to an increase of non-galactosylated glycan #4 and to a decrease in galactosylated glycans. Reference profile without galactose or GlcNAc supplementation (Gal0x, GlcNAc0x) is shown in light.
Figure 37:
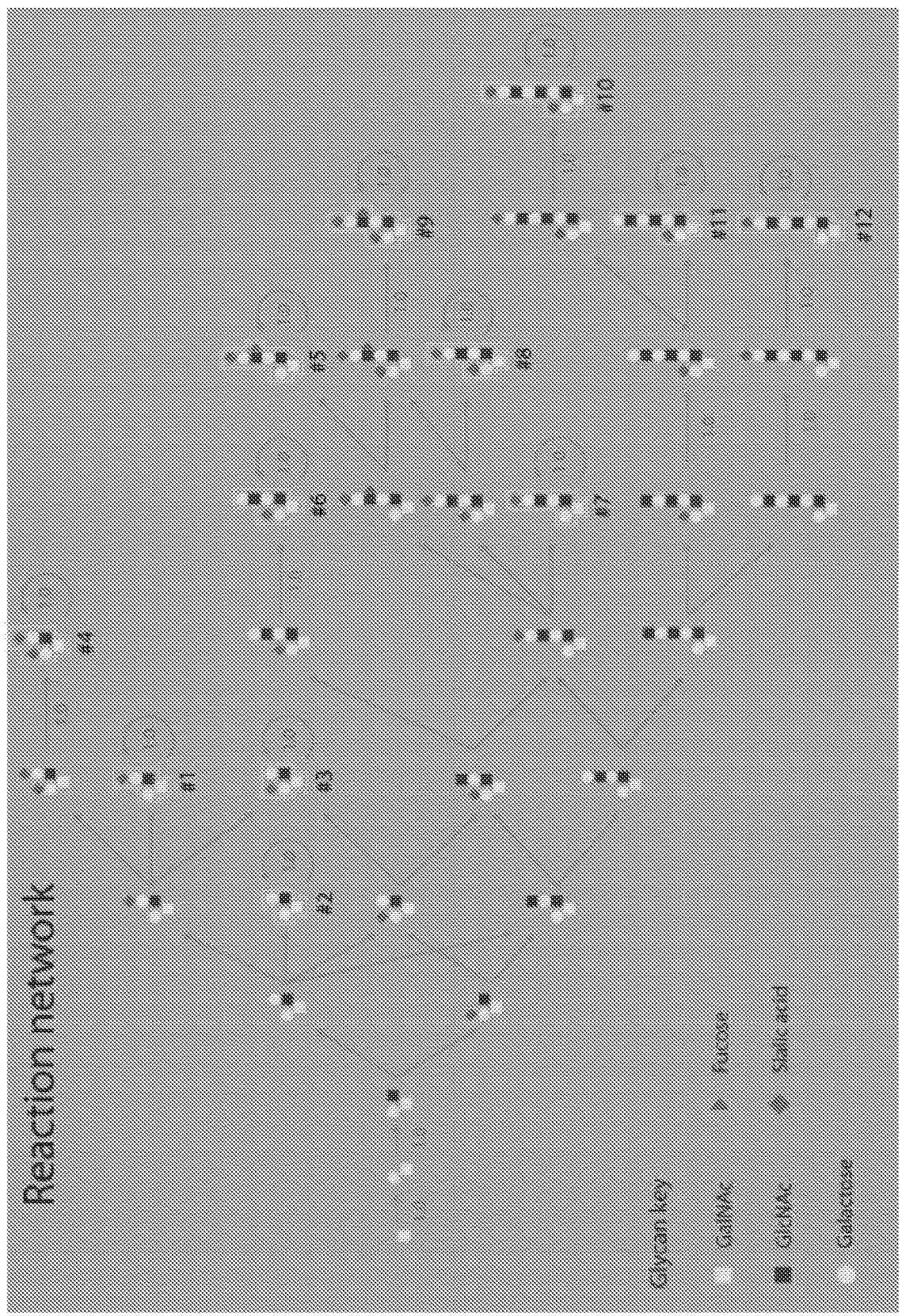
FIG. 37. Exemplification of how the Markovian model framework can be used analogously to describe O-glycosylation networks: The reaction network for the O-glycosylation of the P-selectin glycoprotein ligand (PSGL) as described in (Liu and Neelamegham, 2014) is converted into a Markov model by issuing a transition probability parameter to every reaction and introducing absorbing states (framed glycans) for all glycans appearing in the secreted profile (glycans marked #1-#12).
Figure 38:
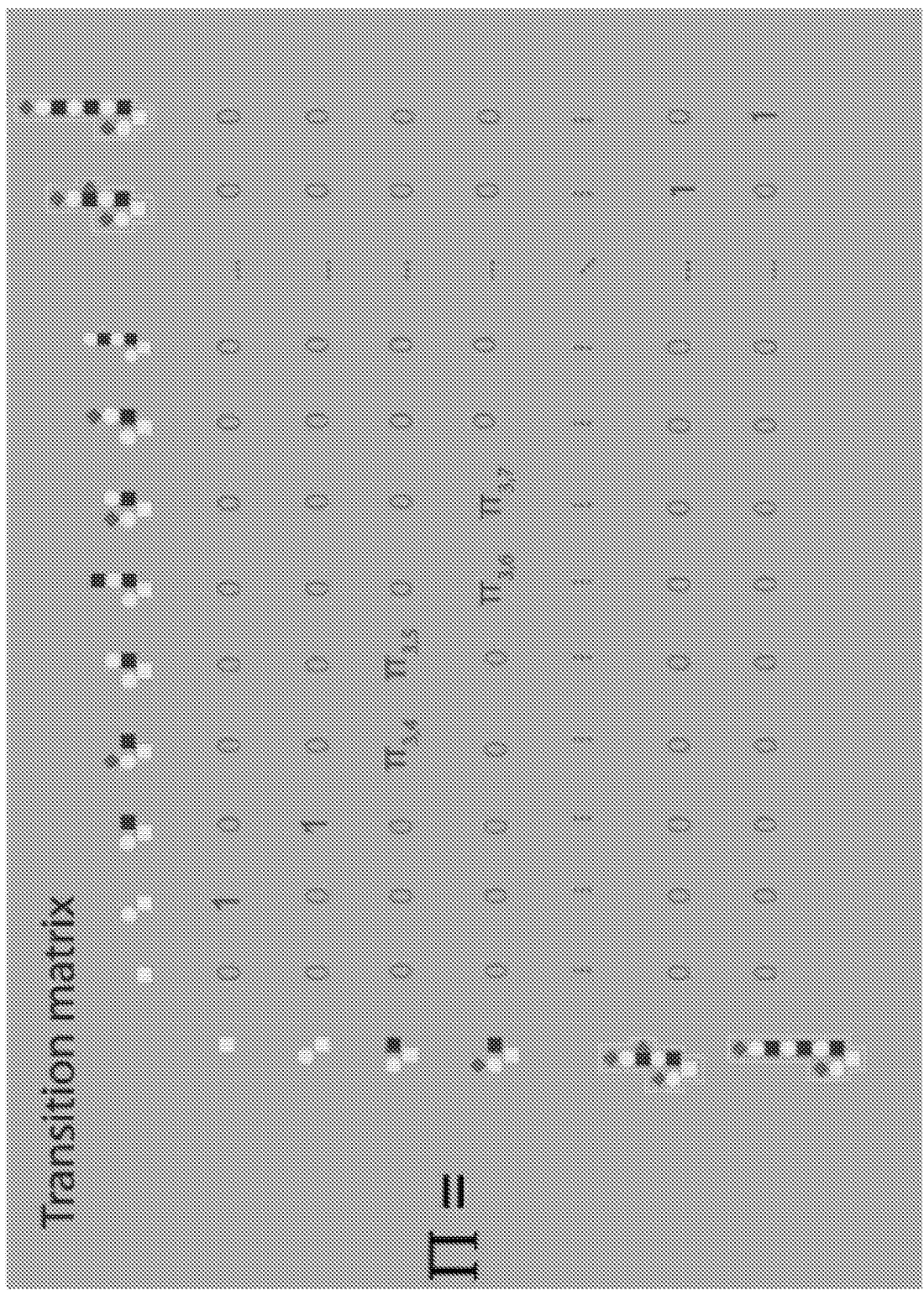
FIG. 38. Transition probabilities are assembled in a Markov transition matrix. By fitting the model to measured frequencies of the secreted glycans #1-#12, these unknown transition probabilities can be inferred as described for N-glycosylation.

The Markov model was tailored to an IgG profile (Gramer et al., 2011) and the fluxes of sugar nucleotides required for the profile were reconstructed. After constraining the sugar nucleotide network to these fluxes, as well as allowing no other nutrient input flux other than glucose and glutamine, optGpSampler (Megchelenbrink et al., 2014) was used to sample the space of possible reaction fluxes from glucose and glutamine uptake to the generation of the required sugar nucleotide fluxes. Subsequently, uptake of galactose or GlcNAc was simulated by constraining the uptake fluxes of these compounds and using methods from the COBRA toolbox ("Minimization of metabolic adjustment") to model how flux in the network would deviate from the reconstructed flux under these new constraints. Simulation of galactose uptake leads to increased flux of UDP-galactose into the Golgi while simulation of GlcNAc uptake leads to decreased flux of UDP-galactose. Accordingly, simulation of glycosylation in these cases yielded increased frequencies of galactosylated glycans in the former case and a decrease in the latter (FIG. 35, FIG. 36), in consistence with experimental data (Gramer et al., 2011; Kildegaard et al., 2015).

Materials and Methods

Cell Cultivation

CHO-S suspension cells (Life Technologies, Thermo Scientific, Rockford, Ill.) were grown in CD CHO medium supplemented with 8 mM L-glutamine and 2 uL/mL anti-clumping agent (Life Technologies, Thermo Scientific, Rockford, Ill.). Cells were expanded in Corning vent cap shake flasks (Sigma-Aldrich, St. Louis, Mo.) in a humidified incubator at 120 rpm (25 mm orbit), 37° C. and 5% $CO_2$. Viable cell densities were measured using the Nucleo-Counter NC-200 Cell Counter (ChemoMetec, Allerod, Denmark) and cells were passaged into fresh medium every two to three days with seeding densities at $3-5\times10^5$ cells/mL.

Fluorescent Labeled Cas9 Expression Vector Construction

Cloning of the GFP_2A_Cas9 was performed with seamless uracil specific excision reagent (USER) cloning of two PCR products; GFP_2A and the Cas9 expression vector (Ronda et al., 2014) and the PCR was performed with the X7 DNA polymerase (Norholm 2010). Subsequent to DpnI (Thermo Fisher Scientific, Waltham, Mass.) treatment of the backbone fragment (Cas9 expression vector), the amplicons were purified from 1% agarose TAE gel using NucleoSpin® Gel and PCR Clean-up kit (Macherey-Nagel, Düren, Germany). The two PCR products were mixed and treated with USER enzyme (New England Biolabs, Ipswich, Mass.) according to manufacturer's recommendations. Upon USER enzyme treatment, the reaction mixture was transformed into E. coli One Shot® Mach1 competent cells (Life technologies, Paisley, U.K.) according to standard procedures. Transformant cells were selected on 100 µg/mL ampicillin LB plates. The construct was verified by sequencing and purified by NucleoBond® Xtra Midi kit (Macherey-Nagel) according to manufacturer's recommendations. However, an unintended mutation P28L in Cas9 of the GFP_2A_Cas9 expression vector, applied in this study, was later detected. This plasmid was therefore named GFP_2A_Cas9m.

Construction of FUT8 KO Cell Lines Using CRISPR Cas9

CHO-S cells were washed and seeded at $5-6\times10^5$ cells/mL without anti-clumping agents one day prior to transfection. Cells were transfected with expression vectors encoding GFP_2A_Cas9m and sgRNA targeting FUT8 (sgRNA2_F or sgRNA3 F, previous published in Ronda et al., 2014). For each sample, 3 mio cells with a density of $1\times10^6$ cells/mL were transfected in a 6 multiwell plate (BD Biosciences, San Jose, Calif.) with 1.875 µg GFP_2A_Cas9 and 1.875 µg sgRNA using FreeStyle™ MAX reagent together with OptiPRO SFM medium (Life Technologies) according to manufacturer's recommendations. Transfections with pmaxGFP® vector (Lonza, Basel, Switzerland) were applied as control for transfection efficiencies. Two days after transfection, a FACSJazz (BD Biosciences) was used to single sort transfected cells. Before cell sorting, cells were prepared by centrifugation at 100 g for 5 min and resuspended in 1 mL fresh medium. The cells were filtrated through a 40 µm cell strainer to achieve single cell suspension and transferred to a FACS tube. Cells were sorted into 96 well U-bottom plates (BD Biosciences, San Jose, Calif.). 1 cell was seeded per well in 200 uL CD CHO medium containing 8 mM L-glutamine, 1% penicillin-streptomycin and 20% filtrated conditioned medium. After 10 days, anti-clumping agent was added to each well with colonies to reach a final concentration of 2 µL/mL. At day 14, the colonies were moved to 96 well flat bottom plates for further expansion. The confluent colonies were split, and replicated plates were seeded and harvested for deep sequencing analysis when close to confluent. Genomic DNA was extracted from the harvested clonal cells using QuickExtract DNA extraction solution (Epicentre, Illumina, Madison, Wis.) according to manufacturer's instructions and stored at −20° C. Deep sequencing was performed on a MiSeq Benchtop Sequencer (Illumina, San Diego, Calif.) using previous published protocol (Ronda et al., 2014). From the deep sequencing data, one FUT8 KO cell line generated from each of the two sgRNA were selected and expanded (sgRNA2_F cell line FUT8 2029, sgRNA3_F cell line FUT8 2030).

Lectin Stain-Based Phenotypic Analysis of FUT8 Knockout Cells $5\times10^5$ cells in media were centrifuged (200 g, RT, 5 min) and supernatant discarded. Cells were resuspended in either 500 µL media containing 5 µg/mL Hoechst 33342 (Pierce, Thermo Scientific, Rockford, Ill.) or 500 µL media containing 5 µg/mL Hoechst and 20 µg/mL fluorescein-Lens culinary agglutinin (F-LCA, Vector Laboratories, Peterborough, UK) and incubated for 30 minutes at RT in the dark. Cells were washed two times in 1 mL PBS by centrifugation (200 g, RT, 5 min). Finally, cells were resuspended in 500 µL PBS and 20 µL cell suspension was transferred to wells in a 96-well tissue culture treated black/clear® microplate (Greiner Bio-one, Frickenhausen, Germany) and 180 µL PBS was subsequently added to each well. The plate was briefly centrifuged (100 g, 15 s, RT) and fluorescence imaging cytometry was performed on a Celigo Imaging Cell Cytometer (Nexcelom Bioscience, Lawrence, Mass.) using the mask+target1 application. The blue and green fluorescence channels were used as mask (Hoechst) and target1 (F-LCA), respectively.

Glycoprofiling

Exponentially growing cells were seeded at $1\times10^6$ cells/mL in 250 mL Corning vent cap shake flasks (Sigma-Aldrich, St. Louis, Mo.). Four days after seeding, 40 mL supernatant was harvested by centrifugation (2000 g, 15 min, RT). Supernatants were filtered (0.2 µm) and proteins were concentrated to approximately 1.5 mL on Amicon Ultra columns (Merck Millipore, Merck KGaA, Darmstadt, Germany) with 3000 Da cutoff. Concentrates were centrifuged (17,000 g, 15 min, RT) and supernatants were transferred to new tubes. N-glycans from retained proteins were released and fluorescently labeled with GlykoPrep Rapid N-Glycan kit (ProZyme Inc., Hayward, Calif.) according to manufacturer's instructions using 2-aminobenzamide (2-AB) as fluorescent label. Labeled N-glycans were analyzed by LC-MS on a Thermo Ultimate 3000 HPLC with fluorescence detector coupled on-line to a Thermo Velos Pro Iontrap MS. Separation was performed on a BEH Glycan column 100 mm×2.1, 1.7 µm (Waters, Milford, Mass.) using the following buffers: Buffer A: 100% acetonitrile, Buffer B: 50 mM ammonium formate, pH 4.4 adjusted with formic acid and filtered (0.2 µm). Separation gradient from 39% buffer A to 47% buffer A over 16 min at 0.5 mL/min flow rate was applied. Fluorescence detector was set to high power lamp and 360 nm excitation, 428 nm emission. MS settings: full scan: 700-2000 m/z, source fragmentation 60V, polarity negative.

Figure 39:
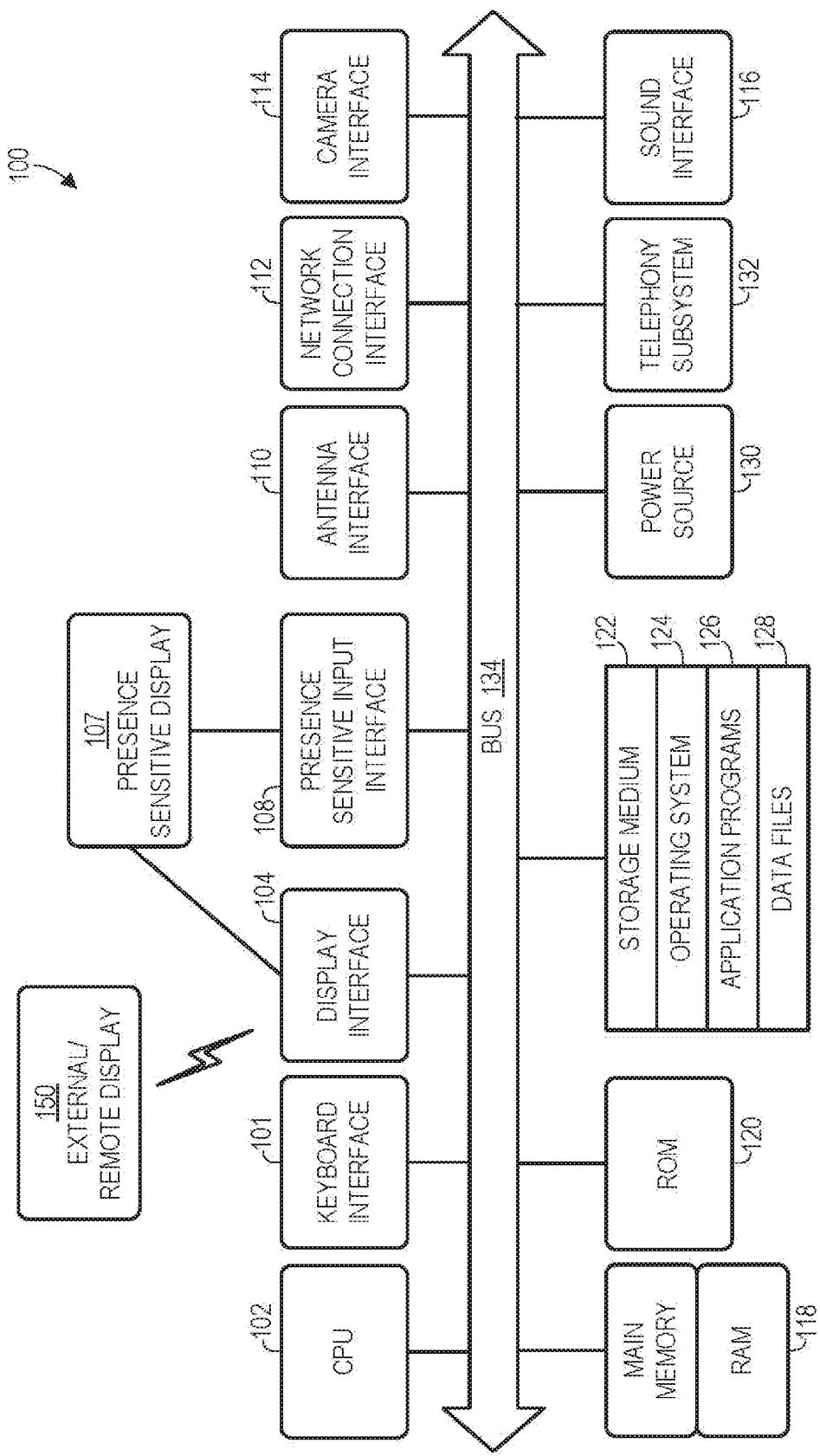
FIG. 39. Block diagram of an illustrative computer system architecture 3900, according to an example implementation.

As desired, implementations of the disclosed technology may include a computing device with more or less of the components illustrated in FIG. 39. It will be understood that the computing device architecture 100 is provided for example purposes only and does not limit the scope of the various implementations of the present disclosed systems, methods, and computer-readable mediums.

The computing device architecture 3900 of FIG. 39 includes a central processing unit (CPU) 3902, where computer instructions are processed; a display interface 3904 that acts as a communication interface and provides functions for rendering video, graphics, images, and texts on the display. In certain example implementations of the disclosed technology, the display interface 3904 may be directly connected to a local display, such as a touch-screen display associated with a mobile computing device. In another example implementation, the display interface 3904 may be configured for providing data, images, and other information for an external/remote display that is not necessarily physically connected to the mobile computing device. For example, a desktop monitor may be used for mirroring graphics and other information that is presented on a mobile computing device. In certain example implementations, the display interface 3904 may wirelessly communicate, for example, via a Wi-Fi channel or other available network connection interface 3912 to the external/remote display.

In an example implementation, the network connection interface 3912 may be configured as a communication interface and may provide functions for rendering video, graphics, images, text, other information, or any combination thereof on the display. In one example, a communication interface may include a serial port, a parallel port, a general purpose input and output (GPIO) port, a game port, a universal serial bus (USB), a micro-USB port, a high definition multimedia (HDMI) port, a video port, an audio port, a Bluetooth port, a near-field communication (NFC) port, another like communication interface, or any combination thereof. In one example, the display interface 3904 may be operatively coupled to a local display, such as a touch-screen display associated with a mobile device. In another example, the display interface 3904 may be configured to provide video, graphics, images, text, other information, or any combination thereof for an external/remote display that is not necessarily connected to the mobile computing device. In one example, a desktop monitor may be used for mirroring or extending graphical information that may be presented on a mobile device. In another example, the display interface 3904 may wirelessly communicate, for example, via the network connection interface 3912 such as a Wi-Fi transceiver to the external/remote display.

The computing device architecture 3900 may include a keyboard interface 3906 that provides a communication interface to a keyboard. In one example implementation, the computing device architecture 3900 may include a presence-sensitive display interface 3908 for connecting to a presence-sensitive display 3907. According to certain example implementations of the disclosed technology, the presence-sensitive display interface 3908 may provide a communication interface to various devices such as a pointing device, a touch screen, a depth camera, etc. which may or may not be associated with a display.

The computing device architecture 3900 may be configured to use an input device via one or more of input/output interfaces (for example, the keyboard interface 3906, the display interface 3904, the presence sensitive display interface 3908, network connection interface 3912, camera interface 3914, sound interface 3916, etc.,) to allow a user to capture information into the computing device architecture 3900. The input device may include a mouse, a trackball, a directional pad, a track pad, a touch-verified track pad, a presence-sensitive track pad, a presence-sensitive display, a scroll wheel, a digital camera, a digital video camera, a web camera, a microphone, a sensor, a smartcard, and the like. Additionally, the input device may be integrated with the computing device architecture 3900 or may be a separate device. For example, the input device may be an accelerometer, a magnetometer, a digital camera, a microphone, and an optical sensor.

Example implementations of the computing device architecture 3900 may include an antenna interface 3910 that provides a communication interface to an antenna; a network connection interface 3912 that provides a communication interface to a network. As mentioned above, the display interface 3904 may be in communication with the network connection interface 3912, for example, to provide information for display on a remote display that is not directly connected or attached to the system. In certain implementations, a camera interface 3914 is provided that acts as a communication interface and provides functions for capturing digital images from a camera. In certain implementations, a sound interface 3916 is provided as a communication interface for converting sound into electrical signals using a microphone and for converting electrical signals into sound using a speaker. According to example implementations, a random access memory (RAM) 3918 is provided, where computer instructions and data may be stored in a volatile memory device for processing by the CPU 3902.

According to an example implementation, the computing device architecture 3900 includes a read-only memory (ROM) 3920 where invariant low-level system code or data for basic system functions such as basic input and output (I/O), startup, or reception of keystrokes from a keyboard are stored in a non-volatile memory device. According to an example implementation, the computing device architecture 3900 includes a storage medium 3922 or other suitable type of memory (e.g. such as RANI, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives), where the files include an operating system 3924, application programs 3926 (including, for example, a web browser application, a widget or gadget engine, and or other applications, as necessary) and data files 3928 are stored. According to an example implementation, the computing device architecture 3900 includes a power source 3930 that provides an appropriate alternating current (AC) or direct current (DC) to power components.

According to an example implementation, the computing device architecture 3900 includes a telephony subsystem 3932 that allows the device 3900 to transmit and receive sound over a telephone network. The constituent devices and the CPU 3902 communicate with each other over a bus 3934.

According to an example implementation, the CPU 3902 has appropriate structure to be a computer processor. In one arrangement, the CPU 3902 may include more than one processing unit. The RAM 3918 interfaces with the computer bus 3934 to provide quick RAM storage to the CPU 3902 during the execution of software programs such as the operating system application programs, and device drivers. More specifically, the CPU 3902 loads computer-executable process steps from the storage medium 3922 or other media into a field of the RAM 3918 in order to execute software programs. Data may be stored in the RAM 3918, where the data may be accessed by the computer CPU 3902 during execution. In one example configuration, the device architecture 3900 includes at least 3928 MB of RAM, and 256 MB of flash memory.

The storage medium 3922 itself may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, an external mini-dual in-line memory module (DIMM) synchronous dynamic random access memory (SDRAM), or an external micro-DIMM SDRAM. Such computer readable storage media allow a computing device to access computer-executable process steps, application programs and the like, stored on removable and non-removable memory media, to off-load data from the device or to upload data onto the device. A computer program product, such as one utilizing a communication system may be tangibly embodied in storage medium 3922, which may comprise a machine-readable storage medium.

According to one example implementation, the term computing device, as used herein, may be a CPU, or conceptualized as a CPU (for example, the CPU 3902 of FIG. 39). In this example implementation, the computing device (CPU) may be coupled, connected, and/or in communication with one or more peripheral devices, such as display. In another example implementation, the term computing device, as used herein, may refer to a mobile computing device such as a smartphone, tablet computer, or smart watch. In this example implementation, the computing device may output content to its local display and/or speaker(s). In another example implementation, the computing device may output content to an external display device (e.g., over Wi-Fi) such as a TV or an external computing system.

In example implementations of the disclosed technology, a computing device may include any number of hardware and/or software applications that are executed to facilitate any of the operations. In example implementations, one or more I/O interfaces may facilitate communication between the computing device and one or more input/output devices. For example, a universal serial bus port, a serial port, a disk drive, a CD-ROM drive, and/or one or more user interface devices, such as a display, keyboard, keypad, mouse, control panel, touch screen display, microphone, etc., may facilitate user interaction with the computing device. The one or more I/O interfaces may be used to receive or collect data and/or user instructions from a wide variety of input devices. Received data may be processed by one or more computer processors as desired in various implementations of the disclosed technology and/or stored in one or more memory devices.

One or more network interfaces may facilitate connection of the computing device inputs and outputs to one or more suitable networks and/or connections; for example, the connections that facilitate communication with any number of sensors associated with the system. The one or more network interfaces may further facilitate connection to one or more suitable networks; for example, a local area network, a wide area network, the Internet, a cellular network, a radio frequency network, a Bluetooth enabled network, a Wi-Fi enabled network, a satellite-based network any wired network, any wireless network, etc., for communication with external devices and/or systems.

In the foregoing description, numerous specific details are set forth. It is to be understood, however, that implementations of the disclosed technology may be practiced without these specific details. In other instances, well-known methods, structures and techniques have not been shown in detail in order not to obscure an understanding of this description. References to "one implementation," "an implementation," "example implementation," "various implementations," etc., indicate that the implementation(s) of the disclosed technology so described may include a particular feature, structure, or characteristic, but not every implementation necessarily includes the particular feature, structure, or characteristic. Further, repeated use of the phrase "in one implementation" does not necessarily refer to the same implementation, although it may.

Throughout the specification and the claims, the following terms take at least the meanings explicitly associated herein, unless the context clearly dictates otherwise. The term "connected" means that one function, feature, structure, or characteristic is directly joined to or in communication with another function, feature, structure, or characteristic. The term "coupled" means that one function, feature, structure, or characteristic is directly or indirectly joined to or in communication with another function, feature, structure, or characteristic. The term "or" is intended to mean an inclusive "or." Further, the terms "a," "an," and "the" are intended to mean one or more unless specified otherwise or clear from the context to be directed to a singular form.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

Certain implementations of the disclosed technology are described above with reference to block and flow diagrams of systems and methods and/or computer program products according to example implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some implementations of the disclosed technology.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks.

Implementations of the disclosed technology may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

Beyond computer architecture, implementations of the disclosed technology may include a machine that includes a computing device with more or less of the components illustrated in FIG. 39. It will be understood that the device architecture, mechanical components, and steps are provided for example purposes only and do not limit the scope of the various implementations. This is provided as an example of a machine that can be developed to implement the processes claimed here.

A machine that carries out the processes described here could do the following. The machine could have a device to culture cells. At a desired timepoint, the glycoprofile will be measured in an approach such as the following. The machine could extract the supernatent or sacrifice the cells. The glycans are then purified from the sample through chromatographic methods and/or enzymatic treatment (e.g., PNGase, glycosidases) using methods established by those skilled in the art. The purified glycans (or glycopeptides or glycolipids) can be quantified using an online chromatographic method (e.g., HPLC using various types of columns). The glycans can either be quantified using chromatographic peaks or fed into a mass spectrometer and quantified using peak heights. The quantities can then be fed into the model and the algorithm described here can scan combinations of knockout, overexpression, and/or changes in media feed. The machine can then implement these (e.g., with online media adjustment, or a vessel that would add pre-designed genetic engineering tools, such as CRISPR guide RNAs, shRNAs, or other tools). Cells with genetic modifications can be sorted on-line or off-line by the user using fluorescence assisted cell sorting, microfluidic devices, or other tools. Then edited cells or optimized media are deployed. The cells can be grown and ultimately the glycoprofile can be measured online again, and data can be fed back into the model to identify a second round of edits to match the desired change. This can be iterated until the desired glycoprofile is obtained. The software would include the generic network and algorithms.

Throughout the specification various citations are referenced, and the entire content of each is hereby incorporated by reference. The following example is provided to describe the invention in more detail. It is intended to illustrate, not to limit the invention.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method comprising:
   generating, by a computing device, using a known initial structure and a plurality of known glycosylation enzymes and/or reactions, a generic glycosylation reaction network comprising a plurality of glycans;

receiving, at the computing device, information relating to a measured glycoprofile of a particular protein, the measured glycoprofile comprising a plurality of glycoprofile glycans, each having an associated relative frequency;

tailoring the generic glycosylation reaction network to the measured glycoprofile to provide a tailored network, the tailored network comprising a reduced set of the plurality of glycans, the reduced set including the glycoprofile glycans;

transforming the tailored network into a Markov chain, the Markov chain representing a stochastic network wherein each glycoprofile glycan in the reduced set is regarded as a state in the stochastic network that can transition to another state in the stochastic network with a particular transition probability;

determining reaction conditions that approximate the particular transition probabilities that define a set of desired states in the stochastic network; and culturing cells under the reaction conditions that approximate said particular transition probabilities, thereby producing a desired glycoprofile glycan.

2. The method of claim 1, wherein the plurality of glycans can be synthesized (i) by combined action of the plurality of known enzymes or (ii) through chemical reactions.

3. The method of claim 1, wherein the known initial structure is $Man_9GlcNAc_2$.

4. The method of claim 1, wherein the generic glycosylation reaction network is a flux-balance network; and the associated relative frequencies are obtained experimentally and wherein the associated relative frequencies are obtained experimentally through at least one of mass spectrometry-coupled liquid chromatography (LC-MS), liquid chromatography, and liquid chromatography lectin arrays.

5. The method of claim 1, wherein tailoring the generic glycosylation reaction network comprises identifying a plurality of reactions not required to obtain the plurality of glycoprofile glycans.

6. The method of claim 1, wherein the tailored network represents a reaction topology describing how flux from a known initial structure leads to generation of the measured glycoprofile, and wherein the tailored network provides a minimal reaction network for producing the measured glycoprofile.

7. The method of claim 1, wherein tailoring the generic glycosylation reaction network comprises using model reduction through convex analysis or optimization algorithms.

8. The method of claim 1, wherein transforming the tailored network into a Markov chain comprises:

assessing variance in reaction fluxes of the tailored network using Monte Carlo sampling, the Monte Carlo sampling producing a plurality of flux vectors having an associated variance, wherein each reaction flux represents a path through the tailored network from the known initial structure to the measured glycoprofile; and reformulating each of the plurality of flux vectors into a plurality of associated transition probabilities.

9. The method of claim 1, further comprising:
simulating a perturbation in the tailored network by modifying the Markov chain to determine how the perturbation will affect the measured glycoprofile.

10. The method of claim 9, wherein the perturbation is a decrease in activity of a particular enzyme and simulating the decrease in the activity of the particular enzyme comprises:

identifying a first subset of reactions in the tailored network that depend on the particular enzyme, a second subset of reactions in the tailored network representing the remaining reactions in the tailored network that do not depend on the particular enzyme;

scaling down, by a user-provided factor, the first subset of reactions to provide a set of scaled-down reactions;

modifying, based on the scaled-down reactions, transition probabilities associated with the second subset of reactions; and generating an updated Markov chain yielding a predicted glycoprofile gained through the decrease in activity of the particular enzyme.

11. The method of claim 9, wherein the perturbation is an upregulation in activity of a particular enzyme and simulating the upregulation in the activity of the particular enzyme comprises:

identifying a first subset of reactions in the tailored network that depend on the particular enzyme, a second subset of reactions in the tailored network representing the remaining reactions in the tailored network that do not depend on the particular enzyme;

scaling up, by a user-provided factor, the first subset of reactions to provide a set of scaled-up reactions;

modifying, based on the scaled-up reactions, transition probabilities associated with the second subset of reactions; and generating an updated Markov chain yielding a predicted glycoprofile gained through the upregulation in activity of the particular enzyme.

12. The method of claim 1, wherein the Markov chain has an absorption probability, and the absorption probability provides the Markov chain's probability of reaching an absorbing state from the known initial structure.

13. The method of claim 1, wherein the generic glycosylation reaction network describes at least one selected from the group comprising N-glycosylation, O-glycosylation, oligosaccharide synthesis, synthesis of glucosaminoglycans, glycolipids, proteoglycans, glycoconjugates, and peptidoglycans.

14. The method of claim 1 further comprising determining an optimal combination of changes to match a desired glycoprofile by:

providing an optimization algorithm for implementing an optimization process that simulates possible perturbations that lead to a desired glycoprofile, the optimization algorithm minimizing an objective function that measures a distance between a predicted and an observed glycoprofile;

receiving an initial hypothesis of perturbations and a stopping condition; and determining an end point of the optimization process, wherein the end point represents the optimal combination of changes and comprises a set of perturbations that provides a simulated glycoprofile within a specified margin of error of the desired glycoprofile.

15. The method of claim 14, wherein the simulated possible perturbations reduce or increase enzyme activity, change enzyme substrates or change media conditions.

16. The method of claim 1, further comprising:
a) tailoring the generic glycosylation reaction network for alternative localization;
b) separately simulating alternatives and comparing resulting predicted glycoprofiles to a desired glycoprofile; and
c) changing localization of glycosylation enzymes based at least in part on the separately simulated alternatives and comparison of resulting predicted glycoprofiles to the desired glycoprofile of step b).

17. The method of claim 16, wherein predictions are used to change localization of glycosylation enzymes to change the glycoprofile.

18. One or more computer-readable media having stored thereon executable instructions that when executed by one or more processors configure a computer system to perform the method according to claim 1.

19. A system comprising:
- a computing device;
- a memory device; and
- a cell culturing device,
- wherein the memory device has stored thereon executable instructions that when executed by one or more processors of the computing device configure the computing device to perform the method according to claim 1, and
- wherein the cell culturing device is configured to culture cells under the reaction conditions that approximate the particular transition probabilities, thereby producing the desired glycoprofile glycan corresponding to the state in the stochastic network based on instructions from the computing device.

20. The method of claim 1, wherein the reaction conditions under which the culturing of the cells is performed include a genetic modification of the cells.

21. The method of claim 1, wherein the reaction conditions under which the culturing of the cells is performed include a modification of a culture medium in which the cells are cultured.

* * * * *